US009133097B2

(12) United States Patent
Saba et al.

(10) Patent No.: US 9,133,097 B2

(45) Date of Patent: Sep. 15, 2015

(54) USE OF UNSATURATED SPHINGOSINE COMPOUNDS AS CHEMOTHERAPEUTIC AGENTS FOR THE TREATMENT OF CANCER

(71) Applicants: Children's Hospital & Research Center at Oakland, Oakland, CA (US); Research Foundation of the City University of New York, New York, NY (US)

(72) Inventors: Julie D. Saba, Oakland, CA (US); Henrik Fyrst, Oakland, CA (US); Robert Bittman, Roslyn Heights, NY (US)

(73) Assignees: Children's Hospital & Research Center at Oakland, Oakland, CA (US); Research Foundation of the City University of New York, New York, NY (US)

( * ) Notice: Subject to any disclaimer, the term of this patent is extended or adjusted under 35 U.S.C. 154(b) by 0 days.

(21) Appl. No.: 14/261,175

(22) Filed: Apr. 24, 2014

(65) Prior Publication Data

US 2015/0051207 A1 Feb. 19, 2015

Related U.S. Application Data

(62) Division of application No. 12/747,253, filed as application No. PCT/US2008/086581 on Dec. 12, 2008, now Pat. No. 8,741,967.

(60) Provisional application No. 61/013,230, filed on Dec. 12, 2007.

(51) Int. Cl.

*C07C 215/24* (2006.01)
*A61K 31/133* (2006.01)
*A61K 8/68* (2006.01)
*A61K 31/352* (2006.01)
*A61K 31/436* (2006.01)
*A61K 31/5377* (2006.01)

(52) U.S. Cl.

CPC ................ *C07C 215/24* (2013.01); *A61K 8/68* (2013.01); *A61K 31/133* (2013.01); *A61K 31/352* (2013.01); *A61K 31/436* (2013.01); *A61K 31/5377* (2013.01)

(58) Field of Classification Search

CPC ...... C07C 215/24; A61K 8/68; A61K 31/133; A61K 31/352; A61K 31/436; A61K 31/5377

See application file for complete search history.

(56) References Cited

U.S. PATENT DOCUMENTS 6,255,336 B1 7/2001 Shayman et al.
7,109,244 B2 9/2006 Rinehart et al.
2001/0041683 A1 11/2001 Schmitz et al.
2002/0198240 A1 12/2002 Shayman et al.
2003/0073680 A1 4/2003 Shayman et al.
2004/0247603 A1 12/2004 Sabbadini
2006/0171946 A1 8/2006 Sabbadini

FOREIGN PATENT DOCUMENTS

EP 1 325 904 7/2003
JP 2006-55071 3/2006
KR 10-2005-0051862 6/2005
WO 95/34307 12/1995
WO 99/41266 8/1999
WO 01/04108 1/2001
WO 01/16093 3/2001
WO 02/46765 6/2002
WO 02/051439 7/2002
WO 02/062777 8/2002
WO 03/101386 12/2003
WO 2004/014271 2/2004
WO 2004/054963 7/2004
WO 2006/081158 8/2006
WO 2007/053447 5/2007

OTHER PUBLICATIONS

Sugawara, et al., Apoptosis Induction by Wheat-flour Sphingoid Bases in DLD-1 Human Colon Cancer Cells, 66 Biosci. Biotechnol. Biochem. 2228 (2002).*

Cateni, et al, Preliminary Biological Assay on Cerebroside Mixture from *Euphorbia nicaeensis*All. Isolation and Structure Determination of Five Glucocerebrosides, 58 IL FARMACO 809 (2003).*

Abeytunga et al., "Presence of unsaturated sphingomyelins and changes in their composition during the life cycle of the moth *Manduca sexta*," *Journal of Lipid Research 45*:1221-1231, 2004.

Abnet et al., "A Cross-Sectional Study of Human Serum Sphingolipids, Diet and Physiologic Parameters," *The Journal of Nutrition 131*(10):2748-2752, 2001.

Aguilar et al., "Control of fatty acid desaturation: a mechanism conserved from bacteria to humans," *Molecular Microbiology 62*(6):1507-1514, 2006.

Ahn et al., "Sphingoid Bases and Ceramide Induce Apoptosis in HT-29 and HCT-116 Human Colon Cancer Cells," *Exp. Biol. Med. 277*(5):345-353, 2002.

Akiyama, "Mini Review: Wnt/β-catenin signaling," *Cytokine& Growth Factor Reviews 11*:273-282, 2000.

Berra et al., "Dietary sphingolipids in colorectal cancer prevention," *European Journal of Cancer Prevention 11*:193-197, 2002.

Carpten et al., "A transforming mutation in the pleckstrin homology domain of AKT1 in cancer," *Nature 448*:439-444, 2007.

Cateni et al., "Preliminary biological assay on cerebroside mixture from *Euphorbia nicaeensis* All. Isolation and structure determination of five glucocerebrosides," *Farmaco 58*:809-817, 2003.

Chun et al., "Synthesis of New Trans Double-Bond Sphingolipid Analogues: $\Delta^{4,6}$ and $\Delta^{6}$ Ceramides," *J. Org. Chem. 67*:2600-2605, 2002.

(Continued)

*Primary Examiner* — Sean Basquill

(74) *Attorney, Agent, or Firm* — Seep IP Law Group PLLC

(57) ABSTRACT

The present invention is directed to unsaturated sphingosine compounds which are useful as therapeutic agents for the treatment of cancer and for the treatment of other diseases including diabetes and infection with intracellular bacteria. The invention is also directed to methods of using the compounds and pharmaceutical compositions comprising the compounds in treating these diseases.

12 Claims, 10 Drawing Sheets

(56) References Cited

OTHER PUBLICATIONS

Colsch et al., "Characterization of the ceramide moieties of sphingoglycolipids from mouse brain by ESI-MS/MS:identification of ceramides containing sphingadienine," *Journal of Lipid Research 45*:281-286, 2004.
Fayard et al., "Protein kinase B/Akt at a glance," *Journal of Cell Science 118*(24):5675-5678, 2005.
Fyrst et al., "Characterization of free endogenous $C_{14}$ and $C_{16}$ sphingoid bases from *Drosophila melanogaster*," *Journal of Lipid Research 45*:54-62, 2004.
Fyrst et al., "Identification and characterization by electrospray mass spectrometry of endogenous *Drosophila*sphingadienes," *Journal of Lipid Research 49*:597-606, 2008.
Garton et al., "The dihydroceramide desaturase is not essential for cell viability in *Schizosaccharomyces pombe*," *FEBS Letters 538*:192-196, 2003.
Goswami et al., "The Phosphoinositide 3-Kinase/Aktl/Par-4 Axis: A Cancer-Selective Therapeutic Target," *Cancer Research 66*(6):2889-2892, 2006.
Han et al., "Cytotoxic Constituents of the Octocoral *Dendronephthya gigantea*," *Arch. Pharm. Res. 28*(3):290-293, 2005.
Herr et al., "*Sply*regulation of sphingolipid signaling molecules is essential for *Drosophila* development," *Development 130*:2443-2453, 2003.
Huang et al., "Targeting mTOR signaling for cancer therapy," *Current Opinion in Pharmacology 3*:371-377, 2003.
Huang et al., "Adenomatous Polyposis Coli Determines Sensitivity to Histone Deacetylase Inhibitor-Induced Apoptosis in Colon Cancer Cells," *Cancer Research 66*(18):9245-9251, 2006.
Huwiler et al., "Altering the Sphingosine-1-Phosphate/Ceramide Balance: A Promising Approach for Tumor Therapy," *Current Pharmaceutical Design 12*:4625-4635, 2006.
Ilyas et al., "β-Catenin mutations in cell lines established from human colorectal cancers," *Proc. Natl. Acad. Sci. USA 94*:10330-10334, 1997.
Kim et al., "Akt: Versatile Mediator of Cell Survival and Beyond," *Journal of Biochemistry and Molecular Biology 35*(1):106-115, 2002.
Kohno et al., "Intracellular Role for Sphingosine Kinase 1 in Intestinal Adenoma Cell Proliferation," *Molecular and Cellular Biology 26*(19):7211-7223, 2006.
Kuijl et al., "Intracellular bacterial growth is controlled by a kinase network around PKB/AKT1," *Nature 450*:725-730, 2007.
Kwon et al., "Sphingolipids from Bombycis Corpus 101A and Their Neurotrophic Effects," *J. Nat. Prod. 66*:466-469, 2003.
Lemonnier et al., "Sphingomyelin in the suppression of colon tumors: prevention versus intervention," *Archives of Biochemistry and Biophysics 419*:129-138, 2003.
Levine et al., "Coordination and communication between the p53 and IGF-1—AKT—TOR signal transduction pathways," *Genes & Development 20*:267-275, 2006.
Liu et al., "Ceramide glycosylation potentiates cellular multidrug resistance," *The FASEB Journal 15*:719-730, 2001.
Lynch et al., "An introduction to plant sphingolipids and a review of recent advances in understanding their metabolism and function," *New Phytologist 161*:677 -702, 2004.
Martin et al., "Regulation of long chain unsaturated fatty acid synthesis in yeast," *Biochimica et Biophysica Acta 1771*:271-285, 2007.
Mochizuki et al., "Akt Protein Kinase Inhibits Non-apoptotic Programmed Cell Death Induced by Ceramide," *The Journal of Biological Chemistry 277*(4):2790-2797, 2002.
Moran et al., "Apc Deficiency Is Associated with Increased Egfr Activity in the Intestinal Enterocytes and Adenomas of C57BL/6J-Min/+Mice," *The Journal of Biological Chemistry 279*(41):43261-43272, 2004.
Murakami et al., "Efficient stereocontrolled synthesis of sphingadienine derivatives," *Tetrahedron 61*:9233-9241, 2005.
Muralidhar et al., "New Sphingolipids and a Sterol from a *Lobophytum* Species of the Indian Ocean," *Chem. Pharm. Bull. 53*(2):168-171, 2005.
Nagle et al., "New Glycosphingolipids from the Marine Sponge *Halichondria Panacea*," *Journal of Natural Products 55*(7):1013-1017, 1992.
Noda et al., "Isolation and characterization of a novel type of glycosphingolipid from *Neanthes diversicolor*," *Biochimica et Biophysica Acta 1169*:30-38, 1993.
Oki et al., "Impact of PTEN/AKT/PI3K signal pathway on the chemotherapy for gastric cancer," Abstract, Journal of Clinical Oncology 2006 ASCO Annual Meeting Proceedings (Post-Meeting Edition) 24(18S), 1 page, 2006.
Oskouian et al., "Death and taxis: what non-mammalian models tell us about sphingosine-1-phosphate," *Seminars in Cell & Developmental Biology 15*:529-540, 2004.
Oskouian et al., "Sphingosine-1-phosphate lyase potentiates apoptosis via p53- and p38-dependent pathways and is down-regulated in colon cancer," *PNAS 103*(46):17384-17389, 2006.
Panganamala et al., "Long-chain bases in the sphingolipids of atherosclerotic human aorta," *Journal of Lipid Research 10*:445-455, 1969.
Phan et al., "Disruption of Sphingolipid Metabolism Elicits Apoptosis-Associated Reproductive Defects in *Drosophila*," *Dev. Biol. 309*(2):329-341, 2007.
Pizarro-Cerdá, et al., "Subversion of phosphoinositide metabolism by intracellular bacterial pathogens," *Nature Cell Biology 6*(11): 1026-1033, 2004.
Powell et al., "Ceramide Disables 3-Phosphoinositide Binding to the Pleckstrin Homology Domain of Protein Kinase B (PKB)/Akt by a PKCξ-Dependent Mechanism," *Molecular and Cellular Biology 23*(21):7794-7808, 2003.
Radin, "Killing tumours by ceramide-induced apoptosis: a critique of available drugs," *Biochem. J. 371*:243-256, 2003.
Radin, "Designing Anticancer Drugs Via the Achilles Heel: Ceramide, Allylic Ketones, and Mitochondria," *Bioorganic & Medicinal Chemistry 11*:2123-2142, 2003.
Renkonen et al., "Structure of plasma sphingadienine," *Journal of Lipid Research 10*:687-693, 1969.
Renkonen, "Presence of sphingadienine and *trans*-monoenoic fatty acids in ceramide monohexosides of human plasma," *Biochimica et Biophysica Acta 210*:190-192, 1970.
Row et al., "Cerebrosides and Tocopherol Trimers from the Seeds of *Euryale ferox*," *Journal of Natural Products 70*:1214-1217, 2007.
Ruggero et al., "The Akt of translational control," *Oncogene 24*:7426-7434, 2005.
Salinas et al , "Inhibition of PKB/Aktl by C2-Ceramide Involves Activation of Ceramide-Activated Protein Phosphatase in PC12 Cells," *Molecular and Cellular Neuroscience 15*:156-169, 2000.
Sansal et al., "The Biology and Clinical Relevance of the PTEN Tumor Suppressor Pathway," *Journal of Clinical Oncology 22*(14):2954-2963, 2004.
Schmelz et al., "Sphingomyelin Consumption Suppresses Aberrant Colonic Crypt Foci and Increases the Proportion of Adenomas versus Adenocarcinomas in CF1 Mice Treated with 1,2-Dimethylhydrazine: Implications for Dietary Sphingolipids and Colon Carcinogenesis," *Cancer Research 56*:4936-4941, 1996.
Schmelz et al., "Modulation and Intracellular β-Catenin Localization and Intestinal Tumorigenesis in Vivo and in Vitro by Sphingolipids," *Cancer Research 61*:6723-6729, 2001.
Sitrin et al., "Isolation and Structure Determination of *Pachybasium* Cerebrosides which Potentiate the Antifungal Activity of Aculeacin," *The Journal of Antibiotics XLI*(4):469-480, 1988.
Stoica et al., "Ceramide-induced neuronal apoptosis is associated with dephosphorylation of AKT, BAD, FKHR, GSK-3β, and induction of the mitochondrial-dependent intrinsic caspase pathway," *Molecular and Cellular Neuroscience 22*:365-382, 2003.
Struckhoff et al., "Novel Ceramide Analogs as Potential Chemotherapeutic Agents in Breast Cancer," *The Journal of Pharmacology and Experimental Therapeutics 309*(2):523-532, 2004.
Sugawara et al., "Apoptosis Induction by Wheat-flour Sphingoid Bases in DLD-1 Human Colon Cancer Cells," *Biosci. Biotechnol. Biochem. 66*(10):2228-2231, 2002.
Sugawara et al., "Isolation of Sphingoid Bases of Sea Cucumber Cerebrosides and Their Cytotoxicity against Human Colon Cancer Cells," *Biosci. Biotechnol. Biochem. 70*(12):2906-2912, 2006.

(56) References Cited

OTHER PUBLICATIONS

Sullards et al., "Structure determination of soybean and wheat glucosylceramides by tandem mass spectrometry," *Journal of Mass Spectrometry 35*:347-353, 2000.
Sweeney et al., "Sphingosine and Its Methylated Derivative N,N-Dimethylsphingosine (DMS) Induce Apoptosis in a Vairety of Human Cancer Cell Lines," *Int. J. Cancer 66*:358-366, 1996.
Symolon et al., "Dietary Soy Sphingolipids Suppress Tumorigenesis and Gene Expression in 1,2-Dimethylhydrazine-Treated CF1 Mice and Apc$^{Min/+}$ Mice[1,2]," *The Journal of Nutrition 134*(5):1157-1161, 2004.
Takakuwa et al., "Isolation and Characterization of the Genes Encoding $\Delta^8$ -Sphingolipid Desaturase from *Saccharomyces kluyveri* and *Kluyveromyces lactis," Current Microbiology 45*:459-461, 2002.
Tan et al., "New Cerebrosides from the Basidiomycete *Cortinarius tenuipes," Lipids, 38*(1):81-84 2003.
Ternes et al., "Identification and Characterization of a Sphingolipid Δ4-Desaturase Family," *The Journal of Biological Chemistry 277*(28):25512-25518, 2002.
Toker et al., "Akt Signaling and Cancer: Surviving but not Moving On," *Cancer Research 66*(8):3963-3966, 2006.
Vivanco et al., "The Phosphatidylinositol 3-Kinase-AKT Pathway in Human Cancer," *Nature Reviews: Cancer 2*:489-501, 2002.
Woodgett, "Recent advances in the protein kinase B signaling pathway," *Current Opinion in Cell Biology 17*:150-157, 2005.
Zheng et al., "Ceramides and other bioactive sphingolipid backbones in health and disease: Lipidomic analysis, metabolism and roles in membrane structure, dynamics, signaling and autophagy," *Biochimica et Biophysica Acta 1758*:1864-1884, 2006.

* cited by examiner

SEQUENCE LISTING

```
<160> NUMBER OF SEQ ID NOS: 6

<210> SEQ ID NO 1
<211> LENGTH: 480
<212> TYPE: PRT
```

```
<213> ORGANISM: Homo sapiens

<400> SEQUENCE: 1

Met Ser Asp Val Ala Ile Val Lys Glu Gly Trp Leu His Lys Arg Gly
 1               5                  10                  15

Glu Tyr Ile Lys Thr Trp Arg Pro Arg Tyr Phe Leu Leu Lys Asn Asp
            20                  25                  30

Gly Thr Phe Ile Gly Tyr Lys Glu Arg Pro Gln Asp Val Asp Gln Arg
        35                  40                  45

Glu Ala Pro Leu Asn Asn Phe Ser Val Ala Gln Cys Gln Leu Met Lys
    50                  55                  60

Thr Glu Arg Pro Arg Pro Asn Thr Phe Ile Ile Arg Cys Leu Gln Trp
65                  70                  75                  80

Thr Thr Val Ile Glu Arg Thr Phe His Val Glu Thr Pro Glu Glu Arg
                85                  90                  95

Glu Glu Trp Thr Thr Ala Ile Gln Thr Val Ala Asp Gly Leu Lys Lys
            100                 105                 110

Gln Glu Glu Glu Glu Met Asp Phe Arg Ser Gly Ser Pro Ser Asp Asn
        115                 120                 125

Ser Gly Ala Glu Glu Met Glu Val Ser Leu Ala Lys Pro Lys His Arg
    130                 135                 140

Val Thr Met Asn Glu Phe Glu Tyr Leu Lys Leu Leu Gly Lys Gly Thr
145                 150                 155                 160

Phe Gly Lys Val Ile Leu Val Lys Glu Lys Ala Thr Gly Arg Tyr Tyr
                165                 170                 175

Ala Met Lys Ile Leu Lys Lys Glu Val Ile Val Ala Lys Asp Glu Val
            180                 185                 190

Ala His Thr Leu Thr Glu Asn Arg Val Leu Gln Asn Ser Arg His Pro
        195                 200                 205

Phe Leu Thr Ala Leu Lys Tyr Ser Phe Gln Thr His Asp Arg Leu Cys
    210                 215                 220

Phe Val Met Glu Tyr Ala Asn Gly Gly Glu Leu Phe Phe His Leu Ser
225                 230                 235                 240

Arg Glu Arg Val Phe Ser Glu Asp Arg Ala Arg Phe Tyr Gly Ala Glu
                245                 250                 255

Ile Val Ser Ala Leu Asp Tyr Leu His Ser Glu Lys Asn Val Val Tyr
            260                 265                 270

Arg Asp Leu Lys Leu Glu Asn Leu Met Leu Asp Lys Asp Gly His Ile
        275                 280                 285

Lys Ile Thr Asp Phe Gly Leu Cys Lys Glu Gly Ile Lys Asp Gly Ala
    290                 295                 300

Thr Met Lys Thr Phe Cys Gly Thr Pro Glu Tyr Leu Ala Pro Glu Val
305                 310                 315                 320

Leu Glu Asp Asn Asp Tyr Gly Arg Ala Val Asp Trp Trp Gly Leu Gly
                325                 330                 335

Val Val Met Tyr Glu Met Met Cys Gly Arg Leu Pro Phe Tyr Asn Gln
            340                 345                 350

Asp His Glu Lys Leu Phe Glu Leu Ile Leu Met Glu Glu Ile Arg Phe
        355                 360                 365

Pro Arg Thr Leu Gly Pro Glu Ala Lys Ser Leu Leu Ser Gly Leu Leu
    370                 375                 380

Lys Lys Asp Pro Lys Gln Arg Leu Gly Gly Gly Ser Glu Asp Ala Lys
385                 390                 395                 400
```

```
Glu Ile Met Gln His Arg Phe Phe Ala Gly Ile Val Trp Gln His Val
                405                 410                 415

Tyr Glu Lys Lys Leu Ser Pro Pro Phe Lys Pro Gln Val Thr Ser Glu
            420                 425                 430

Thr Asp Thr Arg Tyr Phe Asp Glu Glu Phe Thr Ala Gln Met Ile Thr
        435                 440                 445

Ile Thr Pro Pro Asp Gln Asp Asp Ser Met Glu Cys Val Asp Ser Glu
    450                 455                 460

Arg Arg Pro His Phe Pro Gln Phe Ser Tyr Ser Ala Ser Gly Thr Ala
465                 470                 475                 480


<210> SEQ ID NO 2
<211> LENGTH: 724
<212> TYPE: PRT
<213> ORGANISM: Homo sapiens

<400> SEQUENCE: 2

Met Ser Ala Glu Gly Tyr Gln Tyr Arg Ala Leu Tyr Asp Tyr Lys Lys
 1               5                  10                  15

Glu Arg Glu Glu Asp Ile Asp Leu His Leu Gly Asp Ile Leu Thr Val
            20                  25                  30

Asn Lys Gly Ser Leu Val Ala Leu Gly Phe Ser Asp Gly Gln Glu Ala
        35                  40                  45

Arg Pro Glu Glu Ile Gly Trp Leu Asn Gly Tyr Asn Glu Thr Thr Gly
    50                  55                  60

Glu Arg Gly Asp Phe Pro Gly Thr Tyr Val Glu Tyr Ile Gly Arg Lys
65                  70                  75                  80

Lys Ile Ser Pro Pro Thr Pro Lys Pro Arg Pro Pro Arg Pro Leu Pro
                85                  90                  95

Val Ala Pro Gly Ser Ser Lys Thr Glu Ala Asp Val Glu Gln Gln Ala
            100                 105                 110

Leu Thr Leu Pro Asp Leu Ala Glu Gln Phe Ala Pro Pro Asp Ile Ala
        115                 120                 125

Pro Pro Leu Leu Ile Lys Leu Val Glu Ala Ile Glu Lys Lys Gly Leu
    130                 135                 140

Glu Cys Ser Thr Leu Tyr Arg Thr Gln Ser Ser Ser Asn Leu Ala Glu
145                 150                 155                 160

Leu Arg Gln Leu Leu Asp Cys Asp Thr Pro Ser Val Asp Leu Glu Met
                165                 170                 175

Ile Asp Val His Val Leu Ala Asp Ala Phe Lys Arg Tyr Leu Leu Asp
            180                 185                 190

Leu Pro Asn Pro Val Ile Pro Ala Ala Val Tyr Ser Glu Met Ile Ser
        195                 200                 205

Leu Ala Pro Glu Val Gln Ser Ser Glu Glu Tyr Ile Gln Leu Leu Lys
    210                 215                 220

Lys Leu Ile Arg Ser Pro Ser Ile Pro His Gln Tyr Trp Leu Thr Leu
225                 230                 235                 240

Gln Tyr Leu Leu Lys His Phe Phe Lys Leu Ser Gln Thr Ser Ser Lys
                245                 250                 255

Asn Leu Leu Asn Ala Arg Val Leu Ser Glu Ile Phe Ser Pro Met Leu
            260                 265                 270

Phe Arg Phe Ser Ala Ala Ser Ser Asp Asn Thr Glu Asn Leu Ile Lys
        275                 280                 285

Val Ile Glu Ile Leu Ile Ser Thr Glu Trp Asn Glu Arg Gln Pro Ala
    290                 295                 300
```

```
Pro Ala Leu Pro Pro Lys Pro Pro Lys Pro Thr Thr Val Ala Asn Asn
305                 310                 315                 320

Gly Met Asn Asn Asn Met Ser Leu Gln Asp Ala Glu Trp Tyr Trp Gly
                325                 330                 335

Asp Ile Ser Arg Glu Glu Val Asn Glu Lys Leu Arg Asp Thr Ala Asp
            340                 345                 350

Gly Thr Phe Leu Val Arg Asp Ala Ser Thr Lys Met His Gly Asp Tyr
        355                 360                 365

Thr Leu Thr Leu Arg Lys Gly Gly Asn Asn Lys Leu Ile Lys Ile Phe
    370                 375                 380

His Arg Asp Gly Lys Tyr Gly Phe Ser Asp Pro Leu Thr Phe Ser Ser
385                 390                 395                 400

Val Val Glu Leu Ile Asn His Tyr Arg Asn Glu Ser Leu Ala Gln Tyr
                405                 410                 415

Asn Pro Lys Leu Asp Val Lys Leu Leu Tyr Pro Val Ser Lys Tyr Gln
            420                 425                 430

Gln Asp Gln Val Val Lys Glu Asp Asn Ile Glu Ala Val Gly Lys Lys
        435                 440                 445

Leu His Glu Tyr Asn Thr Gln Phe Gln Glu Lys Ser Arg Glu Tyr Asp
    450                 455                 460

Arg Leu Tyr Glu Glu Tyr Thr Arg Thr Ser Gln Glu Ile Gln Met Lys
465                 470                 475                 480

Arg Thr Ala Ile Glu Ala Phe Asn Glu Thr Ile Lys Ile Phe Glu Glu
                485                 490                 495

Gln Cys Gln Thr Gln Glu Arg Tyr Ser Lys Glu Tyr Ile Glu Lys Phe
            500                 505                 510

Lys Arg Glu Gly Asn Glu Lys Glu Ile Gln Arg Ile Met His Asn Tyr
        515                 520                 525

Asp Lys Leu Lys Ser Arg Ile Ser Glu Ile Ile Asp Ser Arg Arg Arg
    530                 535                 540

Leu Glu Glu Asp Leu Lys Lys Gln Ala Ala Glu Tyr Arg Glu Ile Asp
545                 550                 555                 560

Lys Arg Met Asn Ser Ile Lys Pro Asp Leu Ile Gln Leu Arg Lys Thr
                565                 570                 575

Arg Asp Gln Tyr Leu Met Trp Leu Thr Gln Lys Gly Val Arg Gln Lys
            580                 585                 590

Lys Leu Asn Glu Trp Leu Gly Asn Glu Asn Thr Glu Asp Gln Tyr Ser
        595                 600                 605

Leu Val Glu Asp Asp Glu Asp Leu Pro His His Asp Glu Lys Thr Trp
    610                 615                 620

Asn Val Gly Ser Ser Asn Arg Asn Lys Ala Glu Asn Leu Leu Arg Gly
625                 630                 635                 640

Lys Arg Asp Gly Thr Phe Leu Val Arg Glu Ser Ser Lys Gln Gly Cys
                645                 650                 655

Tyr Ala Cys Ser Val Val Val Asp Gly Glu Val Lys His Cys Val Ile
            660                 665                 670

Asn Lys Thr Ala Thr Gly Tyr Gly Phe Ala Glu Pro Tyr Asn Leu Tyr
        675                 680                 685

Ser Ser Leu Lys Glu Leu Val Leu His Tyr Gln His Thr Ser Leu Val
    690                 695                 700

Gln His Asn Asp Ser Leu Asn Val Thr Leu Ala Tyr Pro Val Tyr Ala
705                 710                 715                 720
```

Gln Gln Arg Arg

<210> SEQ ID NO 3
<211> LENGTH: 454
<212> TYPE: PRT
<213> ORGANISM: Homo sapiens

<400> SEQUENCE: 3

```
Met Tyr Asn Thr Val Trp Asn Met Glu Asp Leu Asp Leu Glu Tyr Ala
 1               5                  10                  15

Lys Thr Asp Ile Asn Cys Gly Thr Asp Leu Met Phe Tyr Ile Glu Met
            20                  25                  30

Asp Pro Pro Ala Leu Pro Pro Lys Pro Pro Lys Pro Thr Thr Val Ala
        35                  40                  45

Asn Asn Gly Met Asn Asn Asn Met Ser Leu Gln Asp Ala Glu Trp Tyr
    50                  55                  60

Trp Gly Asp Ile Ser Arg Glu Glu Val Asn Glu Lys Leu Arg Asp Thr
65                  70                  75                  80

Ala Asp Gly Thr Phe Leu Val Arg Asp Ala Ser Thr Lys Met His Gly
                85                  90                  95

Asp Tyr Thr Leu Thr Leu Arg Lys Gly Gly Asn Asn Lys Leu Ile Lys
            100                 105                 110

Ile Phe His Arg Asp Gly Lys Tyr Gly Phe Ser Asp Pro Leu Thr Phe
        115                 120                 125

Ser Ser Val Val Glu Leu Ile Asn His Tyr Arg Asn Glu Ser Leu Ala
    130                 135                 140

Gln Tyr Asn Pro Lys Leu Asp Val Lys Leu Leu Tyr Pro Val Ser Lys
145                 150                 155                 160

Tyr Gln Gln Asp Gln Val Val Lys Glu Asp Asn Ile Glu Ala Val Gly
                165                 170                 175

Lys Lys Leu His Glu Tyr Asn Thr Gln Phe Gln Glu Lys Ser Arg Glu
            180                 185                 190

Tyr Asp Arg Leu Tyr Glu Glu Tyr Thr Arg Thr Ser Gln Glu Ile Gln
        195                 200                 205

Met Lys Arg Thr Ala Ile Glu Ala Phe Asn Glu Thr Ile Lys Ile Phe
    210                 215                 220

Glu Glu Gln Cys Gln Thr Gln Glu Arg Tyr Ser Lys Glu Tyr Ile Glu
225                 230                 235                 240

Lys Phe Lys Arg Glu Gly Asn Glu Lys Glu Ile Gln Arg Ile Met His
                245                 250                 255

Asn Tyr Asp Lys Leu Lys Ser Arg Ile Ser Glu Ile Ile Asp Ser Arg
            260                 265                 270

Arg Arg Leu Glu Glu Asp Leu Lys Lys Gln Ala Ala Glu Tyr Arg Glu
        275                 280                 285

Ile Asp Lys Arg Met Asn Ser Ile Lys Pro Asp Leu Ile Gln Leu Arg
    290                 295                 300

Lys Thr Arg Asp Gln Tyr Leu Met Trp Leu Thr Gln Lys Gly Val Arg
305                 310                 315                 320

Gln Lys Lys Leu Asn Glu Trp Leu Gly Asn Glu Asn Thr Glu Asp Gln
                325                 330                 335

Tyr Ser Leu Val Glu Asp Asp Glu Asp Leu Pro His His Asp Glu Lys
            340                 345                 350

Thr Trp Asn Val Gly Ser Ser Asn Arg Asn Lys Ala Glu Asn Leu Leu
        355                 360                 365
```

```
Arg Gly Lys Arg Asp Gly Thr Phe Leu Val Arg Glu Ser Ser Lys Gln
    370                 375                 380

Gly Cys Tyr Ala Cys Ser Val Val Val Asp Gly Glu Val Lys His Cys
385                 390                 395                 400

Val Ile Asn Lys Thr Ala Thr Gly Tyr Gly Phe Ala Glu Pro Tyr Asn
                405                 410                 415

Leu Tyr Ser Ser Leu Lys Glu Leu Val Leu His Tyr Gln His Thr Ser
            420                 425                 430

Leu Val Gln His Asn Asp Ser Leu Asn Val Thr Leu Ala Tyr Pro Val
        435                 440                 445

Tyr Ala Gln Gln Arg Arg
    450


<210> SEQ ID NO 4
<211> LENGTH: 424
<212> TYPE: PRT
<213> ORGANISM: Homo sapiens

<400> SEQUENCE: 4

Met His Asn Leu Gln Thr Leu Pro Pro Lys Pro Pro Lys Pro Thr Thr
 1               5                  10                  15

Val Ala Asn Asn Gly Met Asn Asn Asn Met Ser Leu Gln Asp Ala Glu
            20                  25                  30

Trp Tyr Trp Gly Asp Ile Ser Arg Glu Glu Val Asn Glu Lys Leu Arg
        35                  40                  45

Asp Thr Ala Asp Gly Thr Phe Leu Val Arg Asp Ala Ser Thr Lys Met
    50                  55                  60

His Gly Asp Tyr Thr Leu Thr Leu Arg Lys Gly Gly Asn Asn Lys Leu
65                  70                  75                  80

Ile Lys Ile Phe His Arg Asp Gly Lys Tyr Gly Phe Ser Asp Pro Leu
                85                  90                  95

Thr Phe Ser Ser Val Val Glu Leu Ile Asn His Tyr Arg Asn Glu Ser
            100                 105                 110

Leu Ala Gln Tyr Asn Pro Lys Leu Asp Val Lys Leu Leu Tyr Pro Val
        115                 120                 125

Ser Lys Tyr Gln Gln Asp Gln Val Val Lys Glu Asp Asn Ile Glu Ala
    130                 135                 140

Val Gly Lys Lys Leu His Glu Tyr Asn Thr Gln Phe Gln Glu Lys Ser
145                 150                 155                 160

Arg Glu Tyr Asp Arg Leu Tyr Glu Glu Tyr Thr Arg Thr Ser Gln Glu
                165                 170                 175

Ile Gln Met Lys Arg Thr Ala Ile Glu Ala Phe Asn Glu Thr Ile Lys
            180                 185                 190

Ile Phe Glu Glu Gln Cys Gln Thr Gln Glu Arg Tyr Ser Lys Glu Tyr
        195                 200                 205

Ile Glu Lys Phe Lys Arg Glu Gly Asn Glu Lys Glu Ile Gln Arg Ile
    210                 215                 220

Met His Asn Tyr Asp Lys Leu Lys Ser Arg Ile Ser Glu Ile Ile Asp
225                 230                 235                 240

Ser Arg Arg Arg Leu Glu Glu Asp Leu Lys Lys Gln Ala Ala Glu Tyr
                245                 250                 255

Arg Glu Ile Asp Lys Arg Met Asn Ser Ile Lys Pro Asp Leu Ile Gln
            260                 265                 270

Leu Arg Lys Thr Arg Asp Gln Tyr Leu Met Trp Leu Thr Gln Lys Gly
        275                 280                 285
```

```
Val Arg Gln Lys Lys Leu Asn Glu Trp Leu Gly Asn Glu Asn Thr Glu
    290                 295                 300

Asp Gln Tyr Ser Leu Val Glu Asp Asp Glu Asp Leu Pro His His Asp
305                 310                 315                 320

Glu Lys Thr Trp Asn Val Gly Ser Ser Asn Arg Asn Lys Ala Glu Asn
                325                 330                 335

Leu Leu Arg Gly Lys Arg Asp Gly Thr Phe Leu Val Arg Glu Ser Ser
            340                 345                 350

Lys Gln Gly Cys Tyr Ala Cys Ser Val Val Val Asp Gly Glu Val Lys
        355                 360                 365

His Cys Val Ile Asn Lys Thr Ala Thr Gly Tyr Gly Phe Ala Glu Pro
    370                 375                 380

Tyr Asn Leu Tyr Ser Ser Leu Lys Glu Leu Val Leu His Tyr Gln His
385                 390                 395                 400

Thr Ser Leu Val Gln His Asn Asp Ser Leu Asn Val Thr Leu Ala Tyr
                405                 410                 415

Pro Val Tyr Ala Gln Gln Arg Arg
            420


<210> SEQ ID NO 5
<211> LENGTH: 1212
<212> TYPE: DNA
<213> ORGANISM: Homo sapiens

<400> SEQUENCE: 5

atgacagcca tcatcaaaga gatcgttagc agaaacaaaa ggagatatca agaggatgga      60

ttcgacttag acttgaccta tatttatcca aacattattg ctatgggatt tcctgcagaa     120

agacttgaag gcgtatacag gaacaatatt gatgatgtag taaggttttt ggattcaaag     180

cataaaaacc attacaagat atacaatctt tgtgctgaaa gacattatga caccgccaaa     240

tttaattgca gagttgcaca atatcctttt gaagaccata acccaccaca gctagaactt     300

atcaaaccct tttgtgaaga tcttgaccaa tggctaagtg aagatgacaa tcatgttgca     360

gcaattcact gtaaagctgg aaagggacga actggtgtaa tgatatgtgc atatttatta     420

catcggggca aatttttaaa ggcacaagag gccctagatt tctatgggga agtaaggacc     480

agagacaaaa agggagtaac tattcccagt cagaggcgct atgtgtatta ttatagctac     540

ctgttaaaga atcatctgga ttatagacca gtggcactgt tgtttcacaa gatgatgttt     600

gaaactattc caatgttcag tggcggaact tgcaatcctc agtttgtggt ctgccagcta     660

aaggtgaaga tatattcctc caattcagga cccacacgac gggaagacaa gttcatgtac     720

tttgagttcc ctcagccgtt acctgtgtgt ggtgatatca aagtagagtt cttccacaaa     780

cagaacaaga tgctaaaaaa ggacaaaatg tttcactttt gggtaaatac attcttcata     840

ccaggaccag aggaaacctc agaaaaagta gaaaatggaa gtctatgtga tcaagaaatc     900

gatagcattt gcagtataga gcgtgcagat aatgacaagg aatatctagt acttacttta     960

acaaaaaatg atcttgacaa agcaaataaa gacaaagcca accgatactt ttctccaaat    1020

tttaaggtga agctgtactt cacaaaaaca gtagaggagc cgtcaaatcc agaggctagc    1080

agttcaactt ctgtaacacc agatgttagt gacaatgaac ctgatcatta tagatattct    1140

gacaccactg actctgatcc agagaatgaa ccttttgatg aagatcagca tacacaaatt    1200

acaaaagtct ga                                                        1212
```

```
<210> SEQ ID NO 6
<211> LENGTH: 368
<212> TYPE: PRT
<213> ORGANISM: Homo sapiens

<400> SEQUENCE: 6

Val Leu Val Leu Leu Asn Pro Arg Gly Gly Lys Gly Lys Ala Leu Gln
 1               5                  10                  15

Leu Phe Arg Ser His Val Gln Pro Leu Leu Ala Glu Ala Glu Ile Ser
            20                  25                  30

Phe Thr Leu Met Leu Thr Glu Arg Arg Asn His Ala Arg Glu Leu Val
        35                  40                  45

Arg Ser Glu Glu Leu Gly Arg Trp Asp Ala Leu Val Val Met Ser Gly
    50                  55                  60

Asp Gly Leu Met His Glu Val Val Asn Gly Leu Met Glu Arg Pro Asp
65                  70                  75                  80

Trp Glu Thr Ala Ile Gln Lys Pro Leu Cys Ser Leu Pro Ala Gly Ser
                85                  90                  95

Gly Asn Ala Leu Ala Ala Ser Leu Asn His Tyr Ala Gly Tyr Glu Gln
            100                 105                 110

Val Thr Asn Glu Asp Leu Leu Thr Asn Cys Thr Leu Leu Leu Cys Arg
        115                 120                 125

Arg Leu Leu Ser Pro Met Asn Leu Leu Ser Leu His Thr Ala Ser Gly
    130                 135                 140

Leu Arg Leu Phe Ser Val Leu Ser Leu Ala Trp Gly Phe Ile Ala Asp
145                 150                 155                 160

Val Asp Leu Glu Ser Glu Lys Tyr Arg Arg Leu Gly Glu Met Arg Phe
                165                 170                 175

Thr Leu Gly Thr Phe Leu Arg Leu Ala Ala Leu Arg Thr Tyr Arg Gly
            180                 185                 190

Arg Leu Ala Tyr Leu Pro Val Gly Arg Val Gly Ser Lys Thr Pro Ala
        195                 200                 205

Ser Pro Val Val Val Gln Gln Gly Pro Val Asp Ala His Leu Val Pro
    210                 215                 220

Leu Glu Glu Pro Val Pro Ser His Trp Thr Val Val Pro Asp Glu Asp
225                 230                 235                 240

Phe Val Leu Val Leu Ala Leu Leu His Ser His Leu Gly Ser Glu Met
                245                 250                 255

Phe Ala Ala Pro Met Gly Arg Cys Ala Ala Gly Val Met His Leu Phe
            260                 265                 270

Tyr Val Arg Ala Gly Val Ser Arg Ala Met Leu Leu Arg Leu Phe Leu
        275                 280                 285

Ala Met Glu Lys Gly Arg His Met Glu Tyr Glu Cys Pro Tyr Leu Val
    290                 295                 300

Tyr Val Pro Val Val Ala Phe Arg Leu Glu Pro Lys Asp Gly Lys Gly
305                 310                 315                 320

Val Phe Ala Val Asp Gly Glu Leu Met Val Ser Glu Ala Val Gln Gly
                325                 330                 335

Gln Val His Pro Asn Tyr Phe Trp Met Val Ser Gly Cys Val Glu Pro
            340                 345                 350

Pro Pro Ser Trp Lys Pro Gln Gln Met Pro Pro Pro Glu Glu Pro Leu
        355                 360                 365
```

USE OF UNSATURATED SPHINGOSINE COMPOUNDS AS CHEMOTHERAPEUTIC AGENTS FOR THE TREATMENT OF CANCER

CROSS-REFERENCE TO RELATED APPLICATION

This application claims the benefit under 35 U.S.C. §119 (e) of U.S. Provisional Patent Application No. 61/013,230 filed Dec. 12, 2007, which is incorporated herein by reference in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 200116.409PC_SEQUENCE_LISTING.txt. The text file is 22 KB, was created on Dec. 12, 2008, and is being submitted electronically via EFS-Web, concurrent with the filing of the specification.

FIELD OF THE INVENTION

The present invention is directed to unsaturated sphingosine compounds which are useful as therapeutic agents for the treatment of cancer and for the treatment of other diseases including diabetes and infection with intracellular bacteria. This invention is also directed to methods of using the compounds and pharmaceutical compositions comprising the compounds in treating these diseases.

BACKGROUND OF THE INVENTION

Colon cancer is the second most common cancer of men and women and the third leading cause of cancer mortality (1). It is estimated that $8.4 billion per year is spent caring for patients with this disease in the United States. Identifying chemopreventive agents and dietary constituents that facilitate the turnover of intestinal epithelial cells containing DNA damage and/or that block the progression of premalignant intestinal tissue to frank carcinoma could have a significant impact on public health. Similarly, novel agents that could be used to treat the 50% of colon cancer patients suffering from advanced or refractory disease are needed.

In mammalian cells, sphingolipid structure, composition and metabolism have been well characterized (2, 3). Knowledge of sphingolipid structure has facilitated in-depth analyses of the contribution of sphingolipids to membrane organization and their function in signal transduction events and normal physiology. Such studies have defined an important role for higher order sphingolipids in the formation of membrane subdomains (lipid rafts) wherein growth factor signaling and recruitment occur (4-7), and sphingolipid metabolites such as sphingosine, ceramide, sphingosine-1-phosphate and ceramide-1-phosphate have been shown to participate in signaling pathways regulating the key processes of cellular proliferation, migration, stress responses, apoptosis, angiogenesis and immune cell trafficking (8-13). Dysregulation of sphingolipid metabolism has been implicated as a contributing factor in carcinogenesis, cancer progression and drug resistance (14, 15). Recently it was shown that sphingolipid metabolism is disrupted in the mucosal epithelium during intestinal tumorigenesis and contributes to tumor progression (16, 17). In contrast, the accumulation of endogenous growth-inhibitory sphingolipids such as ceramide is recognized as a mechanism of action of some cytotoxic agents (18). The presence of the $C_{4-5}$ double bond in the sphingoid base is believed to confer cytotoxic biological activity, as dihydrosphingosine and dihydroceramide are not cytotoxic in most cells. Strategies to enhance ceramide production and accumulation in malignant cells have been considered a novel approach for cancer therapy (19-21).

Sphingolipids are conserved throughout evolution and as such are enriched in many constituents of the human diet, including meat, dairy and soy products (22-24). Normal consumption of sphingolipids is estimated to be about 0.3-0.4 grams per day. Dietary sphingolipids are metabolized to ceramide and ultimately to sphingosine by brush border enzymes in the gut epithelium (25). Sphingosine (but not ceramide) is taken up by intestinal epithelial cells, where it inhibits growth (26, 27). Thus, intestinal epithelial cells are exposed to sphingolipids from both intracellular synthesis and from the diet. Dietary sphingolipids have been shown to be cytotoxic to colon cancer cells in vitro, and consumption of sphingolipids suppresses colon carcinogenesis in rodents (26-32).

Studies have been conducted on the physiological roles of sphingolipids in the genetically tractable organism, *Drosophila melanogaster*. In this species, tight regulation of sphingolipid levels is required for proper development, reproduction and the maintenance of tissue integrity, as demonstrated by the severe phenotypes observed in mutants with disrupted sphingolipid metabolism (33-37). However, a clear understanding of the role of sphingolipid metabolism and, in particular, the mechanisms by which sphingolipid metabolites influence physiological processes in this organism, has been hampered by an incomplete knowledge of the chemical structure of endogenous *Drosophila* sphingolipids and their metabolic products.

The AKT/PI3 kinase pathway has emerged as a central signaling node responsible for adjusting the metabolic and biosynthetic operations of the cell in response to changing nutrient and environmental conditions (Woodgett, J. R. "Recent advances in the protein kinase B signaling pathway." Curr Opin Cell Biol 17(2): 150-157, 2005.; Ruggero, D. and Sonenberg, N., "The Akt of translational control." Oncogene 24(50): 7426-7434, 2005). Activation of the pathway facilitates cell cycle progression, inhibits apoptosis, and enhances nutrient uptake and protein synthesis, leading to increased cell growth and survival. The $PI_3$ kinase/AKT pathway is normally activated by tyrosine kinase receptor ligation, which activates class I phosphoinositol-3 kinase ($PI_3K$). $PI_3K$ phosphorylates phosphatidylinositol-4,5-bisphosphate ($PIP_2$), generating phosphatidylinositol-3,4,5-trlsphosphate ($PIP_3$), which facilitates membrane recruitment and activation of the protein kinase AKT by virtue of the latter's lipophilic pleckstrin homology domain (PHD). Activated AKT subsequently phosphorylates downstream targets controlling cell growth and survival. The tumor suppressor PTEN antagonizes AKT signaling by catalyzing the dephosphorylation of $PIP_3$ to $PIP_2$ (Ramaswamy, S. et al. Proc Natl Acad Sci USA 96: 2110-2115, 1999). Activating mutations in the $PI_3K$/AKT pathway are commonly found in human malignancies, including colon cancer (Tohma. Y., et al., J Neuropathol Exp Neurol 57(7): 684-689, 1998; Carpten, J. D., et al., Nature 448(7152): 439-444, 2007; Vivanco, I. and Sawyers, C. L., Nat Rev Cancer 2(7): 489-501, 2002).

Akt is a central player in the regulation of cell metabolism, cell survival, motility, transcription, and cell cycle progression (see, e.g., Fayard et al., *Journal of Cell Science.* 2005 118:5675-78). The Akt subfamily comprises three mammalian isoforms, Akt1, Akt2, and Akt3, which are products of distinct genes and share a conserved structure that includes three functional domains: an N-terminal pleckstrin homology (PH) domain, a central kinase domain, and a C-terminal regulatory domain.

Akt is a downstream component in the phosphoinositide 3-kinase (PI3K) pathway. Akt is activated by numerous upstream PI3K regulatory components, including, for example, receptor tyrosine kinases, integrins, B and T cell receptors, cytokine receptors, G-protein coupled receptors, and other stimuli that induce the production of lipid phosphatidylinositol 3,4,5 triphosphates (PtdIns(3,4,5)P3) through PI3K. Certain studies report as well that Akt can be activated in a PI3K independent manner (see, e.g., Vanhaesebroeck and Alessi *Blochem. J.* 2000, 346:561-576).

PtdIns(3,4,5) triphosphates serve as plasma membrane docking sites for both Akt and its upstream activator PI3K-dependent kinase-1 (PDK1) by interacting with their PH domains. Akt interaction with PtdIns-3,4,5-P3 promotes Akt translocation from the cytoplasm to the plasma membrane, where Akt undergoes phosphorylation at two sites: Thr308 in the activation loop and Ser473 in the carboxy-terminal tail. PDK-1 phosphorylates Akt at Thr308, but the Ser473 kinase remains unknown. Phosphorylated Akt translocates from the plasma membrane to the cytosol or the nucleus, where it acts on its downstream substrates.

When properly regulated, activated Akt eventually undergoes dephosphorylation by phosphatases and returns to the inactive state. For example, the tumor suppressor phosphatase and tensin homology (PTEN) and the SH2-domain containing inositol polyphosphate 5-phosphatase (SHIP) Indirectly inhibit Akt activity by regulating PtdIns(3,4,5)P3. In addition, protein phosphatase 2A (PP2A) and PH domain leucine-repeat protein phospatase (PHLPPα) directly dephosphorylate Akt at Thr308 and/or Ser473.

Akt mediates many of the downstream events regulated by PI3K. Of particular interest to cancer therapy. Akt regulates the activity of numerous substrates associated with cell proliferation, including, for example, p27. Chk1, Yes-associated protein (YAP), p53, murine double minute (Mdm 2). IκB kinase (IKK), Par-4, caspase-9, the family of forkhead box (Fox) transcription factors, p70 S6 kinase pathway through mammalian target of rapamycin (mTor) or Raf1, Bad, glycogen synthase kinase-3 a/β (GSK-3a/β), glycogen synthase, the androgen receptor, cyclin D1, and p21. Most of these substrates comprise the minimal consensus sequence RxTxx (S/T), where x is any amino acid and S/T is the phosphorylation site. Generally, Akt downstream activity promotes cell survival, for example, by either positively regulating cellular proliferation pathways or by preventing apoptosis. Although constitutive Akt action alone is believed to be insufficient for tumorigenesis, Akt over-activity is implicated in many types of cancer.

Also relevant to cancer therapy, Akt plays a dual role in cell motility, enhancing motility in certain cells such as fibroblasts, and inhibiting motility in other cells such as epithelial cells. For example, Akt expression in fibrosarcoma and pancreatic cancer cells increases their invasion through Matrigel, and Akt expression can promote epithelial-mesenchymal transition, a process associated with tumor progression to invasive and metastatic carcinoma. In contrast, as one example of Akt inhibition of motility, the Akt1 isoform in particular limits the invasive migration breast cancer cells, most likely by stabilizing Mdm2, and thus accelerating the degradation of the NFAT transcriptional regulator (see, e.g., Toker et al, *Cancer Res.* 2006, 66:3963-66).

Akt is also a regulator of insulin signaling and glucose metabolism, and its activation through the PI3K pathway is essential for most insulin-Induced glucose and lipid metabolism such as glucose uptake, glycogen synthesis, suppression of glucose output, triglyceride synthesis, as well as insulin-induced mitogenesis (see, e.g., Asano et al., *Biol Pharm Bull.* 2007, 30:1610-1616). For example, GLUT-4 is the primary glucose transporter in skeletal muscle cells and adipocytes, and plays a role in insulin-mediated glucose disposal. Insulin activates Akt through the PI3K pathway, causing GLUT-4 translocation to the plasma membrane and an increase in basal glucose transport. Akt effects glucose metabolism in other ways, as PI3K and Akt inhibitors inhibit not only insulin induced glucose uptake, but inhibit glycogen synthesis as well.

Studies also implicate Akt in intracellular bacterial growth (see, e.g., Kuijl et al., *Nature* 2007, 450:725-730). The *Salmonella typhimurium* effector SopB activates Akt1, which promotes bacterial intracellular survival by controlling actin dynamics through PAK4 and by controlling phagosome-lysosome fusion through the AS160-RAB14 pathway. Akt1 inhibitors may counteract the bacterial manipulation of host signaling processes, controlling the intracellular growth of bacteria such as *S. typhimurium* and *Mycobacterium luberculosis.*

The Wnt signaling pathway involves a large number of proteins that can regulate the production of Wnt signaling molecules, their interactions with receptors on target cells and the physiological responses of target cells that result from the exposure of cells to the extracellular Wnt ligands. The canonical Wnt pathway involves a series of cellular events that occur when Wnt proteins bind to cell-surface receptors of the Frizzled family, causing the receptors to activate Dishevelled family proteins and ultimately resulting in a change in the amount of β-catenin that reaches the nucleus. Dishevelled (DSH) is a key component of a membrane-associated Wnt receptor complex which, when activated by Wnt binding, inhibits a second complex of proteins that includes axin, GSK-3, and the protein APC. The axin/GSK-3/APC complex normally promotes the proteolytic degradation of the β-catenin intracellular signaling molecule. After this "β-catenin destruction complex" is inhibited, a pool of cytoplasmic β-catenin stabilizes, and some β-catenin is able to enter the nucleus and interact with TCF/LEF family transcription factors to promote specific gene expression (see Gordon M D and Nusse R. J Biol. Chem. 2006 Aug. 11; 281(32):22429-33: Hausmann G, et al. Nat Rev Mol Cell Biol. 2007 April; 8(4):331-6; Clevers, H, Cell 2006, 469 (2006); Nusse, R. Science 316, 988 (2007)).

Activation of the Wnt signaling pathway leads to β-catenin migration into the nucleus, where it interacts with and converts the T-cell factor (TCF) transcription factor from a repressor to an activator, inducing target genes that mediate proliferation, adhesion and migratory responses (Fuchs, S. Y. et al. Cell Cycle 4(11): 1522-1539, 2005). Mutations in the Adenomatous Polyposis Coli (APC) gene, a negative regulator of the Wnt pathway, are responsible for intestinal polyposis in $Apc^{Min/+}$ (also called Min) mice and colon cancer in the human disease Familial Adenomatous Polyposis (FAP) (Kucherlapati, R., et al. Semin Cancer Biol 11(3): 219-225., 2001; Sansom, O. J., et al., Genes Dev 18(12): 1385-1390, 2004). A high incidence of mutations in APC or other components of the Wnt pathway has been identified in sporadic colon cancer, indicating the central role that Wnt signaling plays in intestinal tumorigenesis (Sancho, E., et al., Annu Rev Cell Dev Biol 20: 695-723, 2004). In fact, activation of the Wnt pathway is considered one of the first molecular changes contributing to colon carcinogenesis (Kinzler, K. W. and Vogelstein, B. Cell 87(2): 159-170., 1996).

Accordingly, there exists a need for improved understanding of sphingolipid pathways and intermediates and of their role in influencing signaling pathways such as the AKT/PI3 kinase pathway and the Wnt signalling pathway, and their roles in cellular physiology, including molecular mechanisms of cancer. Disclosed herein are compositions and methods that address this need by providing unsaturated sphingosine compounds that are useful in treating cancer and other diseases, and which offer other related advantages.

SUMMARY OF THE INVENTION

This invention is directed in certain embodiments to unsaturated sphingosine compounds, methods of using such compounds in treating cancer and other diseases as described herein, and pharmaceutical compositions comprising such compounds.

Accordingly, in one embodiment this invention is directed to a method of treating a cancer in a mammal, wherein the method comprises administering to the mammal a therapeutically effective amount of a compound of formula (I):

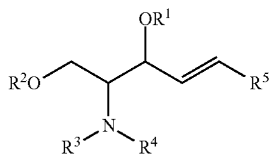

wherein:

$R^1$ and $R^2$ are independently selected from the group consisting of hydrogen, alkyl, optionally substituted cycloalkyl, optionally substituted aralkyl, optionally substituted heterocyclylalkyl, optionally substituted heteroarylalkyl, —C(O)$R^6$, —C(O)N($R^6$)$R^7$, —S(O)$_t$$R^6$ (where t is 1 or 2), —S(O)$_2$N($R^6$)$R^7$, —P(O)$_2$O$R^6$ and —C(S)$R^6$;

$R^3$ and $R^4$ are independently selected from the group consisting of hydrogen, alkyl, optionally substituted aralkyl, —C(O)$R^6$, and —C(O)O$R^6$, or $R^3$ and $R^4$, together with the common nitrogen to which they are both attached, form an optionally substituted N-heterocyclyl or an optionally substituted N-heteroaryl:

$R^5$ is selected from the group consisting of —C($R^9$)=C($R^9$)—[C($R^{10}$)]$_m$—$R^8$—[C($R^{10}$)]$_n$—$CH_3$ where m+n is 6 to 10, —[C($R^{10}$)]$_2$—C($R^9$)=C($R^9$)—[C($R^{10}$)]$_q$—$R^8$—[C($R^{10}$)]$_r$—$CH_3$ where q+r is 4 to 8, and —C($R^9$)=C($R^9$)—C($R^9$)=C($R^9$)—[C($R^{10}$)]$_u$—$R^8$—[C($R^{10}$)]$_v$—$CH_3$ where u+v is 4 to 8;

each $R^6$ and $R^7$ is independently selected from the group consisting of hydrogen, alkyl, alkenyl, alkynyl, optionally substituted cycloalkyl, optionally substituted cycloalkylalkyl, optionally substituted cycloalkylalkenyl, optionally substituted cycloalkylalkynyl, optionally substituted aryl, optionally substituted aralkyl, optionally substituted aralkenyl, optionally substituted aralkynyl, optionally substituted heterocyclyl, optionally substituted heterocycylalkyl, optionally substituted heterocyclylalkenyl, optionally substituted heterocycylalkynyl, optionally substituted heteroaryl, optionally substituted heteroarylalkyl, optionally substituted heteroarylalkenyl, and optionally substituted heteroarylalkynyl;

each $R^8$ is selected from the group consisting of a direct bond, an optionally substituted arylene and an optionally substituted heteroarylene;

each $R^9$ is independently hydrogen or alkyl;

each $R^{10}$ is independently selected from the group consisting of hydrogen, halo, haloalkyl, alkyl, alkenyl, alkynyl, —$R^{11}$—O$R^6$, —$R^{11}$—OC(O)$R^6$, —$R^{11}$—S(O)$_p$$R^6$ (where p is 0, 1 or 2), —$R^{11}$—C(O)$R^6$, —$R^{11}$—C(O)O$R^6$, —$R^{11}$—N($R^6$)$R^7$, and —$R^{11}$—C(O)N($R^6$)$R^7$; and each $R^{11}$ is independently selected from a direct bond, an optionally substituted straight or branched alkylene chain, an optionally substituted straight or branched alkenylene chain and an optionally substituted straight or branched alkynylene chain;

as an isolated stereoisomer or mixture thereof, or a pharmaceutically acceptable salt thereof.

In another embodiment, this invention is directed to pharmaceutical compositions comprising a pharmaceutically acceptable excipient and a therapeutically effective amount of a compound of formula (I), as described above, as an isolated stereoisomer or mixture thereof, or a pharmaceutically acceptable salt thereof.

In another embodiment, this invention is directed to methods of treating cancer in a mammal, wherein the methods comprise administering to the mammal in need thereof a therapeutically effective amount of a pharmaceutical composition comprising a pharmaceutically acceptable excipient and a compound of formula (I), as described above, as an isolated stereoisomer or mixture thereof, or a pharmaceutically acceptable salt thereof.

In another embodiment, this invention provides assays to determine the effectiveness of a compound of the invention in treating cancer.

Another embodiment of the invention provides a method for altering the activity of a component of the AKT/PI3 kinase signaling pathway in a mammal wherein the method comprises administering to the mammal a compound of formula (I), as described above, as an isolated stereoisomer or mixture thereof, or a pharmaceutically acceptable salt thereof.

In another embodiment of the invention provides a method for inhibiting sphingosine kinase activity in a mammal wherein the method comprises administering to the mammal a compound of formula (I), as described above, as an Isolated stereoisomer or mixture thereof, or a pharmaceutically acceptable salt thereof.

Yet another embodiment of the invention provides a method for inhibiting the Wnt signaling pathway in a mammal wherein the method comprises administering to the mammal a compound of formula (I), as described above, as an isolated stereoisomer or mixture thereof, or a pharmaceutically acceptable salt thereof.

In another embodiment of the invention provides a method for inducing apoptosis in a cell, wherein the method comprises contacting the cell with a compound of formula (I), as described above, as an isolated stereoisomer or mixture thereof, or a pharmaceutically acceptable salt thereof. In certain embodiments, this is an in vivo method whereby the compound is administered to a mammal. In another embodiment, this method may be an ex vivo or in vitro method.

In another embodiment of the invention provides a method for inducing autophagy in a cell wherein the method comprises contacting the cell with a compound of formula (I), as described above, as an isolated stereoisomer or mixture thereof, or a pharmaceutically acceptable salt thereof. In certain embodiments, this method is an in vivo method whereby the compound is administered to a mammal. In another embodiment, this method may be an ex vivo or in vitro method.

These and other aspects of the invention will be evident upon reference to the following detailed description and attached drawings.

All of the U.S. patents, U.S. patent application publications. U.S. patent applications, foreign patents, foreign patent applications and non-patent publications referred to in this specification and/or listed in the Application Data Sheet, are incorporated herein by reference in their entirety, as if each was incorporated individually. Aspects of the invention can be modified, if necessary, to employ concepts of the various patents, applications and publications to provide yet further embodiments of the invention.

DETAILED DESCRIPTION OF THE INVENTION

Definitions

Figure 1:
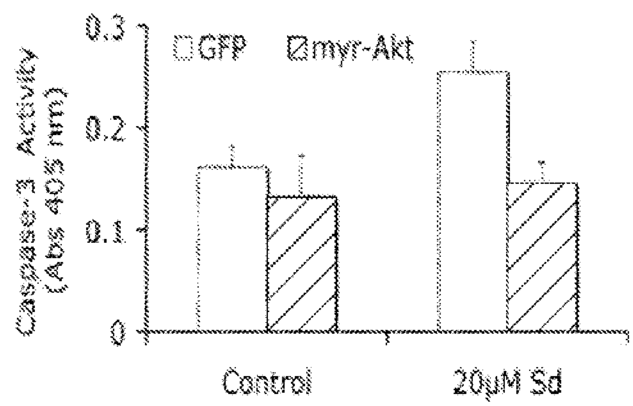
FIG. 1 is a bar graph showing caspase-3 activity in HT29 cells in the presence or absence of sphingadienes. HT29 cells were transfected with myr-Akt cDNA or vector control using FuGene HT reagent (Roche); after 36 hours, cells were treated with 10 μM sphingadiene (SD) for 24 hours and analyzed for apoptosis by caspase-3 activity.

As used in the specification and appended claims, unless specified to the contrary, the following terms have the meaning indicated:

"Alkyl" refers to a straight or branched hydrocarbon chain radical consisting solely of carbon and hydrogen atoms, containing no unsaturation, having from one to fourteen carbon atoms, preferably one to eight carbon atoms or one to six carbon atoms ("lower alkyl"), and which is attached to the rest of the molecule by a single bond, for example, methyl, ethyl, n-propyl. 1-methylethyl (isopropyl), n-butyl, n-pentyl, 1,1-dimethylethyl (tert-butyl), 3-methylhexyl, 2-methylhexyl, and the like. Unless stated otherwise specifically in the specification, an alkyl radical may be optionally substituted by one or more of the following substituents: halo, cyano, nitro, oxo, thioxo, trimethylsilanyl, —$OR^{20}$, —OC(O)—$R^{20}$, —$N(R^{20})_2$, —C(O)$R^{20}$, —C(O)O$R^{20}$, —C(O)$N(R^{20})_2$, —$N(R^{20})$C(O)O$R^{20}$, —$N(R^{20})$C(O)$R^{20}$, —$N(R^{20})S(O)_tR^{20}$ (where t is 1 or 2), —$S(O)_tOR^{20}$ (where t is 1 or 2), —$S(O)_pR^{20}$ (where p is 0, 1, or 2), and —$S(O)_tN(R^{20})_2$ (where t is 1 or 2) where each $R^{20}$ is independently hydrogen, alkyl, haloalkyl, cycloalkyl, cycloalkylalkyl, aryl, aralkyl, heterocyclyl, heterocylylalkyl, heteroaryl, or heteroarylalkyl.

"Alkenyl" refers to a straight or branched hydrocarbon chain radical consisting solely of carbon and hydrogen atoms, containing at least one double bond, having from two to twelve carbon atoms, preferably one to eight carbon atoms and which is attached to the rest of the molecule by a single bond, for example, ethenyl, prop-1-enyl, but-1-enyl, pent-1-enyl, penta-1,4-dienyl, and the like. Unless stated otherwise specifically in the specification, an alkenyl radical may be optionally substituted by one or more of the following substituents: halo, cyano, nitro, oxo, thioxo, trimethysilanyl, —$OR^{20}$, —OC(O)—$R^{20}$, —$N(R^{20})_2$, —C(O)$R^{20}$, —C(O)O$R^{20}$, —C(O)$N(R^{20})_2$, —$N(R^{20})$C(O)O$R^{20}$, —$N(R^{20})$C(O)$R^{20}$, —$N(R^{20})S(O)_tR^{20}$ (where t is 1 or 2), —$S(O)_tOR^{20}$ (where t is 1 or 2), —$S(O)_pR^{20}$ (where p is 0, 1, or 2), and —$S(O)_tN(R^{20})_2$ (where t is 1 or 2) where each $R^{20}$ is independently hydrogen, alkyl, haloalkyl, cycloalkyl, cycloalkylalkyl, aryl, aralkyl, heterocyclyl, heterocylylalkyl, heteroaryl, or heteroarylalkyl.

"Alkynyl" refers to a straight or branched hydrocarbon chain radical consisting solely of carbon and hydrogen atoms, containing at least one triple bond, optionally containing at least one double bond, having from two to twelve carbon atoms, preferably one to eight carbon atoms and which is attached to the rest of the molecule by a single bond, for example, ethynyl, propynyl, butynyl, pentynyl, hexynyl, and the like. Unless stated otherwise specifically in the specification, an alkynyl radical may be optionally substituted by one or more of the following substituents: halo, cyano, nitro, oxo, thioxo, trimethylsilanyl, —$OR^{20}$, —OC(O)—$R^{20}$, —$N(R^{20})_2$, —C(O)$R^{20}$, —C(O)O$R^{20}$, —C(O)$N(R^{20})_2$, —$N(R^{20})$C(O)O$R^{20}$, —$N(R^{20})$C(O)$R^{20}$, —$N(R^{20})S(O)_tR^{20}$ (where t is 1 or 2). —$S(O)_tOR^{20}$ (where t is 1 or 2), —$S(O)_pR^{20}$ (where p is 0, 1 or 2), and —$S(O)_tN(R^{20})_2$ (where t is 1 or 2) where each $R^{20}$ is independently hydrogen, alkyl, haloalkyl, cycloalkyl, cycloalkylalkyl, aryl, aralkyl, heterocyclyl, heterocylylalkyl, heteroaryl, or heteroarylalkyl.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group can be through one carbon in the alkylene chain or through any two carbons within the chain. Unless stated otherwise specifically in the specification, an alkylene chain may be optionally substituted by one or more of the following substituents: halo, cyano, nitro, aryl, cycloalkyl, heterocyclyl, heteroaryl, oxo, thioxo, trimethylsilanyl, —$OR^{20}$, —OC(O)—$R^{20}$. —$N(R^{20})_2$, —C(O)$R^{20}$, —C(O)$OR^{20}$, —C(O)$N(R^{20})_2$, —$N(R^{20})$C(O)$OR^{20}$, —$N(R^{20})$C(O)$R^{20}$, —$N(R^{20})S(O)_tR^{20}$ (where t is 1 or 2), —$S(O)_tOR^{20}$ (where t is 1 or 2), —$S(O)_pR^{20}$ (where p is 0, 1, or 2), and —$S(O)_tN(R^{20})_2$ (where t is 1 or 2) where each $R^{20}$ is independently hydrogen, alkyl, haloalkyl, cycloalkyl, cycloalkylalkyl, aryl, aralkyl, heterocyclyl, heterocylylalkyl, heteroaryl, or heteroarylalkyl.

"Alkenylene" or "alkenylene chain" refers to a straight or branched divalent hydrocarbon chain linking the rest of the molecule to a radical group, consisting solely of carbon and hydrogen, containing at least one double bond and having from two to twelve carbon atoms, for example, ethenylene, propenylene, n-butenylene, and the like. The alkenylene chain is attached to the rest of the molecule through a double bond or a single bond and to the radical group through a double bond or a single bond. The points of attachment of the alkenylene chain to the rest of the molecule and to the radical group can be through one carbon or any two carbons within the chain. Unless stated otherwise specifically in the specification, an alkenylene chain may be optionally substituted by one or more of the following substituents: halo, cyano, nitro, aryl, cycloalkyl, heterocyclyl, heteroaryl, oxo, thioxo, trimethylsilanyl, —$OR^{20}$, —OC(O)—$R^{20}$, —$N(R^{20})_2$, —C(O)$R^{20}$, —C(O)$OR^{20}$, —C(O)$N(R^{20})_2$, —$N(R^{20})$C(O)$OR^{20}$, —$N(R^{20})$C(O)$R^{20}$, —$N(R^{20})S(O)_tR^{20}$ (where t is 1 or 2), —$S(O)_tOR^{20}$ (where t is 1 or 2), —$S(O)_pR^{20}$ (where p is 0, 1, or 2), and —$S(O)_tN(R^{20})_2$ (where t is 1 or 2) where each R is independently hydrogen, alkyl, haloalkyl, cycloalkyl, cycloalkylalkyl, aryl, aralkyl, heterocyclyl, heterocylylalkyl, heteroaryl, or heteroarylalkyl.

"Alkynylene" or "alkynylene chain" refers to a straight or branched divalent hydrocarbon chain linking the rest of the molecule to a radical group, consisting solely of carbon and hydrogen, containing at least one triple bond and having from two to twelve carbon atoms, for example, propynylene, n-butynylene, and the like. The alkynylene chain is attached to the rest of the molecule through a single bond and to the radical group through a double bond or a single bond. The points of attachment of the alkynylene chain to the rest of the molecule and to the radical group can be through one carbon or any two carbons within the chain. Unless stated otherwise specifically in the specification, an alkynylene chain may be optionally substituted by one or more of the following substituents: alkyl, alkenyl, halo, haloalkenyl, cyano, nitro, aryl, cycloalkyl, heterocyclyl, heteroaryl, oxo, thioxo, trimethylsilanyl, —$OR^{20}$, —OC(O)—$R^{20}$, —$N(R^{20})_2$, —C(O)$R^{20}$, —C(O)$OR^{20}$, —C(O)$N(R^{20})_2$, —$N(R^{20})$C(O)$OR^{20}$, —$N(R^{20})$C(O)$R^{20}$, —$N(R^{20})S(O)_tR^{20}$ (where t is 1 or 2), —$S(O)_tOR^{20}$ (where t is 1 or 2), —$S(O)_pR^{20}$ (where p is 0, 1 or 2), and —$S(O)_tN(R^{20})_2$ (where t is 1 or 2) where each $R^{20}$ is independently hydrogen, alkyl, haloalkyl, cycloalkyl, cycloalkylalkyl, aryl, aralkyl, heterocyclyl, heterocylylalkyl, heteroaryl, or heteroarylalkyl.

"Aryl" refers to a hydrocarbon ring system radical comprising hydrogen, 6 to 14 carbon atoms, and at least one aromatic ring. For purposes of this invention, the aryl radical may be a monocyclic, bicyclic, or tricyclic system and which may include spiro ring systems. An aryl radical is commonly, but not necessarily, attached to the parent molecule via an aromatic ring of the aryl radical. For purposes of this invention, an "aryl" radical as defined herein can not contain rings having more than 7 members and cannot contain rings wherein two non-adjacent ring atoms thereof are connected through an atom or a group of atoms (i.e., a bridged ring system). Aryl radicals include, but are not limited to, aryl radicals derived from acenaphthylene, anthracene, azulene, benzene, 6,7,8,9-tetrahydro-5H-benzo[7]annulene, fluorene, as-indacene, s-indacene, indane, indene, naphthalene, phenalene, and phenanthrene. Unless stated otherwise specifically in the specification, the term "optionally substituted aryl" is meant to include aryl radicals optionally substituted by one or more substituents independently selected from the group consisting of alkyl, alkenyl, alkynyl, halo, haloalkyl, haloalkenyl, haloalkynyl, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocydylalkynyl, optionally substituted heteroaryl, optionally substituted heteroarylalkyl, optionally substituted heteroarylalkenyl, optionally substituted heteroarylalkynyl, —$R^{21}$—$OR^{20}$, —$R^{21}$—OC(O)—$R^{20}$, —$R^{21}$—$N(R^{20})_2$, —$R^{21}$—C(O)$R^{20}$, —$R^{12}$—C(O)$OR^{20}$, —$R^{21}$—C(O)$N(R^{20})_2$, —$R^{21}$—O—$R^{22}$—C(O)$N(R^{20})_2$, —$R^{21}$—$N(R^{20})$C(O)$OR^{20}$, —$R^{21}$—$N(R^{20})$C(O)$R^{20}$, —$R^{21}$—$N(R^{20})S(O)_tR^{20}$ (where t is 1 or 2), —$R^{21}$—$S(O)_tOR^{20}$ (where t is 1 or 2)—$R^{21}$—$S(O)_pR^{20}$ (where p is 0, 1 or 2), and —$R^{21}$—$S(O)_tN(R^{20})_2$ (where t is 1 or 2), where each $R^{20}$ is independently selected from the group consisting of hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroarylalkyl, or two $R^{20}$'s, together with the common nitrogen to which they are both attached, may optionally form an optionally substituted N-heterocyclyl or an optionally substituted N-heteroaryl, each $R^{21}$ is independently a direct bond or a straight or branched alkylene or alkenylene chain, and $R^{22}$ is a straight or branched alkylene or alkenylene chain.

"Aralkyl" refers to a radical of the formula —$R_b$—$R_c$ where $R_b$ is an alkylene chain as defined above and $R_c$ is one or more aryl radicals as defined above, for example, benzyl, diphenylmethyl and the like. The alkylene chain part of the aralkyl radical may be optionally substituted as described above for an alkylene chain. The aryl part of the aralkyl radical may be optionally substituted as described above for an aryl.

"Aralkenyl" refers to a radical of the formula —$R_d$—$R_c$ where $R_d$ is an alkenylene chain as defined above and $R_c$ is one or more aryl radicals as defined above. The aryl part of the aralkenyl radical may be optionally substituted as described above for an aryl. The alkenylene chain part of the aralkenyl radical may be optionally substituted as defined above for an alkenylene group.

"Aralkynyl" refers to a radical of the formula —$R_aR_c$ where $R_e$ is an alkynylene chain as defined above and R, is one or more aryl radicals as defined above. The aryl part of the aralkynyl radical may be optionally substituted as described above for an aryl. The alkynylene chain part of the aralkynyl radical may be optionally substituted as defined above for an alkynylene chain.

"Arylene" refers to an aryl radical, as defined above, which forms part of a chain in a compound of the invention. The arylene is divalent in that it is attached to the rest of the molecule through two carbons in the arylene. The arylene may be optionally substituted as set forth above for aryl radicals. An example of an arylene is the following group, where the ∿∿ line represents the attachment points of the arylene to the rest of the molecule;

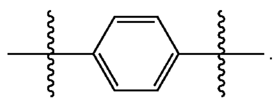

"Cycloalkyl" refers to a stable non-aromatic monocyclic or polycyclic hydrocarbon radical consisting solely of carbon and hydrogen atoms, which may include spiro or bridged ring systems, having from three to fifteen carbon atoms, and which is saturated or unsaturated and attached to the rest of the molecule by a single bond. For purposes of this invention, a bridged ring system is a system wherein two non-adjacent ring atoms thereof are connected through an atom or a group of atoms. Monocydic cycloalkyl radicals include non-bridged cycloalkyl radicals, for example, cyclopropyl, cyclobutyl, cyclopentyl, cyclohexyl, cycloheptyl, and cyclooctyl. Polycyclic radicals include fused, spiro or bridged cycloalkyl radicals, for example, $C_{10}$ radicals such as adamantanyl (bridged) and decalinyl (fused), and $C_7$ radicals such as bicydo[3.2.0]heptanyl (fused), norbornanyl and norbornenyl (bridged), as well as substituted polycyclic radicals, for example, substituted $C_7$ radicals such as 7,7-dimethylbicydo[2.2.1]heptanyl (bridged), and the like. Unless otherwise stated specifically in the specification, cycloalkyl radicals defined herein may be "optionally substituted" by one or more substituents independently selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —$R^{21}$—$OR^{20}$, —$R^{21}$—OC(O)—$R^{20}$, —$R^{21}$—$N(R^{20})_2$, —$R^{21}$—$C(O)R^{20}$, —$R^{21}$—$C(O)OR^{20}$, —$R^{21}$—C(O)$N(R^{20})_2$, —$R^{21}$—$N(R^{20})C(O)OR^{20}$, —$R^{21}$—$N(R^{20})C(O)R^{20}$, —$R^{21}N(R^{20})S(O)_tR^{20}$ (where t is 1 or 2), —$R^{21}$—$S(O)_tOR^{20}$ (where t is 1 or 2), —$R^{21}$—$S(O)_pR^{20}$ (where p is 0, 1 or 2), and —$R^{21}$—$S(O)_tN(R^{20})_2$ (where t is 1 or 2), where each $R^{20}$ is independently selected from the group consisting of hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroarylalkyl, or two $R^{20}$'s, together with the common nitrogen to which they are both attached, may optionally form an optionally substituted N-heterocyclyl or an optionally substituted N-heteroaryl, and each $R^{21}$ is independently a direct bond or a straight or branched alkylene or alkenylene chain.

"Cydoalkylalkyl" refers to a radical of the formula —$R_b$, $R_g$ where $R_b$ is an alkylene chain as defined above and $R_g$ is a cycloalkyl radical as defined above. The alkylene chain and the cycloalkyl radical may be optionally substituted as defined above.

"Cydoalkylalkenyl" refers to a radical of the formula —$R_dR_g$ where $R_d$ is an alkenylene chain as defined above and $R_g$ is a cycloalkyl radical as defined above. The alkenylene chain and the cycloalkyl radical may be optionally substituted as defined above.

"Cycloalkylalkynyl" refers to a radical of the formula —$R_eR_g$ where $R_e$ is an alkynylene radical as defined above and $R_g$ is a cycloalkyl radical as defined above. The alkynylene chain and the cycloalkyl radical may be optionally substituted as defined above.

"Halo" refers to bromo, chloro, fluoro, or iodo.

"Haloalkyl" refers to an alkyl radical, as defined above, that is substituted by one or more halo radicals, as defined above, for example, trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like. The alkyl part of the haloalkyl radical may be optionally substituted as defined above for an alkyl radical.

"Haloalkenyl" refers to an alkenyl radical, as defined above, that is substituted by one or more halo radicals, as defined above. The alkenyl part of the haloalkyl radical may be optionally substituted as defined above for an alkenyl radical.

"Haloalkynyl" refers to an alkynyl radical, as defined above, that is substituted by one or more halo radicals, as defined above. The alkynyl part of the haloalkyl radical may be optionally substituted as defined above for an alkynyl radical.

"Heterocyclyl" refers to a stable 3- to 18-membered non-aromatic ring radical which comprises one to twelve carbon atoms and from one to six heteroatoms selected from the group consisting of nitrogen, oxygen and sulfur. Unless stated otherwise specifically in the specification, the heterocyclyl radical may be a monocyclic, bicycic, tricyclic or tetracydic ring system, which may include spiro or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, 1,4-diazepanyl, decahydroisoquinolyl, imidazolinyl, imidazolidinyl, isothiazolidinyl, isoxazolidinyl, morpholinyl, octahydroindolyl, octahydroisoindolyl, octahydro-1H-pyrrolo[3,2-c]pyridinyl, octahydro-1H-pyrrolo[2,3-c]pyridinyl, octahydro-1H-pyrrolo[2,3-b]pyridinyl, octahydro-1H-pyrrolo[3,4-b]pyridinyl, octahydropyrrolo[3,4-c]pyrrolyl, octahydro-1H-pyrido[1,2-a]pyrazinyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuranyl, thienyl[1,3]dithianyl, trithianyl, tetrahydropyranyl, thiomorpholinyl, thiamorpholinyl, 1-oxo-thiomorpholinyl, 1,1-dioxo-thiomorpholinyl, azetidinyl, octahydropyrrolo[3,4-c]pyrrolyl, octahydropyrrolo[3,4-b]pyrrolyl, decahydroprazino[1,2-a]

azepinyl, azepanyl, azabicyclo[3.2.1]octyl, and 2,7-diazaspiro[4,4]nonanyl. Unless stated otherwise specifically in the specification, the term "optionally substituted heterocyclyl" is meant to include heterocyclyl radicals as defined above which are optionally substituted by one or more substituents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, $—R^{21}—OR^{20}$, $—R^{21}—OC(O)—R^{20}$, $—R^{21}—N(R^{20})_2$, $—R^{21}—C(O)R^{20}$, $—R^{21}—C(O)OR^{20}$, $—R^{21}—C(O)N(R^{20})_2$, $—R^{21}—N(R^{20})C(O)OR^{20}$, $—R^{21}—N(R^{20})C(O)R^{20}$, $—R^{21}—N(R^{20})S(O)_tR^{20}$ (where t is 1 or 2), $—R^{21}—S(O)_tOR^{20}$ (where t is 1 or 2), $—R^{21}—S(O)_pR^{20}$ (where p is 0, 1 or 2), and $—R^{21}—S(O)_tN(R^{20})_2$ (where t is 1 or 2), where each $R^{20}$ is independently selected from the group consisting of hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroarylalkyl, or two $R^{20}$'s, together with the common nitrogen to which they are both attached, may optionally form an optionally substituted N-heterocyclyl or an optionally substituted N-heteroaryl, and each $R^{21}$ is independently a direct bond or a straight or branched alkylene or alkenylene chain.

"N-Heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical may be optionally substituted as described above for heterocyclyl radicals.

"Heterocyclylalkyl" refers to a radical of the formula $—R_bR_h$ where $R_b$ is an alkylene chain as defined above and $R_h$ is a heterocyclyl radical as defined above, and if the heterocyclyl is a nitrogen-containing heterocyclyl, the heterocyclyl may be attached to the alkyl radical at the nitrogen atom. The alkylene chain of the heterocyclylalkyl radical may be optionally substituted as defined above for an alkylene chain. The heterocycyl part of the heterocyclylalkyl radical may be optionally substituted as defined above for a heterocyclyl radical.

"Heterocyclylalkenyl" refers to a radical of the formula $—R_dR_h$ where $R_d$ is an alkenylene chain as defined above and $R_h$ is a heterocyclyl radical as defined above, and if the heterocyclyl is a nitrogen-containing heterocyclyl, the heterocyclyl may be attached to the alkenylene chain at the nitrogen atom. The alkenylene chain of the heterocyclylalkenyl radical may be optionally substituted as defined above for an alkenylene chain. The heterocyclyl part of the heterocyclylalkenyl radical may be optionally substituted as defined above for a heterocyclyl radical.

"Heterocyclylalkynyl" refers to a radical of the formula $—R_eR_h$ where $R_e$ is an alkynylene chain as defined above and $R_h$ is a heterocyclyl radical as defined above, and if the heterocyclyl is a nitrogen-containing heterocyclyl, the heterocyclyl may be attached to the alkynyl radical at the nitrogen atom. The alkynylene chain part of the heterocyclylalkynyl radical may be optionally substituted as defined above for an alkynylene chain. The heterocyclyl part of the heterocyclylalkynyl radical may be optionally substituted as defined above for a heterocyclyl radical.

"Heteroaryl" refers to a 5- to 14-membered ring system radical comprising hydrogen atoms, one to thirteen carbon atoms, one to six heteroatoms selected from the group consisting of nitrogen, oxygen and sulfur, and at least one aromatic ring. A heteroaryl radical is commonly, but not necessarily, attached to the parent molecule via an aromatic ring of the heteroaryl radical. For purposes of this invention, the heteroaryl radical may be a monocyclic, bicyclic or tricyclic ring system, which may include spiro ring systems; and the nitrogen, carbon or sulfur atoms in the heteroaryl radical may be optionally oxidized; the nitrogen atom may be optionally quaternized. For purposes of this invention, the aromatic ring of the heteroaryl radical need not contain a heteroatom, as long as one ring of the heteroaryl radical contains a heteroatom. For example, 1,2,3,4-tetrahydroisoquinolin-7-yl is considered a "heteroaryl" for the purposes of this invention. For purposes of this invention, a "heteroaryl" radical as defined herein can not contain rings having more than 7 members and cannot contain rings wherein two non-adjacent ring atoms thereof are connected through an atom or a group of atoms (i.e., a bridged ring system). Examples of heteroaryl radicals include, but are not limited to, azepinyl, acridinyl, benzimidazolyl, benzo[d]imidazolyl, benzindolyl, 1,3-benzodioxolyl, benzofuranyl, benzoxazolyl, benzothiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, chromeno[4,3-c]pyridazinyl, cinnolinyl, cydopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 7,8'-dihydro-5'H-spiro[[1,3]dioxolane-2,6'-quinoline]-3'-yl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, furopyrimidinyl, furopyridazinyl, furopyrazinyl, isothiazolyl, imidazolyl, imidazopyrimidinyl, imidazopyridazinyl, imidazopyrazinyl, indazolyl, indolyl, indazolyl, isoindolyl, indolinyl, isoindolinyl, isoquinolinyl (isoquinolyl), indolizinyl, isoxazolyl, naphthyridinyl, naphthyrdinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, phenanthridinyl, pteridinyl, purinyl, pyrrolyl, pyrazolyl, pyrazolo[3,4-d]pyrimidinyl, pyridinyl (pyridyl), pyrido[3,2-d]pyrimidinyl, pyrido[3,4-d]pyrimidinyl, pyrido[4,3-c]pyridazinyl, pyrazinyl, pyrimidinyl, pyridazinyl (pyridazyl), pyrrolyl, pyrrolopyrdmidinyl, pyrrolopyridazinyl, pyrrolopyrazinyl, quinazolinyl, quinoxalinyl, quinolinyl, quinuclidinyl, tetrahydroquinolinyl, 5,6,7,8-tetrahydroquinazolinyl, 2,3,4,5-tetrahydrobenzo[b]oxepinyl, 3,4-dihydro-2H-benzo[b][1,4]dioxepinyl, 6,7,8,9-tetrahydro-5H-cyclohepta[b]pyridinyl, 6,7,8,9-tetrahydro-5H-pyrido[3,2-c]azepinyl, 5,6,7,8-tetrahydrobenzo[4,5]thieno[2,3-d]pyrimidinyl, 6,7,8,9-tetrahydro-5H-cyclohepta[45]thieno[2,3-d]pyrimidinyl, 5,6,7,8-tetrahydropyrido[4,5-c]pyridazinyl, thiazolyl, thiadiazolyl, triazolyl, tetrazolyl, 1,2,3,4-tetrahydroisoquinolin-7-yl, triazinyl, thieno[2,3-d]pyrimidinyl, thienopyrimidinyl (e.g., thieno[3,2-d]pyrimidinyl or thieno[2,3-d]pyrimidinyl), thieno[2,3-c]pyridinyl, thienopyridazinyl, thienopyrazinyl, and thiophenyl (thienyl). Unless stated otherwise specifically in the specification, the term "optionally substituted heteroaryl" is meant to include heteroaryl radicals as defined above which are optionally substituted by one or more substituents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, $—R^{21}—OR^{20}$, $—R^{21}—OC(O)—R^{20}$, $—R^{21}—N(R^{20})_2$, $—R^{21}—C(O)R^{20}$, $—R^{21}—C(O)OR^{20}$, $—R^{21}—C(O)N(R^{20})_2$, $—R^{21}—N(R^{20})C(O)OR^{20}$. $—R^{21}—N(R^{20})C(O)R^{20}$, $—R^{21}—N(R^{20})S(O)_tR^{20}$ (where t is 1 or 2), $—R^{21}—S(O)_tOR^{20}$ (where t is 1 or 2), $—R^{21}—S(O)_pR^{20}$ (where p is 0, 1 or 2), and $—R^{21}—S(O)_tN(R^{20})_2$ (where t is 1 or 2), where each $R^{20}$ is independently selected from the group consisting of hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroarylalkyl, or two $R^{20}$'s, together with the common nitrogen to which they are both attached, may optionally form an optionally substituted N-heterocyclyl or an optionally substituted N-heteroaryl, and each $R^{21}$ is independently a direct bond or a straight or branched alkylene or alkenylene chain.

"N-Heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical may be optionally substituted as described above for heteroaryl radicals.

"Heteroarylalkyl" refers to a radical of the formula $—R_bR_i$ where $R_b$ is an alkylene chain as defined above and $R_i$ is a heteroaryl radical as defined above. The heteroaryl part of the heteroarylalkyl radical may be optionally substituted as defined above for a heteroaryl. The alkylene chain part of the heteroarylalkyl radical may be optionally substituted as defined above for an alkylene chain.

"Heteroarylalkenyl" refers to a radical of the formula $—R_dR_i$ where $R_d$ is an alkenylene chain as defined above and $R_i$ is a heteroaryl radical as defined above. The heteroaryl part of the heteroarylalkenyl radical may be optionally substituted as defined above for a heteroaryl. The alkenylene chain part of the heteroarylalkenyl radical may be optionally substituted as defined above for an alkenylene chain.

"Heteroarylalkynyl" refers to a radical of the formula $—R_eR_i$ where $R_e$ is an alkynylene chain as defined above and $R_i$ is a heteroaryl radical as defined above. The heteroaryl part of the heteroarylalkynyl radical may be optionally substituted as defined above for a heteroaryl. The alkynylene chain part of the heteroarylalkynyl radical may be optionally substituted as defined above for an alkynylene chain.

"Heteroarylene" refers to a heteroaryl radical, as defined above, which forms part of a chain in a compound of the invention. The heteroarylene is divalent in that it is attached to the rest of the molecule through two carbons in the heteroarylene, through a nitrogen and a carbon in the heteroarylene, or through two nitrogens in the heteroarylene. The heteroarylene may be optionally substituted as set forth above for heteroaryl radicals. An example of an heteroarylene is the following group, where the ∿∿ line represents the attachment points of the heteroarylene chain to the rest of the molecule:

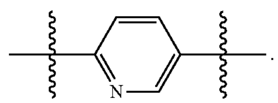 [SMILES: *c1ccc(*)nc1]

Certain chemical groups named herein may be preceded by a shorthand notation indicating the total number of carbon atoms that are to be found in the indicated chemical group. For example: $C_7$-$C_{12}$ alkyl describes an alkyl group, as defined below, having a total of 7 to 12 carbon atoms, and $C_4$-$C_{12}$ cycloalkylalkyl describes a cycloalkylalkyl group, as defined below, having a total of 4 to 12 carbon atoms. The total number of carbons in the shorthand notation does not include carbons that may exist in substituents of the group described.

"Stable compound" and "stable structure" are meant to indicate a compound that is sufficiently robust to survive isolation to a useful degree of purity from a reaction mixture, and formulation into an efficacious therapeutic agent.

"Mammal" includes humans and domestic animals, such as cats, dogs, swine, cattle, sheep, goats, horses, rabbits, and the like. Preferably, for purposes of this invention, the mammal is a human.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution. When a functional group is described as "optionally substituted," and in turn, substitutents on the functional group are also "optionally substituted" and so on, for the purposes of this invention, such iterations are limited to five.

"Pharmaceutically acceptable excipient" includes without limitation any adjuvant, carrier, excipient glidant, sweetening agent, diluent preservative, dye/colorant, flavor enhancer, surfactant, wetting agent, dispersing agent, suspending agent, stabilizer, isotonic agent, solvent or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts that retain the biological effectiveness and properties of the free bases, which are not biologically or otherwise undesirable, and are formed with inorganic acids such as, but not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic add, capric acid, caproic acid, caprylic acid, carbonic acid, cinnamic acid, citric acid, cyclamic acid, dodecylsulfonic acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic add, glutamic acid, glutaric acid, 2-oxo-glutaric acid, glycerophosphoric acid, glycolic acid, hippuric acid, isobutyric add, lactic acid, lactobionic acid, lauric acid, maleic acid, malic acid, malonic acid, mandelic acid, methanesulfonic acid, mucic add, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric add, thiocyanic acid, p-toluenesulfonic acid, trifluoroacetic acid, undecylenic acid, and the like.

"Pharmaceutically acceptable base addition salt" refers to those salts that retain the biological effectiveness and properties of the free adds, and are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts, and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline, and caffeine.

A "pharmaceutical composition" refers to a formulation of a compound of the invention and a medium generally accepted in the art for the delivery of the biologically active compound to mammals, for example, humans. Such a medium includes all pharmaceutically acceptable carriers, diluents or excipients therefor.

"Therapeutically effective amount" refers to that amount of a compound of the invention which, when administered to a mammal, preferably a human, is sufficient to effect treatment, as defined below, of cancer, diabetes, or other disease to be treated in the mammal, preferably a human. The amount of a compound of the invention which constitutes a "therapeutically effective amount" will vary depending on the compound, the cancer, diabetes or other disease to be treated and its severity, and the age of the mammal to be treated, but can be determined routinely by one of ordinary skill in the art having regard to his own knowledge and to this disclosure.

"Treating" or "treatment" as used herein covers the treatment of a disease (e.g., a cancer, diabetes or other disease as described herein) to be treated in a mammal, preferably a human, having the disease, and includes:

(i) preventing the disease from occurring in a mammal, in particular, when such mammal is predisposed to the condition but has not yet been diagnosed as having it according to standard diagnostic criteria in the art;

(ii) inhibiting the disease, i.e., arresting its development;

(iii) relieving the disease, i.e., causing regression of the disease or condition; or (iv) stabilizing the disease.

As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds of the invention, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or as (D)- or (L)- for amino acids. The present invention is meant to include all such possible stereoisomers, as well as their racemic and optically pure forms. Optically active (+) and (−), (R)- and (S)-, or (D)- and (L)-isomers may be prepared using chiral synthons or chiral reagents, or resolved using conventional techniques, such as HPLC using a chiral column. When the compounds described herein contain olefinic double bonds or other centers of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another, as well as diastereomers.

The chemical naming protocol and structure diagrams used herein are a modified form of the I.U.P.A.C. nomenclature system wherein the compounds of the invention are named herein as derivatives of the central core structure, i.e., the triazole structure. For complex chemical names employed herein, a substituent group is named before the group to which it attaches. For example, cyclopropylethyl comprises an ethyl backbone with cyclopropyl substituent. In chemical structure diagrams, all bonds are identified, except for some carbon atoms, which are assumed to be bonded to sufficient hydrogen atoms to complete the valency.

For example, a compound of formula (I) wherein $R^1$, $R^2$, $R^3$, and $R^4$ is hydrogen and $R^5$ is —C(H)═C(H)—$[CH_2]_6$—$CH_3$; i.e., a compound of the following formula (I-1):

(I-1)

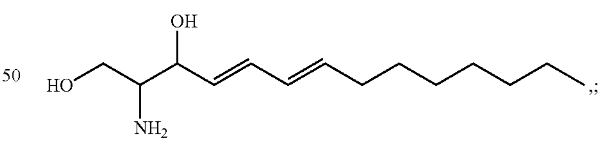

is named herein as 2-aminotetradeca-4,6-diene-1,3-diol. This compound is also referred to herein by the shorthand name, C14Δ4:6Sd. A specific diastereoisomer of compound (I-1) is the following compound (I-1a):

(I-1a)

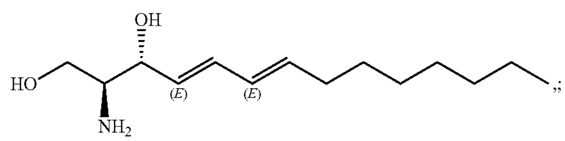

which is named herein as (2S,3R,4E,6E)-2-aminotetradeca-4,6-dlene-1,3-diol. Other diastereoisomers of compound (I-1) may be named in the same manner.

Embodiments of the Invention

Of the various aspects of the invention, as set forth above in the Summary of the invention, certain embodiments are preferred.

In one aspect, this invention is directed to a method of treating a cancer in a mammal, wherein the method comprises administering to the mammal a therapeutically effective amount of a compound of formula (I):

Accordingly, in one embodiment this invention is directed to a method of treating a cancer in a mammal, wherein the method comprises administering to the mammal a therapeutically effective amount of a compound of formula (I):

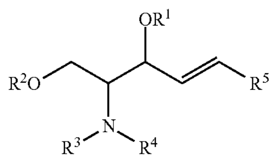

wherein:

$R^1$ and $R^2$ are independently selected from the group consisting of hydrogen, alkyl, optionally substituted cycloalkyl, optionally substituted aralkyl, optionally substituted heterocyclylalkyl, optionally substituted heteroarylalkyl, —C(O)$R^6$, —C(O)N($R^6$)$R^7$, —S(O)$_t$$R^6$ (where t is 1 or 2), —S(O)$_2$N($R^6$)$R^7$, —P(O)$_2$O$R^6$ and —C(S)$R^6$;

$R^3$ and $R^4$ are independently selected from the group consisting of hydrogen, alkyl, optionally substituted aralkyl, —C(O)$R^6$, and —C(O)O$R^6$, or $R^3$ and $R^4$, together with the common nitrogen to which they are both attached, form an optionally substituted N-heterocyclyl or an optionally substituted N-heteroaryl;

$R^6$ is selected from the group consisting of —C($R^9$)═C($R^9$)—[C($R^{10}$)]$_m$—$R^8$—[C($R^{10}$)]$_n$—$CH_3$ where m+n is 6 to 10, —[C($R^{10}$)]$_2$—C($R^9$)═C($R^9$)—[C($R^{10}$)]$_q$—$R^8$—[C($R^{10}$)]$_r$—$CH_3$ where q+r is 4 to 8, and —C($R^9$)═C($R^9$)—C($R^9$)═C($R^9$)—[C($R^{10}$)]$_u$—$R^8$—[C($R^{10}$)]$_v$—$CH_3$ where u+v is 4 to 8:

each $R^6$ and $R^7$ is independently selected from the group consisting of hydrogen, alkyl, alkenyl, alkynyl, optionally substituted cycloalkyl, optionally substituted cycloalkylalkyl, optionally substituted cycloalkylalkenyl, optionally substituted cyloalkylalkynyl, optionally substituted aryl, optionally substituted aralkyl, optionally substituted aralkenyl, optionally substituted aralkynyl, optionally substituted heterocyclyl, optionally substituted heterocyclylalkyl, optionally substituted heterocyclylalkenyl, optionally substituted heterocycylalkynyl, optionally substituted heteroaryl, optionally substituted heteroarylalkyl, optionally substituted heteroarylalkenyl, and optionally substituted heteroarylalkynyl;

each $R^8$ is selected from the group consisting of a direct bond, an optionally substituted arylene chain and an optionally substituted heteroarylene chain;

each $R^9$ is independently hydrogen or alkyl;

each $R^{10}$ is independently selected from the group consisting of hydrogen, halo, haloalkyl, alkyl, alkenyl, alkynyl, —$R^{11}$—O$R^6$, —$R^{11}$—OC(O)$R^6$, —$R^{11}$—S(O)$_p$$R^6$ (where p is 0, 1 or 2), —$R^{11}$—C(O)$R^6$, —$R^{11}$—C(O)O$R^6$, —$R^{11}$—N($R^6$)$R^7$, and —$R^{11}$—C(O)N($R^6$)$R^7$; and each $R^{11}$ is independently selected from a direct bond, an optionally substituted straight or branched alkylene chain, an optionally substituted straight or branched alkenylene chain and an optionally substituted straight or branched alkynylene chain;

as an isolated stereoisomer or mixture thereof, or a pharmaceutically acceptable salt thereof.

In one embodiment of this aspect, the compound of formula (I) is a compound of formula (I), as set forth above, wherein each $R^8$ is a direct bond.

In another embodiment of this aspect, the compound of formula (I) is a compound of formula (I), as set forth above, wherein each $R^6$ is an optionally substituted arylene.

In another embodiment of this aspect, the compound of formula (I) is a compound of formula (I), as set forth above, wherein each $R^8$ is an optionally substituted heteroarylene.

In another embodiment of this aspect, the compound of formula (I) is a compound of formula (I), as set forth above, wherein each $R^8$ is an optionally substituted heteroarylene chain In one embodiment of this aspect, the compound of formula (I) is a compound of formula (I), as set forth above, wherein $R^5$ is selected from the group consisting of —C($R^9$)═C($R^9$)—[C($R^{10}$)$_2$]$_6$—$CH_3$, —C($R^9$)═C($R^9$)—[C($R^{10}$)$_2$]$_{10}$—$CH_3$, —[C($R^{10}$)]$_2$—C($R^9$)═C($R^9$)—[C($R^{10}$)$_2$]$_4$ —$CH_3$, —[C($R^{10}$)]$_2$—C($R^9$)═C($R^9$)—[C($R^{10}$)$_2$]$_8$ —$CH_3$, —C($R^9$)═C($R^9$)—C($R^9$)═C($R^9$)—[C($R^{10}$)$_2$]$_4$—$CH_3$ and —C($R^9$)═C($R^9$)—C($R^9$)═C($R^9$)—[C($R^{10}$)$_2$]$_8$—$CH_3$.

In one embodiment of this aspect, the compound of formula (I) is a compound of formula (I), as set forth above, wherein $R^6$ is selected from the group consisting of —C(H)═C(H)—[C($R^{10}$)$_2$]$_6$—$CH_3$, —C(H)═C(H)—[C($R^{10}$)$_2$]$_{10}$ —$CH_3$, —[C($R^{10}$)]$_2$—C(H)═C(H)—[C($R^{10}$)$_2$]$_4$—$CH_3$, —[C($R^{10}$)]$_2$—C(H)═C(H)—[C($R^{10}$)$_2$]$_8$—$CH_3$, —C(H)═C(H)—C(H)═C(H)—[C($R^{10}$)$_2$]$_4$—$CH_3$, —C(H)═C(H)—C(H)═C(H)—[C($R^{10}$)$_2$]$_8$—$CH_3$, —C(H)═C($CH_3$)—[C($R^{10}$)$_2$]$_6$—$CH_3$, —C(H)═C($CH_3$)—[C($R^{10}$)$_2$]$_{10}$ —$CH_3$, —[C($R^{10}$)]$_2$C(H)═C($CH_3$)—[C($R^{10}$)$_2$]$_4$—$CH_3$, —[C($R^{10}$)]$_2$—C(H)═C($CH_3$)—[C($R^{10}$)$_2$]$_8$—$CH_3$, —C(H)═C($CH_3$)—C(H)═C(H)—[C($R^{10}$)$_2$]$_4$—$CH_3$ and —C(H)═C($CH_3$)—C(H)═C(H)—[C($R^{10}$)$_2$]$_8$—$CH_3$.

In one embodiment of this aspect, the compound of formula (I) is a compound of formula (I), as set forth above, wherein:

$R^1$ and $R^2$ are each hydrogen;

$R^3$ and $R^4$ are each hydrogen;

$R^5$ is selected from the group consisting of —C(H)═C(H)—[C($R^{10}$)$_2$]$_6$—$CH_3$, —C(H)═C(H)—[C($R^{10}$)$_2$]$_{10}$—$CH_3$, —[C($R^{10}$)]$_2$—C(H)═C(H)—[C($R^{10}$)$_2$]$_4$—$CH_3$. —[C($R^{10}$)]$_2$—C(H)═C(H)—[C($R^{10}$)$_2$]$_8$—$CH_3$, —C(H)═C(H)—C(H)═C(H)—[C($R^{10}$)$_2$]$_4$—$CH_3$, —C(H)═C(H)—C(H)═C(H)—[C($R^{10}$)$_2$]$_8$—$CH_3$, —C(H)═C($CH_3$)—[C($R^{10}$)$_2$]$_6$—$CH_3$, —C(H)═C($CH_3$)—[C($R^{10}$)$_2$]$_{10}$ —$CH_3$, —[C($R^{10}$)]$_2$—C(H)═C($CH_3$)—[C($R^{10}$)$_2$]$_4$—$CH_3$, —[C($R^{10}$)]$_2$—C(H)═C($CH_3$)—[C($R^{10}$)$_2$]$_8$—$CH_3$, —C(H)═C($CH_3$)—C(H)═C(H)—[C($R^{10}$)$_2$]$_4$—$CH_3$ and —C(H)═C($CH_3$)—C(H)═C(H)—[C($R^{10}$)$_2$]$_8$—CH;

each $R^6$ and $R^7$ is independently selected from the group consisting of hydrogen, haloalkyl and alkyl;

each $R^{10}$ is independently selected from the group consisting of hydrogen, halo, haloalkyl, alkyl, alkenyl, alkynyl, —$R^{11}$—O$R^6$, —$R^{11}$—OC(O)$R^6$, —$R^{11}$—S(O)$_p$$R^6$ (where p is 0, 1 or 2), —$R^{11}$—C(O)$R^6$, —$R^{11}$—C(O)O$R^6$, —$R^{11}$—N($R^6$)$R^7$, and —$R^{11}$—C(O)N($R^6$)$R^7$; and each $R^{11}$ is independently selected from a direct bond and an optionally substituted straight or branched alkylene chain.

In one embodiment of this aspect, the compound of formula (I) is a compound of formula (I), as set forth above, selected from the group consisting of:

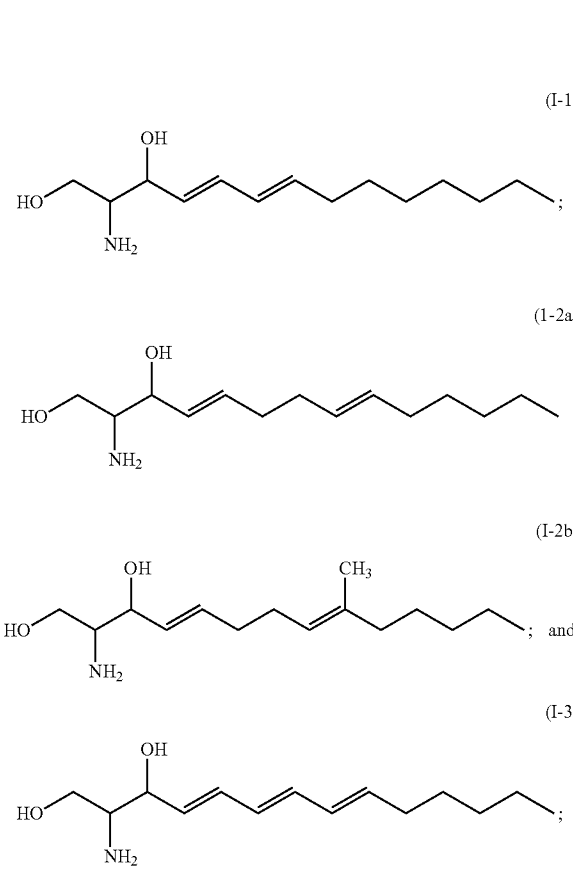

as an isolated stereoisomer or mixture thereof, or a pharmaceutically acceptable salt thereof.

Preferably, the compound of formula (I-1), the compound of formula (I-2a), the compound of formula (I-2b) and the compound of formula (I-3) have the following stereochemistry:

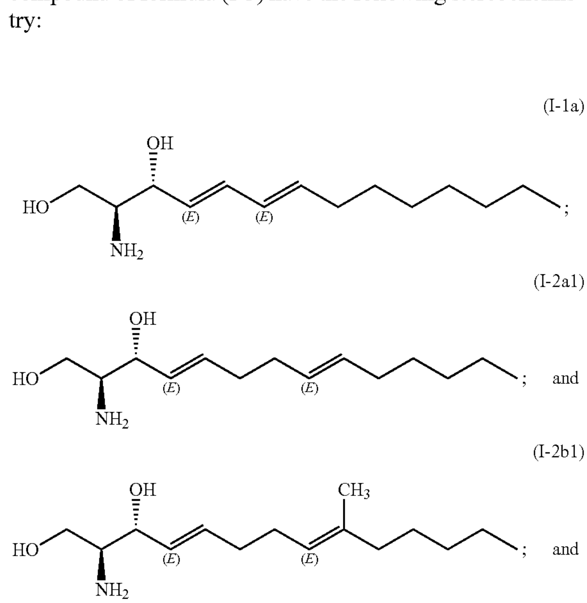

-continued

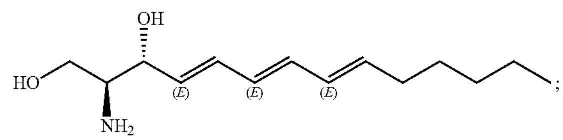

or a pharmaceutically acceptable salt thereof.

Even more preferably, the compound of formula (I) is a compound of formula (I-1a), as an isolated stereoisomer or mixture thereof, or a pharmaceutically acceptable salt thereof.

In one embodiment of this aspect, the compound of formula (I) is a compound of formula (I), as set forth above, is selected from the group consisting of:

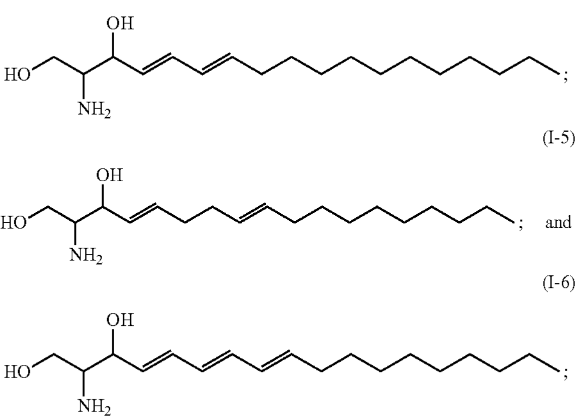

as an isolated stereoisomer or mixture thereof, or a pharmaceutically acceptable salt thereof.

Preferably, the compound of formula (I-4), the compound of formula (I-5) and the compound of formula (I-6) have the following stereochemistry:

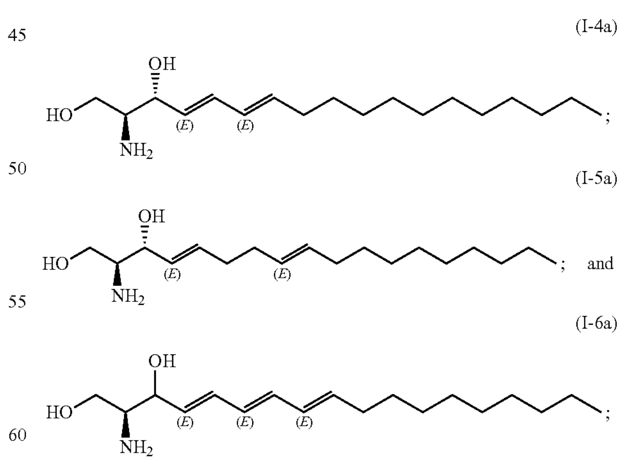

or a pharmaceutically acceptable salt thereof.

Even more preferably, the compound of formula (I) is a compound of formula (I-4-a), as an isolated stereoisomer or mixture thereof, or a pharmaceutically acceptable salt thereof.

Further embodiments of the invention include methods for the treatment of a variety of cancers and other diseases by administering the compounds of the invention such as the compounds of formula (I) any one or more of (I-1)-(1-6) as described herein. In this regard. a cancer to be treated may be associated with activation of AKT or $PI_3$ kinase, or may be associated with a deficiency of PTEN activity. In a further embodiment, the cancer to be treated may be associated with activation of the Wnt signaling pathway. A variety of cancers are suitably treated using the methods and compounds of the invention, including but not limited to, gastrointestinal cancers, colon cancer, breast cancer, neuroblastoma, leukemia, and brain tumors.

In one embodiment, the compounds of the invention are administered orally.

In a further embodiment, the compounds of the invention alter the activity of a component of the AKT/$PI_3$ kinase signaling pathway. In this regard, in certain embodiments, the compounds of the invention inhibit the activity of AKT. In particular, in one embodiment, the compounds of the invention inhibit the cytosolic to membrane translocation of AKT. In another embodiment, the compounds activate the PTEN phosphatase. In a further embodiment of the invention, the compounds of the invention act as competitive inhibitors of sphingosine kinase.

Specific embodiments of the invention are described in more detail below in the following sections.

Utility and Testing of the Compounds of the Invention

Free sphingoid bases isolated from *Drosophila* (e.g., *Drosophila melanogaster*) are comprised largely of $C_{14}$- and $C_{16}$-sphingosine and dihydrosphingosine (38). As disclosed herein, a second family of sphingolipids has been identified based on their differential separation in high performance liquid chromatography (HPLC) compared to previously known *Drosophila* sphingolipids. The herein disclosed *Drosophila* sphingadlene sphlngolipids contain a long chain base (LCB) of either 14 or 16 carbons with conjugated double bonds at C4 and C6. These $C_{14}$-sphingadienes and their corresponding $C_2$-ceramides decrease (e.g., reduce in a statistically significant manner) cell proliferation and increase (e.g., induce in a statistically significant manner) apoptosis in *Drosophila* cells, and also likely contribute to tissue degeneration in *Drosophila* mutants that accumulate these compounds, due to effects on key conserved signaling pathways.

As a brief background, sphingadienes have been identified in numerous biological species. They are commonly found in plants and plant-derived dietary constituents such as soy and legumes where the long chain base (LCB) is desaturated at C4 and C8 (39). They have also been detected as rare endogenous lipids in mammalian and human brain, aorta and plasma (40-43). The presence of sphingolipids containing LCBs that are desaturated at C4 and C6 has previously been reported in insect species other than *Drosophila*, indicating that these structures may be conserved among dipteran insects. A study of sphingomyelins from the tobacco homworm *Manduca sexta* revealed the presence of the desaturated LCB in sphingomyelin, ceramide-phosphoethanolamine, and ceramide (44). Moreover, a ceramide compound purified from larvae of the silk mouth *Bombyx mori* was shown to contain a desaturated LCB (45).

The *Drosophila* sphingadienes disclosed herein are medium-chain C14 sphingolipids containing two double bonds. Ceramide compounds containing two double bonds (and an N-acyl chain) were found previously to be more cytotoxic to breast cancer cells than ceramides with a single double bond in the long chain base (LCB) (46). The *Drosophila* sphingadlenes disclosed herein are contemplated for colon cancer chemotherapy because, according to non-limiting theory: 1) the presence of two double bonds in their LCB may increase their cytotoxicity relative to other similar long chain bases, 2) the shorter chain length of their LCB compared with mammalian sphingoid bases makes them more water-soluble, thereby facilitating their delivery as drugs, 3) the shorter chain length of their LCB also makes them more cell-permeable than mammalian and plant sphingoid bases, 4) they are not acylated (i.e., they are not ceramides) and are, therefore, more readily taken up by colonic epithelial cells compared to ceramides, which must first be converted to sphingoid bases by intestinal brush border enzymes prior to cellular uptake, 5) unlike mammalian sphingoid bases, the medium-chain *Drosophila* sphingadienes accumulate in colon cancer cells, due to inefficient conversion to sphingosine-1-phosphate (S1P) and subsequent poor clearance of the phosphorylated compound by S1P lyase, and 6) they promote cytotoxicity in colon cancer cells by inhibiting protein synthesis through the AKT signaling pathway, which is upregulated in many cancers of colonic and other origins, making it likely that sphingadiene effects will be more pronounced in cancer cells than in normal cells (47-50).

The sphingadiene compounds of certain presently disclosed invention embodiments are useful for the treatment of cancer. In particular cancers associated with altered (e.g., increased or decreased in a statistically significant manner) activity of any one or more components of the AKT/phosphonositide 3-kinase (PI3 kinase) signaling pathway. In this regard, the compounds described herein can be used for the treatment of colon cancer, breast cancer, neuroblastoma, leukemia, brain tumors, gastrointestinal cancers, and any cancer demonstrating upregulation of AKT or PI3 kinase or deficiency of PTEN (phosphatase and tensin homolog) activity. Cancers associated with altered activity of one or more components of the AKT/PI3 kinase signaling pathway that may be treated with the compounds described herein also include but are not limited to, cob-rectal cancer, breast cancer, prostate cancer, brain cancer, melanoma, non-Hodgkin's lymphoma, Hodgkin's disease, leukemias, plasmocytomas, sarcomas, adenomas, gliomas, thymomas, kidney cancer, renal cell carcinoma, uterine cancer, pancreatic cancer, esophageal cancer, lung cancer, ovarian cancer, cervical cancer, testicular cancer, gastric cancer, multiple myeloma, hepatoma, acute lymphoblastic leukemia (ALL), acute myelogenous leukemia (AML), chronic myelogenous leukemia (CML), and chronic lymphocytic leukemia (CLL), or other cancers. The sphingadiene compounds of the present invention embodiments may be used to inhibit the development of cancer, metastasis, or both development of cancer and metastasis in an individual afflicted with a cancer.

The presently disclosed sphingadiene compounds may also be used for the treatment of diabetes, and for the treatment of infections with intracellular bacteria, such as but not limited to *Chlamydia* spp, *Mycobacteria tuberculosis, Rickettsia* spp, *Salmonella* spp, *Brucella* spp, and others such as those described in Zinsser, Microbiology, 20th Edition, 1992, Appleton & Lange, Norwalk, Conn.

As noted above, altered activity of components of the Akt/PI3 kinase pathway provides a method for inhibiting the growth (i.e., proliferation) of a cancer cell, either in culture or in a mammal afflicted with cancer. In vivo, such alteration or modulation may also be used to inhibit cancer development, progression and/or metastasis. Accordingly, one or more of the compounds as provided herein may be administered as described above to a mammal in need of anti-cancer therapy. Patients that may benefit from administration of a modulating agent are those afflicted with cancer. Such patients may be identified based on standard criteria that are well known in the art.

As used herein, "AKT" or "AKT protein" means a mammalian protein, and in particular, a human protein, that is a member of the set of PKBa/Akt1, PKBb/Akt2, PKBg/Akt3, PKBg-1, and proteins having substantially identical amino acid sequences thereof, and that has protein kinase activity whenever phoshorylated by a PI3K protein. In one embodiment, an Akt protein has kinase activity whenever either or both of a tyrosine at a location number from 305 to 310 is phosphorylated and a serine at location number from 470 to 475 is phosphorylated. Akt proteins are described under various NCBI accession numbers, including NP__005154 (SEQ ID NO:1), and in Nicholson et al., *Cellular Signalling* 2002, 14:381-395; Kandel et al., *Exp. Cell. Res.* 1999, 253: 210-229: and like references.

"Phosphatidylinositol 3 kinase protein" or equivalently a "PI3K protein" or "PI3 kinase" means a mammalian, in particular, a human, intracellular protein of the set of proteins described under NCBI accession numbers NP__852664, $NP_{13}$ 852556, and NP__852665 (provided in SEQ ID NOs:2, 3, and 4, respectively), and proteins having amino acid sequences substantially identical thereto and that retain substantially the same activity.

"PTEN" or "PTEN protein" (phosphatase and tensin homology) means a mammalian protein, in particular, a human protein such as described in published sequences, for example the sequence information set forth in GenBank accession number U93051, provided herein as SEQ ID NO:5, and proteins having amino acid sequences substantially identical thereto and that retain substantially the same activity.

"Substantially identical" in reference to proteins or amino acid sequences of proteins in a family of related proteins that are being compared means either that one protein has an amino acid sequence that is at least fifty percent identical to the other protein or that one protein is an isoform or splice variant of the same gene as the other protein. Generally, proteins having substantially identical amino acid sequences retain substantially the same activity (e.g., kinase activity, phosphatase activity and the like) or in certain embodiments, may have increased activity as compared to the native protein sequence. In one embodiment, substantially identical means one protein, or amino acid sequence thereof, is at least 80%, 85%, 90%, 95%, 96%, 97%, 98%, or 99% identical to the other protein, or amino acid sequence thereof.

The sphingosine compounds described herein alter (e.g., increase or decrease in a statistically significant manner) the activity of one or more components of the Akt/PI3 kinase signaling pathway.

Any component of the AKT/PI3 kinase signaling pathway may be regarded as within the context of the present invention, for example, with respect to embodiments that relate to altering (e.g., increasing or decreasing in a statistically significant manner) the activity of one or more AKT/PI3 kinase signalling pathway components. As such, components of the AKT/PI3 kinase signaling pathway may include but are not limited to Akt, PI3 kinase, phosphatidylinositol phosphates (such as $PIP_3$), receptor tyrosine kinase (RTK), PTEN, pyruvate dehydrogenase kinase 1 (PDK1), mammalian target of rapamycin (mTOR), p27, murine double minute (Mdm2), IκB kinase (IKK), Caspase 9, Forkhead. Bad, glycogen synthase kinase 3 (GSK3), Raf1, Yes-associated protein (YAP), p53, WNK1, p21, IκB, p50, p65, and NF-κB, for which activity assays have been described, as will be known to those familiar with the art (see for example Brazil et al., *Trends Biochem. Sci.* 2004, 29:233-242; Brazil et al., *Cell* 2002, 111:293-303; Cantley *Science* 2002, 296:1655-1657; Shiojima et al. *Circ. Res.* 2002, 90.1243-1250: Vivanco et al. *Nat. Rev. Cancer* 2002, 2:489-501; Woodgett *Curr. Opin. Cell Biol.* 2005, 17:150-157).

The sphingosine compounds described herein also alter (e.g., increase or decrease in a statistically significant manner) the activity of one or more components of the Wnt signaling pathway. Any component of the Wnt signaling pathway may be regarded as within the context of the present invention, for example, with respect to embodiments that relate to altering (e.g., increasing or decreasing in a statistically significant manner) the activity of one or more Wnt signalling pathway components. As such, components of the Wnt signaling pathway may include but are not limited to, in particular, those components of the canonical Wnt signaling pathway such as, Wnt, Frizzled, β-catenin, Disheveled, GSK3, Axin, APC, βTrCP, WTX, CK1, naked, and downstream genes that may be affected by the activity of any of these proteins.

Altered activity comprises any statistically significant change, e.g. increase or decrease, in the activity of one or more components of the Akt/PI3 kinase signaling pathway and/or the Wnt signaling pathway when an isolated component, or a host cell or an animal comprising a component is contacted with the compound as compared to an isolated component, a host cell or animal comprising a component that is not contacted with the compound. As such, in one embodiment, modulation or alteration of activity comprises an altered activity level, that is a statistically significant decrease or increase in enzymatic activity of any enzyme involved in the Akt/PI3 kinase signaling pathway or the Wnt signaling pathway. Numerous methods for detecting and measuring enzymatic activity, such as phosphatase and kinase activity are known in the art and can be used in the context of the present invention (see e.g. *Current Protocols in Protein Science*, John Wiley & Sons, Inc., Boston, Mass.).

In one embodiment of the invention, the altered activity of one or more components of the Akt/PI3 kinase signaling pathway comprises a decrease in the activity of Akt. In one particular embodiment, this decrease in actMty results from inhibition of the cytosolic to membrane translocation of the AKT protein.

In another embodiment, the alteration in activity of one or more components of the Akt/PI3 kinase signaling signaling pathway comprises the activation of (Increase in activity of) the PTEN phosphatase.

In one embodiment, the alteration in activity of one or more components of the Wnt signaling pathway comprises translocation of β-catenin from the nucleus to the cytoplasm, thereby negatively regulating the Wnt signaling pathway.

In certain embodiments modulation of a component involved in the Akt/PI3 kinase signaling pathway or the Wnt signaling pathway comprises an increase or decrease in one or more of cellular proliferation, apoptosis, autophagy, angiogenesis, drug resistance and cell motility. A variety of assays to determine these and related cellular functions are known in the art, including those described in *Current Protocols in Immunology*, or *Current Protocols in Cell Biology*, both published by John Wiley & Sons, Inc., Boston, Mass.

Signaling resulting from the Akt/PI3 kinase signaling pathway and the Wnt signaling pathway contributes to specific pathways for biological signal transduction, including those associated with cell division, cell survival, apoptosis, proliferation and differentiation. "Biological signal transduction pathways" or "inducible signaling pathways" in the context of the present invention include transient or stable associations or interactions among molecular components involved in the control of these and similar processes in cells. Depending on the particular aspect of the pathway of interest, an appropriate parameter for determining induction or inhibition of such pathway may be selected. There is available a variety of well known methodologies for quantifying cellular proliferation, including, for example, incorporation of tritlated thymidine into cellular DNA, monitoring of detectable (e.g., fluorimetric or colorimetric) indicators of cellular respiratory activity, or cell counting, or the like. Similarly, in the cell biology arts there are known multiple techniques for assessing cell survival (e.g., vital dyes, metabolic indicators, etc.), for determining apoptosis (e.g., annexin V binding, DNA fragmentation assays, caspase activation, etc.) and for determining autophagy (e.g., tracking the conversion of LC3-1 to LC3-2 as a marker for autophagic activity).

In certain embodiments, signaling pathways will be associated with particular cellular phenotypes, for example specific induction of gene expression (e.g., detectable as transcription or translation products, or by bioassays of such products, or as nuclear localization of cytoplasmic factors), altered (e.g., statistically significant increases or decreases) levels of intracellular mediators (e.g., activated kinases or phosphatases, altered levels of cyclic nucleotides or of physiologically active ionic species, lipid intermediates, phosphorylated or dephosphorylated docking proteins, scaffold proteins, chaperone proteins, etc.), or altered cellular morphology, and the like, such that cellular responsiveness to a particular stimulus as provided herein can be readily identified to determine whether a particular cell responds to a particular stimulus, such as by contact with the compounds described herein. For example, signaling, kinase and phosphatase activity may be determined using any of a variety of assays known in the art or commercially available assay kits, such as those available from Reaction Biology Corp., Malvem, Pa. and Cell Signaling Technology, Inc., Danvers. Mass.

Specifically, β-catenin expression and localization can be determined by immunoblotting (cytosolic and nuclear) extracts with a monoclonal antibody that recognizes β-catenin and IF and confocal microscopy essentially as described (Schmelz, et al., Cancer Res 61(18): 6723-6729., 2001.). Nuclei can be isolated using the Nuclear Extract Kit (Active Motif). The effect of the sphingosine compounds described herein on β-catenin/TCF-dependent gene expression may be assessed by transfecting cells with a TCF-responsive reporter system. Cells are transfected with the TOPflash TCF reporter plasmid (Upstate, now part of Millipore, Billrica, Mass), which contains three copies of the TCF binding site upstream of a TK minimal promoter and luciferase open reading frame. The FOPflash vector, which contains mutated TCF binding sites, can serve as a negative control. Transfections and luciferase assays may be performed as described (Oskouian, et al., J Biol Chem 280(18): 18403-18410, 2005). Antibodies against components of the signaling pathways described herein, such as $PI_3K$/AKT, 4EBP and PTEN antibodies are commercially available, for instance, from Cell Signaling Technologies, Danvers, M A. Fluorescent microscopy can also be used for detecting components of the signaling and sphingolipid pathways described herein. Fluorescent microscopy may be performed using commercially available equipment, such as a Zeiss Axiovert 25 equipped with a Diagnostic spot digital camera.

In certain embodiments, alteration of the activity of one or more components of the Akt/PI3 kinase signaling pathway and/or the Wnt signaling pathway comprises an altered level, e.g., a statistically significant decrease or increase relative to appropriate controls in, gene expression of or enzyme activity level of and/or phosphorylation state of a downstream target of the pathway. Numerous methods for detecting polypeptide and/or polynucleotide levels (e.g., gene expression), enzyme activity (e.g., kinase, phosphatase, protease, etc.), and phosphorylation status are known in the art and are useful in the context of the instant invention. Illustrative methods are described in Ausubel et al. (1993 *Current Protocols in Molecular Biology*, Greene Publ. Assoc. Inc. & John Wiley & Sons, Inc., Boston, Mass.); Sambrook et al. (1989 *Molecular Cloning*, Second Ed., Cold Spring Harbor Laboratory, Plainview, N.Y.); Maniatis at al. (1982 *Molecular Cloning*, Cold Spring Harbor Laboratory, Plainview, N.Y.) and elsewhere.

According to certain embodiments contemplated herein, the compounds of the present invention also inhibit sphingosine kinase. Sphingosine kinase (SK) is a component of the sphingolipid metabolic pathway and functions primarily to convert (phosphorylate) sphingosine to sphingosine-1-phosphate (S1P). S1P then acts as the trigger to the ensuing signalling processes that ultimately activate various pro-survival mechanisms in a cell. Importantly, sphingosine kinase activity is known to be upregulated in many cancers. SK proteins are known in the art and are described under various NCBI accession numbers. A representative human SK polypeptide sequence is provided in SEQ ID NO:6.

In certain embodiments, inhibition of sphingosine kinase may have effects on other components of the sphingolipid metabolic pathway. Thus in certain embodiments, the compounds of the present invention modulate one or more components of this pathway. Any component of the sphingolipid metabolic and/or signaling pathway may be regarded as within the context of the present invention. As such, components of the sphingolipid metabolic and/or signaling pathway include but are not limited to, enzymes involved in these pathways (and the polynucleotides encoding said enzymes), such as, sphingosine-1-phosphate lyase (SPL), SK, ceramidase, S1-PP, serine palmitoyltransferase (SPT), 3-ketodihydrosphingosine reductase, ceramide synthase, dihydroceramide desaturase, sphingosine desaturase, ceramide kinase, phosphoethanolamine cytidylyltransferase, CDP-ethanolamine phosphotransferase, acid sphingomyellnase, sphingomyelin synthase, neutral sphingomyelinase, S1P phosphatase, and glucosylceramide synthase. Components of the sphingolipid metabolic and/or signaling pathway further include intracellular or cell surface receptors, and the polynucleotides encoding said receptors, such as the G-protein coupled S1P receptors (formerly called EDG receptors,e.g. EDG1, EDG3, EDG5, EDG6. EDG8) and CFTR.

Generally sphingolipid metabolism can be viewed as all synthetic and catabolic pathways involving any sphingolipid or sphingolipid intermediate as described herein. Sphingolipid signaling pathways are known in the art and can generally be viewed herein as any signaling pathway activated by a sphingolipid, such as the signaling pathways of sphingosine-1-phosphate such as those described in Pyne, S., and Pyne, N. J. *Biochem. J.* 2000, 349:385-402 and Pyne, S., and Pyne. N. J. *Pharmacology and Therapeutics* 2000, 88:115-131. However, the skilled artisan would recognize that other sphingolipid signaling pathways fall within the scope of the present invention and are contemplated herein.

The skilled artisan would readily appreciate that there any many assays known in the art for measuring inhibition of SK activity. Within certain embodiments, various in vitro assay for SK activity may be performed to detect inhibition of SK. Illustrative assays are described for example, by Caligan, et al. *Analytical Biochemistry* 2000, 281:36-44; Skrzypek, M., et al., *J. Bacteriol.* 1999, 181:1134-1140; Kim, S., et al., *Genetics* 2000 156:1519-1529; Lanterman, M. and Saba, J.,

*Biochem. J.* 1998 332:525-531. In further embodiments, inhibition of SK can be determined using gene expression analysis by standard molecular biological techniques, or by detection of the effects of inhibition of SK on other components of the sphingolipid metabolic pathway e.g., measuring levels of S1P.

Pharmaceutical Compositions of the Invention and Administration

Administration of the compounds of the invention, or their pharmaceutically acceptable salts, in pure form or in an appropriate pharmaceutical composition, can be carried out via any of the accepted modes of administration of agents for serving similar utilities. The pharmaceutical compositions of the invention can be prepared by combining a compound of the invention with an appropriate pharmaceutically acceptable carrier, diluent or excipient and may be formulated into preparations in solid, semi-solid, liquid or gaseous forms, such as tablets, capsules, powders, granules, ointments, solutions, suppositories, injections, inhalants, gels, microspheres, and aerosols. In addition, other pharmaceutically active ingredients (including other anti-cancer agents) and/or suitable excipients such as salts, buffers and stabilizers may, but need not, be present within the composition.

Administration may be achieved by a variety of different routes, including oral, parenteral, nasal, intravenous, intradermal, subcutaneous or topical. Preferred modes of administration depend upon the nature of the condition to be treated or prevented. An amount that, following administration, inhibits, prevents or delays the progression and/or metastasis of a cancer is considered effective.

In certain embodiments, the amount administered is sufficient to result in regression, as indicated by 50% mass or by scan dimensions. The precise dosage and duration of treatment is a function of the disease being treated and may be determined empirically using known testing protocols or by testing the compositions in model systems known in the art and extrapolating therefrom. Controlled clinical trials may also be performed. Dosages may also vary with the severity of the condition to be alleviated. A pharmaceutical composition is generally formulated and administered to exert a therapeutically useful effect while minimizing undesirable side effects. The composition may be administered one time, or may be divided into a number of smaller doses to be administered at intervals of time. For any particular subject, specific dosage regimens may be adjusted over time according to the individual need.

The compounds of the present invention may be administered alone or in combination with other known cancer treatments, such as radiation therapy, chemotherapy, transplantation, immunotherapy, hormone therapy, photodynamic therapy, etc. The compounds may also be administered in combination with antibiotics used to treat bacterial infections, in particular intracellular bacterial infections.

Typical routes of administering these and related pharmaceutical compositions thus include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques. Pharmaceutical compositions of the invention are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art for example, see *Remington: The Science and Practice of Pharmacy,* 20th Edition (Philadelphia College of Pharmacy and Science, 2000). The composition to be administered will, in any event, contain a therapeutically effective amount of a compound of the invention, or a pharmaceutically acceptable salt thereof, for treatment of a disease or condition of interest in accordance with the teachings of this invention.

A pharmaceutical composition of the invention may be in the form of a solid or liquid. In one aspect, the carrier(s) are particulate, so that the compositions are, for example, in tablet or powder form. The carrier(s) may be liquid, with the compositions being, for example, an oral oil, injectable liquid or an aerosol, which is useful in, for example, inhalatory administration.

When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and Isotonic agent may be included.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition of the invention intended for either parenteral or oral administration should contain an amount of a compound of the invention such that a suitable dosage will be obtained. Typically, this amount is at least 0.01% of a compound of the invention in the composition. When intended for oral administration, this amount may be varied to be between 0.1 and about 70% of the weight of the composition. Preferred oral pharmaceutical compositions contain between about 4% and about 75% of the compound of the invention. Preferred pharmaceutical compositions and preparations according to the present invention are prepared so that a parenteral dosage unit contains between 0.01 to 10% by weight of the compound prior to dilution of the invention.

The pharmaceutical composition of the invention may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the compound of the invention from about 0.1 to about 10% w/v (weight per unit volume).

The pharmaceutical composition of the invention may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition of the invention may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of the invention in solid or liquid form may include an agent that binds to the compound of the invention and thereby assists in the delivery of the compound. Suitable agents that may act in this capacity include a monoclonal or polyclonal antibody, a protein or a liposome.

The pharmaceutical composition of the invention may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit. One of ordinary skill in the art, without undue experimentation may determine preferred aerosols.

The pharmaceutical compositions of the invention may be prepared by methodology well known in the pharmaceutical art. For example, a pharmaceutical composition intended to be administered by injection can be prepared by combining a compound of the invention with sterile, distilled water so as to form a solution. A surfactant may be added to facilitate the formation of a homogeneous solution or suspension. Surfactants are compounds that non-covalently interact with the compound of the invention so as to facilitate dissolution or homogeneous suspension of the compound in the aqueous delivery system.

The compounds of the invention, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy. Generally, a therapeutically effective daily dose is (for a 70 kg mammal) from about 0.001 mg/kg (i.e. 0.07 mg) to about 100 mg/kg (I.e., 7.0 g); preferably a therapeutically effective dose is (for a 70 kg mammal) from about 0.01 mg/kg (i.e. 0.7 mg) to about 50 mg/kg (i.e., 3.5 g); more preferably a therapeutically effective dose is (for a 70 kg mammal) from about 1 mg/kg (i.e. 70 mg) to about 25 mg/kg (i.e., 1.75 g).

Compounds of the invention, or pharmaceutically acceptable salts thereof, may also be administered simultaneously with, prior to, or after administration of one or more other therapeutic agents. Such combination therapy includes administration of a single pharmaceutical dosage formulation which contains a compound of the invention and one or more additional active agents, as well as administration of the compound of the invention and each active agent in its own separate pharmaceutical dosage formulation. For example, a compound of the invention and the other active agent can be administered to the patient together in a single oral dosage composition such as a tablet or capsule, or each agent administered in separate oral dosage formulations. Where separate dosage formulations are used, the compounds of the invention and one or more additional active agents can be administered at essentially the same time, i.e., concurrently, or at separately staggered times, i.e., sequentially; combination therapy is understood to include all these regimens.

The compounds of the present invention may be administered to an individual afflicted with a disease as described herein, such as a cancer, diabetes or infection with an intracellular bacteria. For in vivo use for the treatment of human disease, the compounds described herein are generally incorporated into a pharmaceutical composition prior to administration. A pharmaceutical composition comprises one or more of the compounds described herein in combination with a physiologically acceptable carrier or excipient as described elsewhere herein. To prepare a pharmaceutical composition, an effective amount of one or more of the compounds is mixed with any pharmaceutical carrier(s) or excipient known to those skilled in the art to be suitable for the particular mode of administration. A pharmaceutical carrier may be liquid, semi-liquid or solid. Solutions or suspensions used for parenteral, intradermal, subcutaneous or topical application may include, for example, a sterile diluent (such as water), saline solution, fixed oil, polyethylene glycol, glycerin, propylene glycol or other synthetic solvent; antimicrobial agents (such as benzyl alcohol and methyl parabens); antioxidants (such as ascorbic acid and sodium bisulfite) and chelating agents (such as ethylenediaminetetraacetic acid (EDTA)); buffers (such as acetates, citrates and phosphates). If administered intravenously, suitable carriers include physiological saline or phosphate buffered saline (PBS), and solutions containing thickening and solubilizing agents, such as glucose, polyethylene glycol, polypropylene glycol and mixtures thereof.

The compounds described herein may be prepared with carriers that protect it against rapid elimination from the body, such as time release formulations or coatings. Such carriers include controlled release formulations, such as, but not limited to, implants and microencapsulated delivery systems, and biodegradable, biocompatible polymers, such as ethylene vinyl acetate, polyanhydrides, polyglycolic acid, polyorthoesters, polylactic acid and others known to those of ordinary skill in the art.

Preparation of the Compounds of the Invention

The compounds of the invention may be prepared by standard organic chemistry synthesis or by recombinant technology.

With respect to standard organic chemistry synthesis, the following Reaction Schemes illustrate methods to make compounds of this invention, i.e., compounds of formula (I):

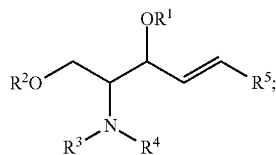

where $R^1$, $R^2$, $R^3$, $R^4$ and $R^5$ are described above in the Summary of the invention for compounds of formula (I), as isolated stereoisomers or mixtures thereof, or as pharmaceutically acceptable salts thereof. In particular, the following Reaction Schemes illustrate methods of preparing compounds of formula (I-1), compounds of formula (I-2), compounds of formula (I-4) and compounds of formula (I-5), as set forth above in the Embodiments of the invention.

It is understood that in the following Reaction Schemes, combinations of substituents and/or variables of the depicted formulae are permissible only if such contributions result in stable compounds.

It will also be appreciated by those skilled in the art that in the processes described below the functional groups of intermediate compounds may need to be protected by suitable protecting groups. Such functional groups include hydroxy, amino, mercapto, and carboxylic acid. Suitable protecting groups for hydroxy include trialkylsilyl or diarylalkylsilyl (for example, t-butyldimethylsilyl, t-butyldiphenylsilyl, or trimethylsilyl), tetrahydropyranyl, benzyl, and the like. Suitable protecting groups for amino, amidino, and guanidino include benzyl, t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acids include alkyl, aryl or arylalkyl esters. Protecting groups may be added or removed in accordance with standard techniques, which are known to one of ordinary skill in the art and as described herein.

The use of protecting groups is described in detail in Greene, T. W. and P.G.M. Wuts, *Greene's Protective Groups in Organic Synthesis* (1999), 3rd Ed., Wiley. As one of skill in the art would appreciate, the protecting group may also be a polymer resin such as a Wang resin, Rink resin, or a 2-chlorotrityl-chloride resin.

It will also be appreciated by those skilled in the art, although such protected derivatives of compounds of this invention may not possess pharmacological activity as such, they may be administered to a mammal and thereafter metabolized in the body to form compounds of the invention which are pharmacologically active. Such derivatives may therefore be described as "prodrugs". All prodrugs of compounds of this invention are included within the scope of the invention.

It is understood that one of ordinary skill in the art would be able to make the compounds of the invention by methods similar to the methods described herein or by methods known to one of ordinary skill in the art. It is also understood that one of ordinary skill in the art would be able to make in a similar manner, as described below, other compounds of formula (I) not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA. etc, or synthesized according to sources known to those skilled in the art (see, for example, Advanced Organic Chemistry: Reactions, Mechanisms, and Structure, 5th edition (Wiley, December 2000)) or prepared as described in this invention.

Preparation of Compounds of Formula (I-1a) and (I-4-a)

Compounds of formula (I-1a) and (I-4-a) are compounds of formula (I), as set forth above in the Summary of the invention, and are prepared as set forth below in Reaction Scheme 1, where X is $—OSO_2Me$, $—OSO_2C_6H_4CH_3$-4, bromo, iodo, or chloro, $R^{6a}$ is $—[CH_2]_6—CH_3$ (for compounds of formula (I-1) or $—[CH_2]_{10}—CH_3$ (for compounds of formula (I-4). Me is methyl, Ph is phenyl, and Pg is a nitrogen-protecting group, preferably t-butoxycarbonyl:

REACTION SCHEME 1

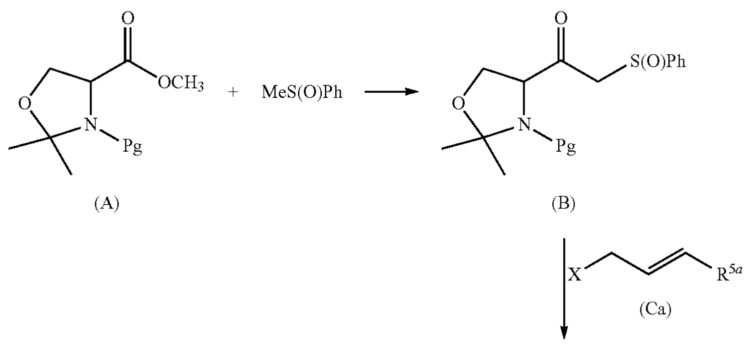

-continued

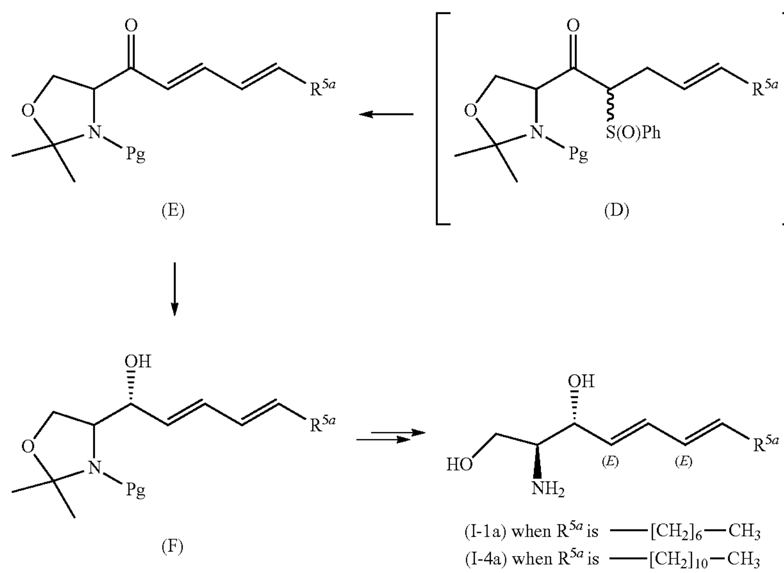

Compounds of formula (A) can be prepared according to methods known to one skilled in the art or by the method disclosed in Gamer, P. et al., *Org. Synth.* 1991, 70: 18-27. Compounds of formula (Ca) can be prepared according to methods known to one skilled in the art or by the method disclosed in Chun, J. et al., *J. Org. Chem.* 2002, 67: 2600-2605.

In general, compounds of formula (I-1a) and (I-4-a) are prepared, as set forth above in Reaction Scheme 1, by first condensing a compound of formula (A) with 2 equivalents of the carbanion of methyl phenyl sulfoxide at −78° C., to give a compound of formula (B), using a procedure set forth in Chun, J. et al., *J. Org. Chem.* 2002, 67:2600-2605. The alkylation of compound of formula (B) with a compound of formula (Ca) is performed in the presence of $K_2CO_3$ in dimethylformamide (DMF) at ambient temperature, using the procedure set forth in Chun, J. et al., *J. Org. Chem.* 2002, 67:2600-2605, to form a compound of formula (E) via the intermediate of formula (D).

Reduction of the compound of formula (E) with a high erythro stereoselectivity can be conducted using reducing agents such as $NaBH_4/CeC_3$ in methanol, DIBAL-H in tetrahydrofuran at a temperature of between about −15° C., to about 0° C., or $NaBH_4$/CsCl to form the erythro intermediate of formula (F). The use of other reducing agents, such as Red-AI or L-Selectride, permits the formation and subsequent isolation of the corresponding threo intermediate (not shown). Acid hydrolysis of the oxazolidine ring and the protecting group on the amino group of compound of formula (F) under standard acid hydrolysis conditions (such as 1 M HCl, 70° C.), affords the erythro compound of formula (I-1a) when $R^{5a}$ is —$[C(H)_2]_6$—$CH_3$ or the erythro compound of formula (I-4-a) when $R^{5a}$ is —$[C(H)_2]_{10}$—$CH_3$.

Compounds of formula (I-3a) and compounds of formula (I-6a), as set forth above in the Embodiments section may be similarly prepared using compounds of formula (Ca) where $R^{5a}$ is —C(H)═C(H)—$[C(H)_2]_6$—$CH_3$ (for compounds of formula (I-3a)) or —C(H)═C(H)—$[C(H)_2]_{10}$—CH, (for compounds of formula (I-6a)). Such compounds of formula (Ca) can be prepared in a manner similar to that which is disclosed in Chun. J. et al.

Preparation of Compounds of Formula (I-2a) and (I-5a)

Compounds of formula (I-2a1) and (I-5a) are compounds of formula (I), as set forth above in the Summary of the invention, and are prepared as set forth below in Reaction Scheme 2, where X is —$OSO_2$Me, bromo, iodo, or chloro, $R^{5b}$ is —$[C(H)_2]_4$—$CH_3$ (for compounds of formula (I-2a1) or —$[C(H)_2]_8$—$CH_3$ (for compounds of formula (I-5a), Cp is η5-cyclopentadienyl, TMS is trimethylsilyl, and Pg is a nitrogen-protecting group, preferably t-butoxycarbonyl:

REACTION SCHEME 2

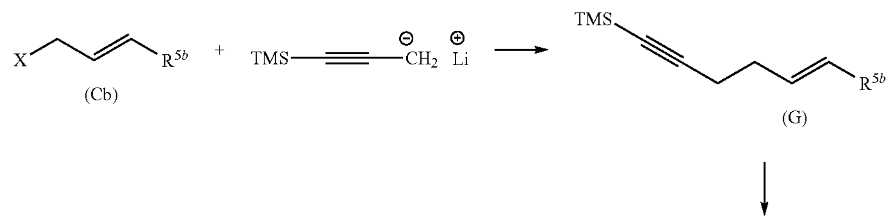

-continued

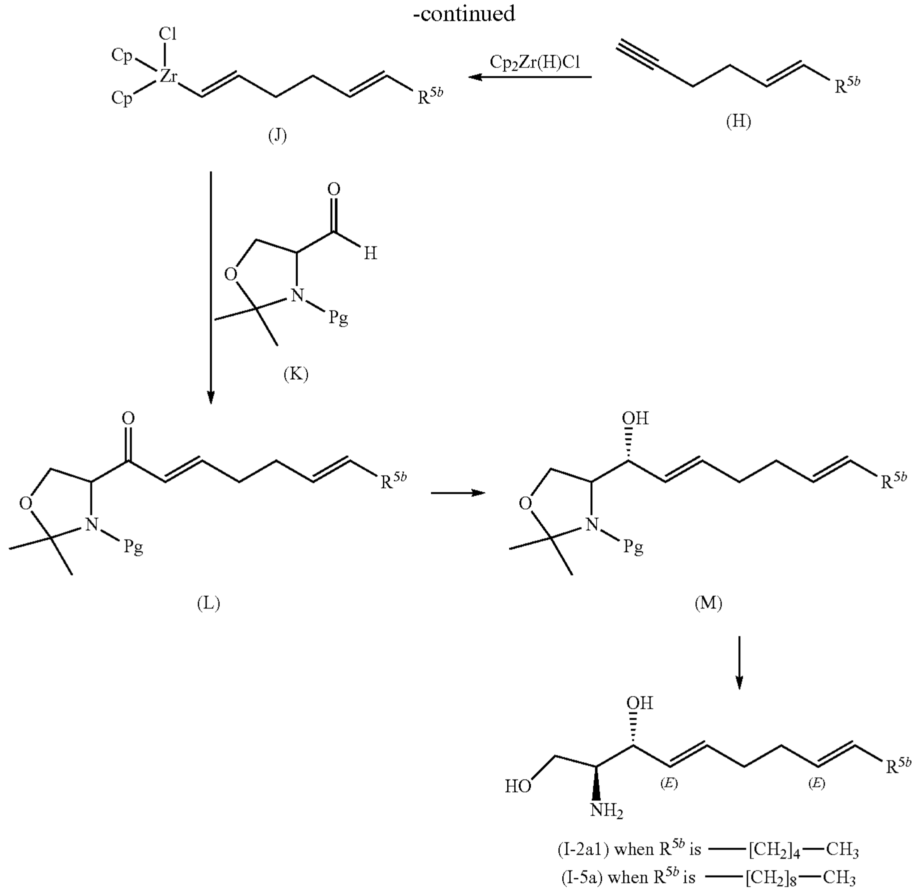

Compounds of formula (Cb) can be prepared according to methods known to one skilled in the art or by the method disclosed in Chun, J. et al. *J. Org. Chem.* 2002, 67: 2600-2605. Compounds of formula (K) can be prepared according to methods known to one skilled in the art or by the method disclosed in Gamer, P. et al., *Org. Synth.* 1991, 70:18-27.

In general, compounds of formula (I-2a1) and (I-5a) are prepared, as set forth above in Reaction Scheme 2, by the methods disclosed in Murakami, T. et al., *Tetrahedron* 2006, 61: 9233-9241 wherein the compound of formula (Cb) is treated with lithiated 1-trimethylsilyl (TMS)-1-propyne to give a compound of formula (G), i.e., a 1-TMS-alkyl-5(E)-en-1-yne. The TMS group in the compound of formula (G) is removed with $Bu_4NF$ in tetrahydrofuran to give the compound of formula (H). The compound of formula (H) is then treated under standard hydrozirconation conditions of a terminal alkyne, such as by treatment with zirconocene chloride hydride ("Schwartz reagent," $Cp_2Zr(H)Cl$, wherein Cp is η5-cyclopentadienyl) (Femandez-Megia, E. *Synlett* 1999, 1179) in tetrahydrofuran, to form the vinyl zirconium organometallic compound of formula (J). The compound of formula (J) is then treated with (S)-Garner's aldehyde of formula (K) in the presence of an excess of zinc bromide in tetrahydrofuran at ambient temperature to form the compound of formula (L) with a high ratio of anti to syn diastereoselectivity.

Reduction of the compound of formula (L) can be performed using reducing agents such as $NaBH_4/CeCl_3$ in tetrahydrofuran/methanol or DIBAL-H in tetrahydrofuran to afford the erythro intermediate of formula (M), or Red-Al or L-Selectride to afford the corresponding threo intermediate (not shown). Acid hydrolysis of the compound of formula (M) under standard acid hydrolysis conditions affords the erythro compound of formula (I-2a1) when $R^{5b}$ is —$[CH_2]_4CH_3$ or the erythro compound of formula (I-5a) when $R^{5b}$ is —$[CH_2]_8CH_3$.

Alternatively, compounds of formula (I-2a1) and formula (I-5a) can be prepared according to the following Reaction Scheme 3 wherein $R^{5b}$ is as defined above for compounds of formula (I-2a1) and formula (I-5a) in Reaction Scheme 2 above and Pg is a nitrogen-protecting group, preferably t-butoxycarbonyl:

REACTION SCHEME 3

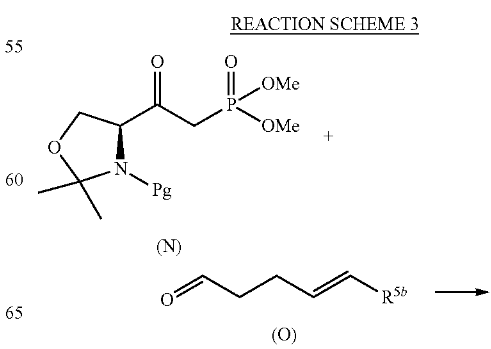

-continued

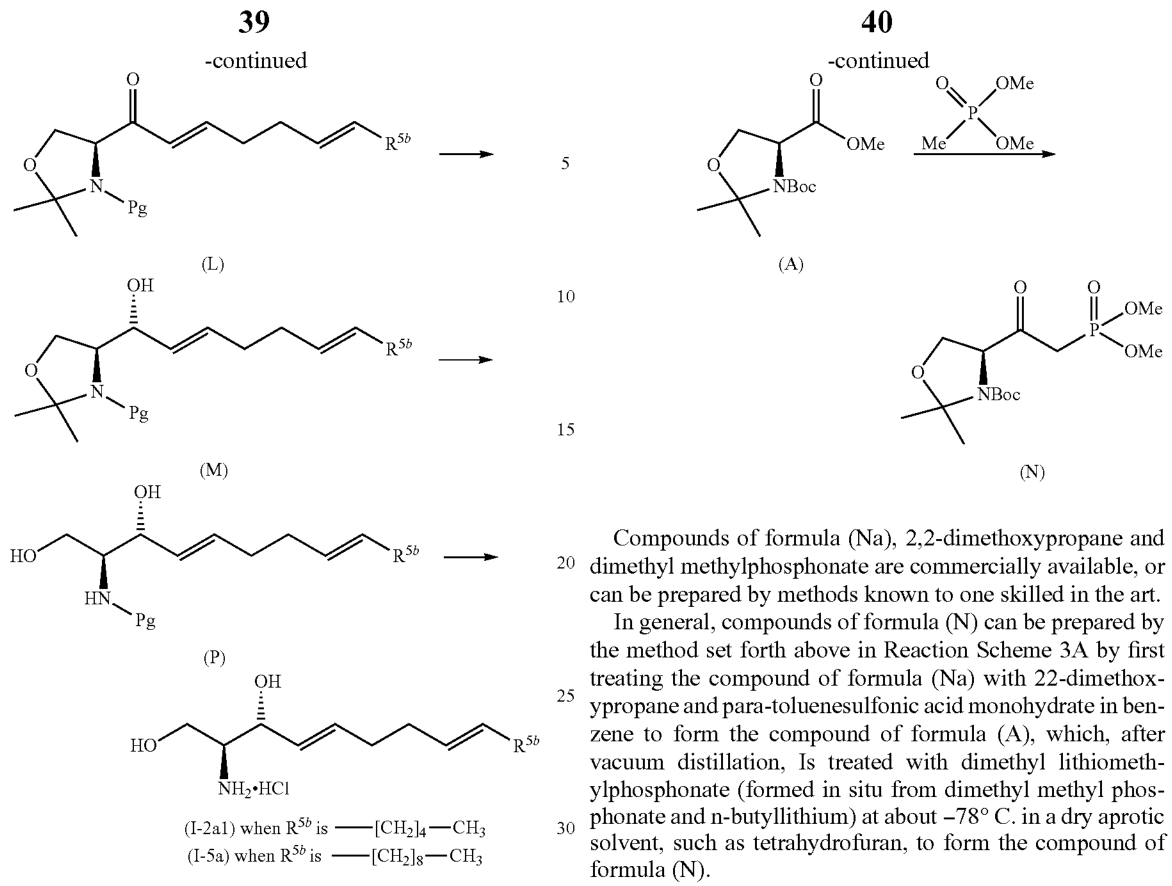

Compounds of formula (N) and formula (O) can be prepared by methods known to one skilled in the art or by the methods disclosed herein.

In general, compounds of formula (I-2a1) and formula (I-5a) are prepared by the method set forth above in Reaction Scheme 3 by first reacting a beta-keto phosphonate compound of formula (N) (after treatment with a base such as $K_2CO_3$ or $Cs_2CO_3$ or $BaCO_3$ in aqueous 2-propanol at ambient temperature) with an aldehyde of formula (O) under Homer-Wadsworth-Emmons (HWE) olefination reaction conditions to afford the compound of formula (L). A stereoselective reduction of the ketone functionality of compound of formula (L) with the appropriate reducing agents (such as sodium borohydride/cesium(III) chloride in tetrahydrofuran/methanol at a temperature of about −80° C. and then warming to about ambient temperature), followed by acid hydrolysis of the N,O-isopropylidene acetal group furnishes the compounds of formula (P), which are then treated under standard deprotecting condtions to form the compound of formula (I-2a1) and formula (I-5a).

Compounds of formula (N) utilized above in Reaction Scheme 3 can be prepared according to the following Reaction Scheme 3A:

REACTION SCHEME 3A

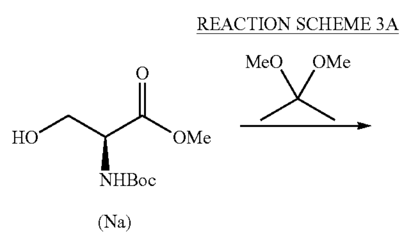

Compounds of formula (Na), 2,2-dimethoxypropane and dimethyl methylphosphonate are commercially available, or can be prepared by methods known to one skilled in the art.

In general, compounds of formula (N) can be prepared by the method set forth above in Reaction Scheme 3A by first treating the compound of formula (Na) with 22-dimethoxypropane and para-toluenesulfonic acid monohydrate in benzene to form the compound of formula (A), which, after vacuum distillation, Is treated with dimethyl lithiomethylphosphonate (formed in situ from dimethyl methyl phosphonate and n-butyllithium) at about −78° C. in a dry aprotic solvent, such as tetrahydrofuran, to form the compound of formula (N).

Compounds of formula (O) utilized above in Reaction Scheme 3 can be prepared according to the following Reaction Scheme 3B, where $R^{5b}$ is as described above for the compounds of formula (I-2a1) and formula (I-5a):

REACTION SCHEME 3B

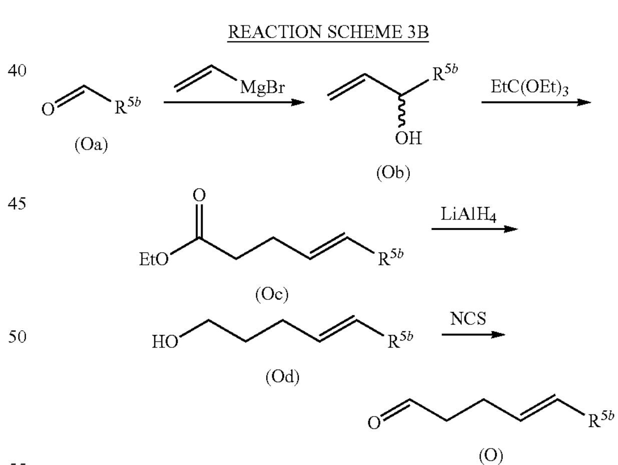

Compounds of formula (Oa), vinyl magnesium bromide and 1,1,1-triethoxyethane (triethyl orthoacetate) are commercially available or can be prepared according to methods known to one skilled in the art.

In general, compounds of formula (O) can be prepared by first treating (Oa) with the Grignard reagent, vinyl magnesium bromide, in an aprotic solvent, such as dry tetrahydrofuran, at a temperature of about −80° C. and then warming to about 30° C., to form a compound of formula (Ob). The compound of formula (Ob) is then treated with an excess of 1,1,1-triethoxyethane for about 7 hours at a temperature of about 140° C. to form a compound of formula (Oc), which is treated with a reducing agent, preferably lithium aluminum hydride, in an aprotic solvent, such as tetrahydrofuran, at a temperature of between about −5° C. to about 30° C., to form a compound of formula (Od), which is then treated with N-chlorosuccinimide at ambient temperature under oxidation conditions using 2,2,6,6-tetramethylpiperidine-1-oxyl (Tempo) and tetra-n-butylammonilum bromide as catalysts in a mixture of dichloromethane and aqueous bicarbonate and carbonate, to produce a compound of formula (O). (See Einhom. J. et al., *J. Org. Chem.* 1996, 61, 7452-7454.)

Preparation of Compounds of Formula (I-3a), (I-6a) and Formula (I-7)

Compounds of formula (I-3a) and (I-6a) are compounds of formula (I), as set forth above in the Summary of the invention, and are prepared as set forth below in Reaction Scheme 4, $R^{5c}$ is —$[C(H)_2]_4$—$CH_3$ (for compounds of formula (I-3a) or —$[C(H)_2]_8$—$CH_3$ (for compounds of formula (I-6a): treatment with $K_2CO_3$ in aqueous 2-propanol or with dry $Cs_2CO_3$ in acetonitrile) with unsaturated aldehydes (containing two carbon-carbon double bonds) of formula (Q) in a Horner-Wadsworth-Emmons (HWE) reaction to afford trienone intermediates of formula (R). A diastereoselective reduction of the ketone functionality with the reducing agents described above (e.g., with sodium borohydride/cesium(III) chloride in tetrahydrofuran/methanol), followed by the removal of the protecting groups, furnishes a sphingosine analog with three double bonds in the long-chain base, i.e., compounds of formulas (1-3a) or compounds of formula (1-6a). Compounds of formula (I-7) are obtained in a similar fashion by use of a substituted cinnamaldehyde of formula (S) as the unsaturated aldehyde in the HWE reaction.

Compounds of formula (I-1a), (I-2a), (I-3a), (I-4-a), (1-5a), and (1-6a) can be further treated with the appropriate etherification, alkylation or acylation agent under conditions known to one skilled in the art (after the appropriate protection of other functional groups, if desired) to produce compounds of formula (I) not exemplified above. In addition, appropriately substituted compounds of formula (Ca) and formula (Cb) wherein $R^{5a}$ is —C(H)═C(H)—$[C(R^8)_2]_6$—$CH_3$ or —C(H)═C(H)—$[C(R^8)_2]_{10}$—$CH_3$ and $R^{5b}$ is —[C

REACTION SCHEME 4

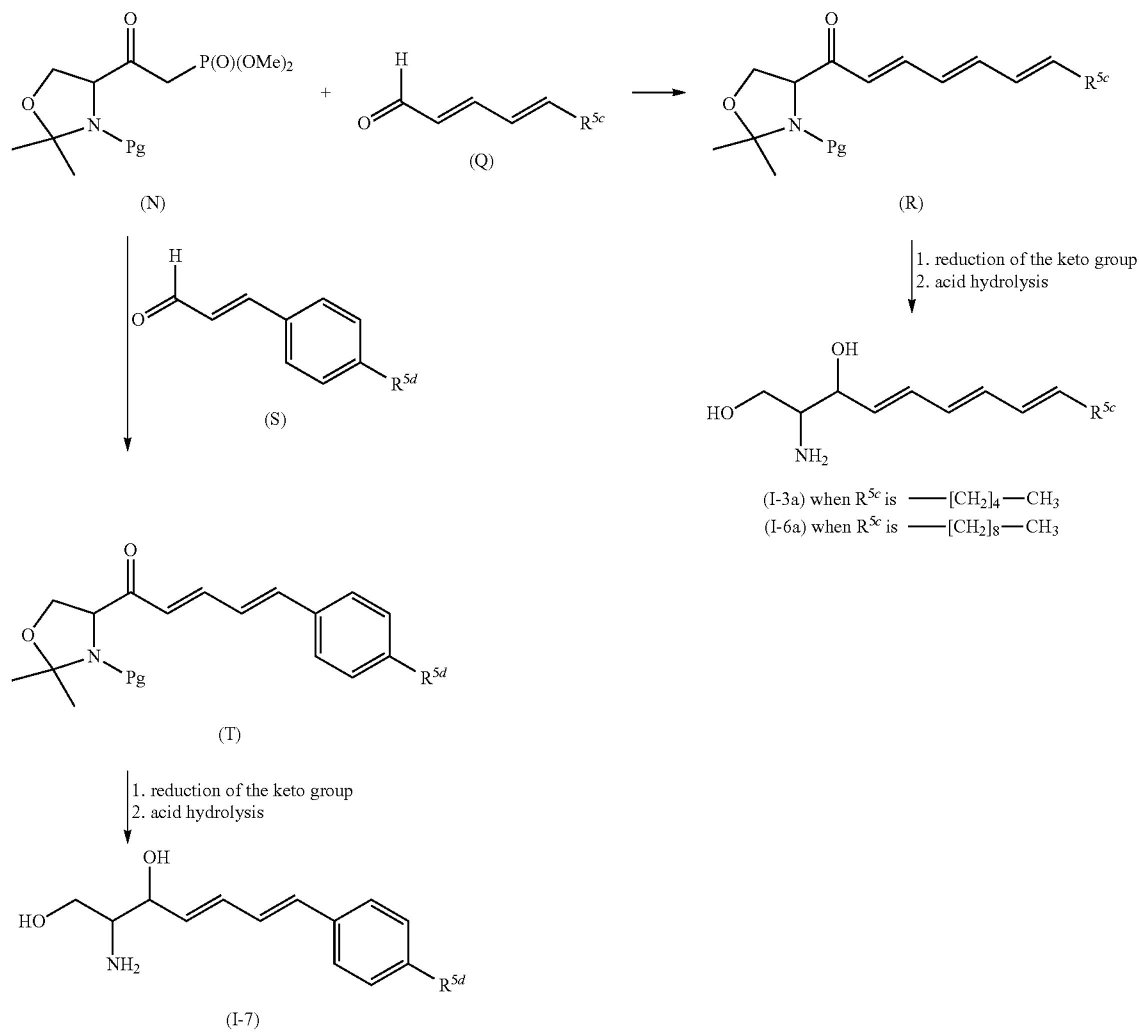

In general, compounds of formula (1-3a) and (1-6a) may be prepared by the treatment of the oxazolidine methyl ester derivative of L-serine with dimethyl lithiomethylphosphonate in tetrahydrofuran to afford its β-ketophosphosphonate intermediate (compound of formula (N)), which reacts (after $(R^8)_2]_6$—$CH_3$ or is —$[C(R^8)_2]_{10}$—$CH_3$ where each $R^8$ is defined as set forth above in the Summary of the invention can be utilized in Reaction Scheme 1 or Reaction Scheme 2 to prepare compounds of formula (I) wherein $R^5$ is selected from the group consisting of —C(H)═C(H)—$[C(R^8)_2]_6$—$CH_3$, —C(H)═C(H)—$[C(R^8)_2]_{10}$—$CH_3$, —$[C(R^8)]_2$—C(H)═C(H)—$[C(R^8)_2]_4$—$CH_3$, —$[C(R^8)]_2$—C(H)═C(H)—$[C(R^8)_2]_8$—$CH_3$, —C(H)═C(H)—C(H)═C(H)—$[C(R^8)_2]_4$—$CH_3$ and —C(H)═C(H)—C(H)═C(H)—$[C(R^8)_2]_8$—$CH_3$, and each $R^8$ can be hydrogen, halo, haloalkyl, alkyl, alkenyl, alkynyl, —$R^9$—$OR^6$, —$R^9$—$OC(O)R^6$, —$R^9$—$S(O)_pR^6$ (where p is 0, 1 or 2), —$R^9$—$C(O)R^6$, —$R^9$—$C(O)OR^6$, —$R^9$—$N(R^6)R^7$ or —$R^9$—$C(O)N(R^6)R^7$, where each $R^6$, $R^7$, and $R^9$ is as defined above in the Summary of the Invention.

All compounds of the invention which exist in free base or acid form can be converted to their pharmaceutically acceptable salts by treatment with the appropriate inorganic or organic base or acid by methods known to one of ordinary skill in the art. Salts of the compounds of the invention can be converted to their free base or acid form by standard techniques known to one skilled in the art.

In vitro Production of Compounds of Formula (I)

In addition to above synthetic methods, certain compounds of the invention may be produced in vitro in an appropriate host cell. For example, synthesis of C14Δ-4,6 sphingadienes (i.e., compound of formula (I-1) as set forth above in the Embodiments Section) from precursor lipids in *Drosophila* is likely through the Introduction of a second double bond into an appropriate precursor long chain base by a sphingolipid desaturase or fatty acid desaturase. Thus. In certain embodiments, a sphingolipid desaturase and/or fatty acid desaturase may be expressed recombinantly in an appropriate cell line (e.g., *Drosophila melanogaster* S2 and CI.8 cells) and sphingadiene compounds isolated from these cell lines (see e.g., J. Biol. Chem. 2002. 277(:25512-25518; Curr. Microbiol. 2002, 45:459-461: FEBS Lett. 2003, 538:192-196; Mol. Microbiol. 2006, 62: 1507-1514; Biochim. Biophys. Acta 2007, 1771:271-285).

In this regard, lipid extracts in the context of the present invention can be isolated using any number of procedures known in the art. For example, samples containing 50 mg of frozen intact fly material or isolated fly tissues or cells may be placed in a glass Potter Elvehjem homogenizer. Twenty microliters of an internal standard mixture containing 200 pmol of each C17-sphingosine (Avanti Polar Lipids, Alabaster, Ala.) and C17-sphingosine-1-phosphate (Matreya Inc., Pleasant Gap, Pa.) are then added and fly materials are homogenized in 0.5 ml of methanol until pestle moved smoothly. An equal volume of water is then added and homogenization continued with another 10 strokes. Fly homogenates may be transferred to a glass tube and a two phase separation obtained after the addition of 1 ml of chloroform and 0.75 ml of 1 M ammonium hydroxide followed by vortexing and centrifugation. For the analysis of long chain base phosphates (LCBPs) the water phase is recovered, dried, and resuspended in methanol/water 1:1 (v/v). For the analysis of long chain bases (LCBs) a portion of the organic phase is recovered, dried, and resuspended in the appropriate volume of methanol. After hydrolysis, a two-phase separation is obtained and the organic phase recovered.

The following specific Biological Examples are provided as a guide to assist in the practice of the invention, and are not intended as a limitation on the scope of the invention.

EXAMPLES

Example 1

Sphingadiene Compounds Elicit Apoptosis in Cancer Cells

To assess the effect of C14 sphingadienes on colon cancer cell viability, HT29, DLD1 and SW480 colon cancer cells (available from American Type Culture Collection (ATCC), Manassas, Va.) were propagated in DME-H21 plus 10% serum until ⅔ confluent. Media was then replaced with serum-free media containing 10 μM sphingadienes (SD). After 24 hours, cells were harvested, and whole cell extracts were prepared for caspase-3 activity assays. Caspase-3 activity was determined using substrate Ac-DEVD-pNA (Biomol. Plymouth Meeting, Pa.) as described (Oskouian, B., et al., Proc Natl Acad Sci USA 103: 17384-17389, 2006).

HT29, HCT116 and SW480 colonic epithelial cell lines were chosen for study because their growth has been shown previously to be affected by sphingolipids, and they have upregulation of the Wnt and AKT signaling pathways (see Ahn, E. H. and Schroeder. J. J., Exp Biol Med (Maywood) 227(5): 345-353., 2002; Ilyas, M., et al., Proc Natl Acad Sci USA 94: 10330-10334, 1997.; Huang, X. and Guo, B., Cancer Res 66: 9245-9251, 2006)

As shown in FIG. 1, sphingadiene (Sd) treatment induced apoptosis in HT29 cells (and DLD1. SW480 cells, not shown). The effect was time- and dose-dependent (data not shown).

Effect of SDs on non-malignant colonic epithelium is tested using FHC and CCD 841 CoN transformed colonic epithelial cell lines. Cells are cultured in DME-H21 plus 10% serum or serum-free with SD. FHC line is grown in Ham's F12, 45%; DMEM, 45%; 25 mM HEPES: 10 ng/ml cholera toxin; 0.005 mg/ml insulin; 0.005 mg/ml transferrin; 100 ng/ml hydrocortisone; fetal bovine serum, 10% and CCD 841 is grown in ACL-4 medium. Transfections are performed using FuGene HT reagent according to the manufacturer's instructions.

Example 2

Sphingadienes Inhibit Cytosolic Translocation of AKT and Activate PTEN

To address the possibility that sphingadienes might promote cell death by inhibiting the $PI_3K$/AKT pathway, the effect of sphingadienes on phosphorylation of AKT, PTEN, and the AKT substrate 4EBP, which is a regulator of protein translation, was evaluated using immunoblotting of whole cell extracts. The results showed that within hours of treatment with sphingadienes, AKT and 4EBP phosphorylation were diminished, whereas PTEN phosphorylation (and activation) was increased.

To determine if AKT phosphorylation was prevented due to its failure to translocate to the membrane, the effect of sphingadlenes on AKT and phospho-AKT protein content in membrane versus cytosol of HT29 cells treated with insulin (which promotes AKT translocation to the membrane) was examined. The results of immunoblot analysis of cell membrane and cytosol fractions of Insulin-treated cells showed that AKT translocation and phosphorylation were prevented by sphingadlene treatment, whereas a myristoylated, constitutively membrane-bound and active AKT (AKT-myr) was unaffected by sphingadienes. Further, AKT-myr could protect against sphingadiene-induced cell death as shown previously in FIG. 1.

The inhibition of AKT membrane translocation by sphingadienes was confirmed by fluorescence microscopy studies of Hela cervical carcinoma cells transiently transfected with a GFP-AKT-pleckstrin homology domain (PHD)-domain fusion construct which contains the lipid-sensing AKT domain. For this experiment, cells were transfected with constructs for GFP-PHD or GFP-Akt-Myr. After 36 hours, the medium was changed to serum-free medium plus sphingadiene and cells were incubated for 9 hours followed by treatment with 10 μg/ml insulin for 1 hour. Fluorescent microscopy was then performed on a Zeiss Axiovert 25 equipped with a Diagnostic spot digital camera.

Figure 2:
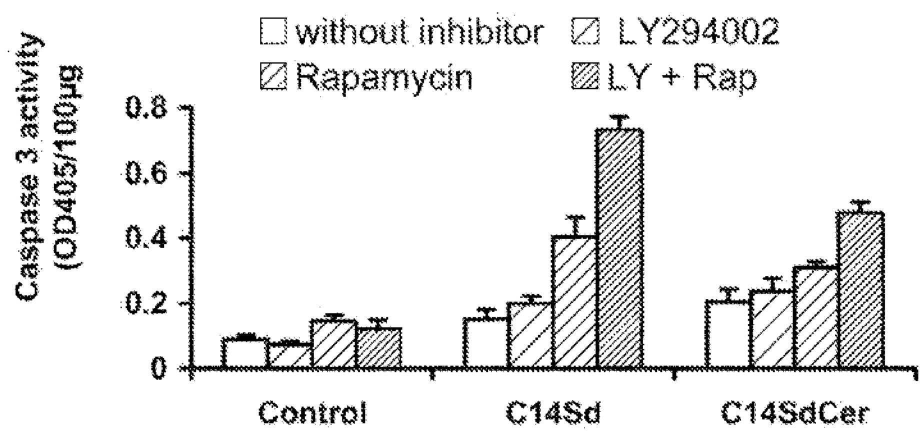
FIG. 2 is a bar graph showing that sphingadienes are synergistic with mTOR inhibitor, rapamycin and $PI_3K$ inhibitor LY294002 in inducing apoptosis in HT29 colon cancer cells in vitro and were more effective than sphigadiene-C2-ceramides. Caspase 3 activity was measured as described in Example 1.

Additional studies also confirmed that sphingadiene inhibition of AKT signaling leads to decreased protein translation in HT29 cells and that sphingadienes are synergistic with mTOR inhibitor, rapamycin and $PI_3K$ inhibitor LY294002 (but not MAPK or JNK inhibitors) in inducing apoptosis in HT29 colon cancer cells in vitro and were more effective than sphigadiene-C2-ceramides (see FIG. 2).

Example 3

Sphingadiene Compounds Inhibit Sphingosine Kinase

Figure 3:
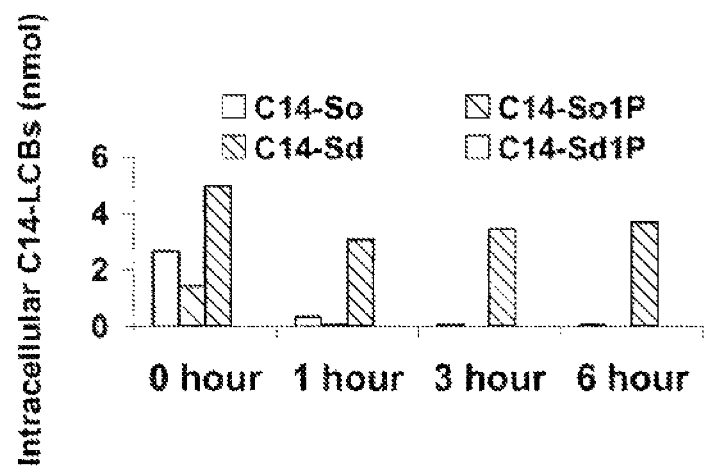
FIG. 3 is a bar graph showing sphingadiene (SD) metabolism in HT29 colon cancer cells. Cells were incubated briefly with C14 SD or C14 sphingosine (So). By 15 minutes, SD, So and C14 So1P were detected by LC-MS (as shown at 0 h), but no phosphorylated C14 SD were found. After lipid removal. So and So1P were rapidly metabolized, but SD remained for 6 hrs. Competition studies with So and SD indicate SD inhibit SK (not shown).

In this example, the uptake and metabolism of C14 sphingadienes was compared with that of synthetic C17 sphingosine (as a substitute for endogenous C18 sphingosine which is already present in cells) and C14 sphingosine (to assess the importance of the second double bond) by HT29 colon cancer cells. Toward that end, cells were incubated with 10 μM sphingadiene in serum-free media, followed by cell harvest at various time points, lipid extraction and analysis by mass spectrometry of SD, SD-phosphate, C14 sphingosine and corresponding S1Ps. The results showed that C14 sphingosine and C14 SDs were taken up at equal rates (FIG. 3) but both faster than long chain sphingosine (not shown). However, whereas C14 sphingosine was rapidly converted to S1P and cleared from the cells in hours, C14 SDs were not converted to SD-phosphates and remained in the cells for many hours. These results suggest that SD molecules may serve as poor substrates of SK. Additional studies with both sphingosine and SD suggest that SDs likely inhibit SK.

Example 4

Figure 4:
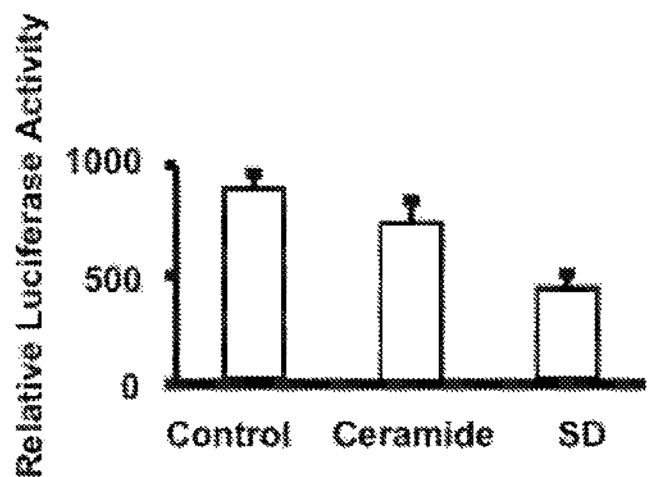
FIG. 4 is a bar graph showing β-catenin/TCF transcriptional activity in cells exposed to sphingadienes. Cells were treated with 10 μM lipid or vehicle for 24 h. Luciferase activity was determined as described in Example 4.

Sphingadienes Induce Translocation of β-Catenin from the Nucleus to the Cytoplasm The Wnt signaling pathway is another critical hub in the pathogenesis of colon cancer. Using immunofluorescent detection of β-catenin in sphingadiene-treated SW480 and HT29 cells, experiments showed that, in addition to disrupting PI3K/AKT signaling, sphingadiene treatment disrupted Wnt signaling by inducing translocation of β-catenin from the nucleus (where β-catenin resides in these cells due to mutations of APC) to the cytoplasm. Similarly, results from reporter assays using β-catenin/T-cell factor (TCF) reporter plasmid (TOPFLASH system from Upstate, now part of Millipore, Billerica, Mass.), performed on extracts of SW480 cells showed that sphingadiene effects on I-catenin localization correlated with 50% reduction in TCF gene transcription see FIG. 4). For these experiments, cells were transfected with the TOPflash TCF reporter plasmid (Upstate, now part of Millipore. Billerica, Mass.), which contains three copies of the TCF binding site upstream of a TK minimal promoter and luciferase open reading frame. The FOPflash vector, which contains mutated TCF binding sites, served as a negative control.

Example 5

Sphingadienes are Cytotoxic to Human Colon Cancer Cells

In this Example, the effects of sphingadienes on colon cancer cell lines were further tested.

Figure 5A:
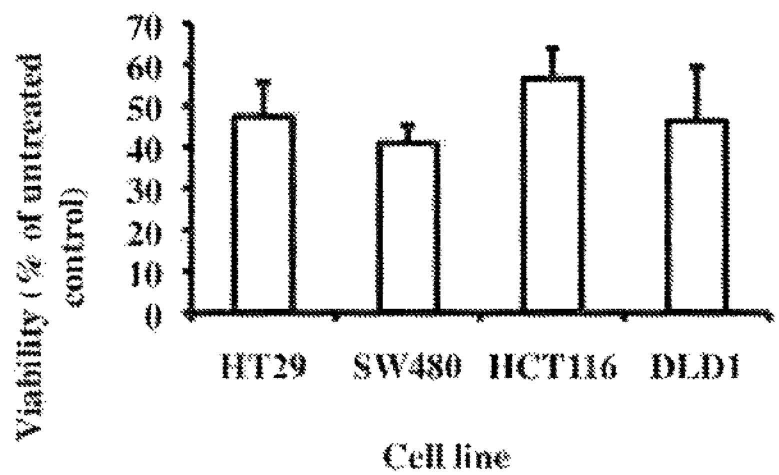
FIG. 5A is a bar graph showing viability of human colon cancer cell lines, HT29, SW480, HCT116 and DLD1 after exposure to 10 μM C14Δ4:6Sd.

The human colon cancer cell lines, HT29, SW480, HCT116 and DLD1 were treated with 10 μM C14Δ4:6Sd (also referred to herein as 2-aminotetradeca-4,6-diene-1,3-diol) and viability was determined at 24 hours. As shown in FIG. 5A, the viability for the treated HT29, SW480 and DLD1 cells was below 50% of controls after 24 hours of exposure and just above 50% of controls in the HCT116 cell line.

Figure 5B:
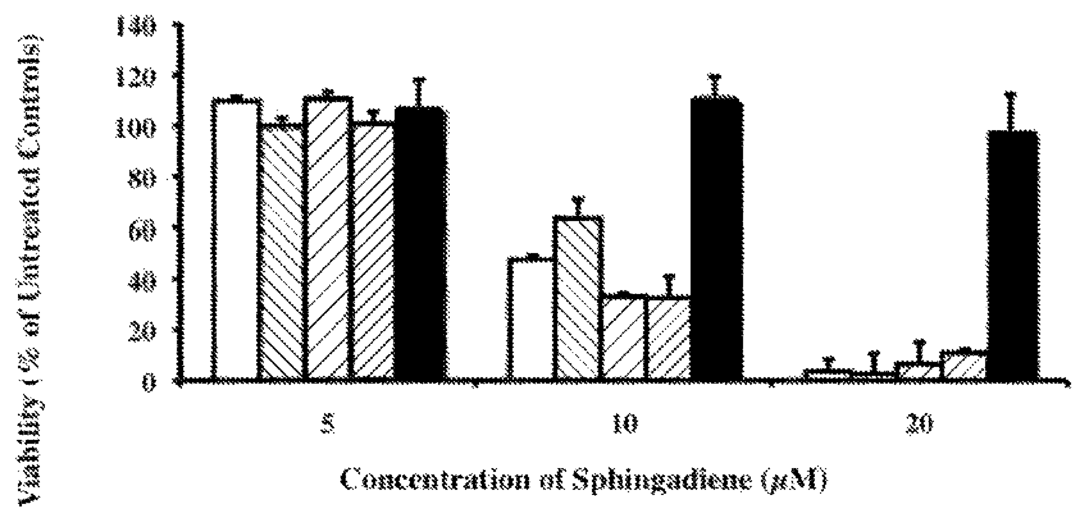
FIG. 5B is a bar graph showing viability of HT29 cells incubated with various sphingadiene compounds at various concentrations.

HT29 cells were then incubated with various sphingadiene compounds and viability was determined at 24 hours. As shown in FIG. 5B, C14Δ4:6Sd, C14Δ4:8 Sd, C18Δ4:6Sd and C18Δ4:8 Sd were all cytotoxic to the HT29 colon cancer cell line.

Figure 5C:
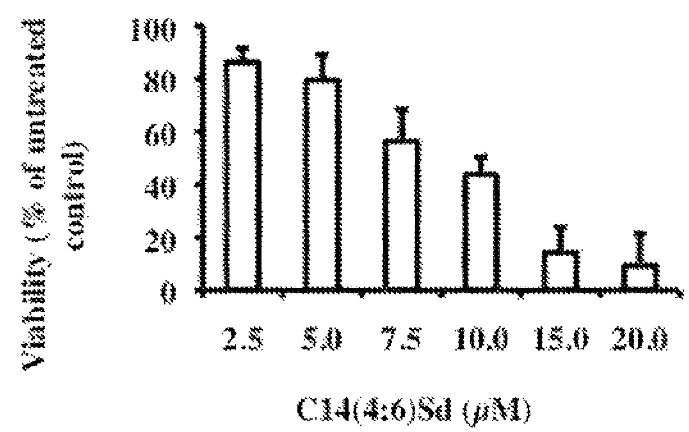
FIGS. 5C and 5D are bar graphs showing viability of HT29 cells incubated with various concentrations of C14Δ4:6Sd (FIG. 5C) or with 10 μM C14Δ4:6Sd for various time periods (FIG. 5D).
Figure 5D:
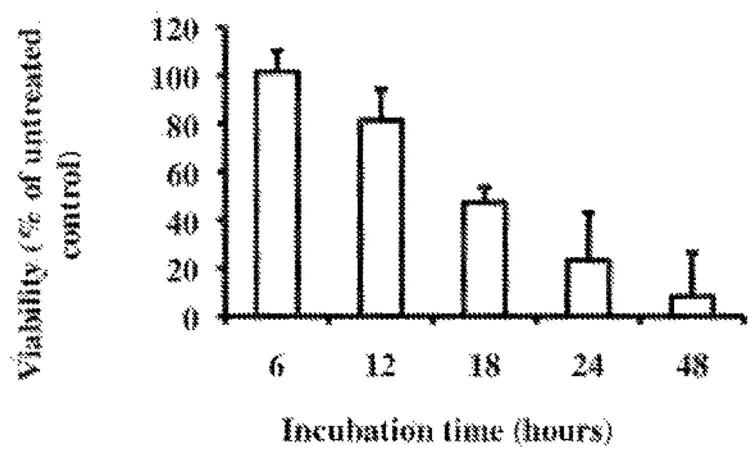

HT29 cells were incubated with various concentrations of C14Δ4:6Sd and viability was determined at 24 hours or incubated with 10 μM C14Δ4:6Sd and viability was determined at various time points. As shown in FIGS. 5C and 5D, the cytotoxicity effect was dose- and time-dependent.

Example 6

C14Δ4:6Sd Induced Autophagy And Apoptosis in Human Colon Cancer Cells

Autophagy is a cell process used to degrade components of the cytoplasm and functions as a cell survival mechanism during nutrient deprivation (P. Codogno and A J Meijer, Cell Death Differ. 2005 November; 12 Suppl 2:1509-18). Formation of what appeared to be organelle-like structures was observed in cells exposed to sphingadienes. In order to further investigate this phenomenon, LC3 (microtubule associated protein 1 light chain 3) was used as a marker for this process. In particular, LC3 is found in two forms, LC3-1 and LC3-2, and tracking the conversion of LC3-1 to LC3-2 is a marker for autophagic activity.

In one experiment, SW480 cells were transfected with a GFP-LC3 construct and treated for 4 h with 5 μM C14Δ4:6Sd. Fluorescence microscopy to detect the presence of GFP-LC3 showed autophagosome formation in cells exposed to 5 μM C14Δ4:6Sd. In another experiment, SW480 cells transfected with myr-Akt were treated with various concentrations of C14Δ4:6Sd and the amount of LC3 activation (shift from LC3-1 to LC3-2) was verified by western blotting. These results confirmed the occurrence of autophagic activity that was observed by microscopy.

Figure 6A:
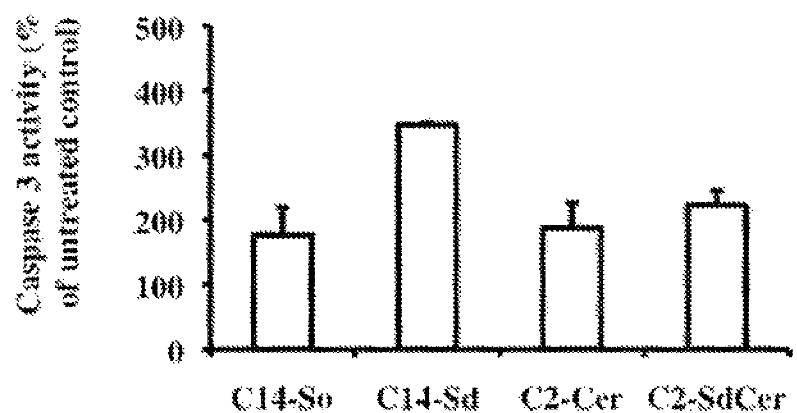
FIGS. 6A and 6B are bar graphs showing Caspase 3 activity, indicating that sphingadienes induce apoptosis in HT29 cells.

In an additional experiment, HT29 cells were treated with 10 μM sphingoid bases or ceramides and caspase-3 activity was determined at 24 hours. Confirming the results of Example 1, FIG. 6A shows that sphingadienes induced apoptosis in the HT29 colon cancer cell line as indicated by the increase in caspase-3 activity.

Figure 6B:
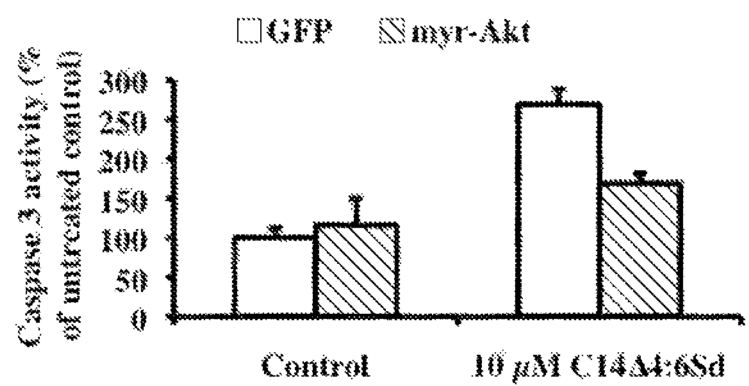

HT29 cells transfected with constitutively active myristoylated Akt (myr-Akt) were treated with 10 μM C14Δ4:6Sd and caspase 3 activity was determined at 24 hours. As shown in FIG. 6B, myristoylated, constitutively membrane-bound and active AKT (myr-AKT) was unaffected by sphingadienes and protected against sphingadiene-induced cell death, as also shown in FIG. 1.

Example 7

C14Δ4:6Sd Inhibited Signaling Through the Akt Pathway

Figure 7A:
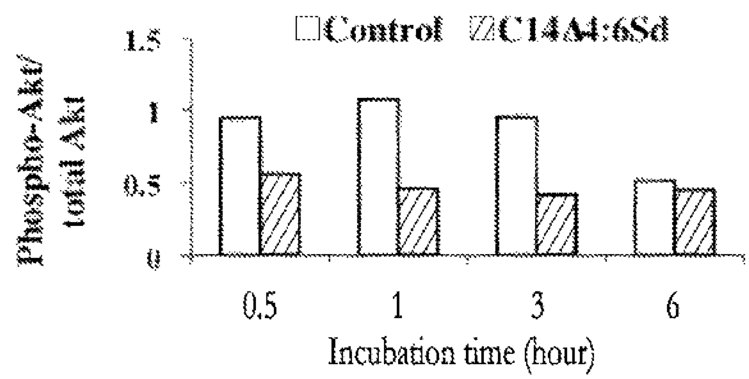
FIGS. 7A and 7B are bar graphs showing the level of phosphorylated Akt or 4EBP in HT29 cells exposed to C14Δ4:6Sd.
Figure 7B:
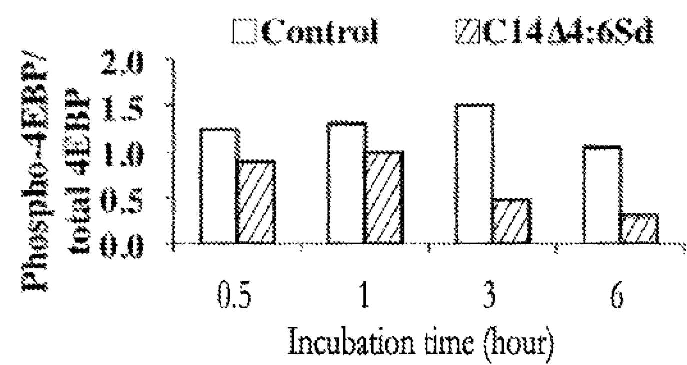

HT29 cells were incubated with 10 μM C14Δ4:6Sd for 0.5, 1, 3, 6 and 24 hours and the level of Akt and 4EBP phosphorylation was evaluated at each time point by western blotting. The results showed that sphingadienes inhibited phosphorylation of Akt and 4EBP in a time-dependent manner. The ratios of phosphorylated Akt to total Akt and of phosphorylated 4EBP to total 4EBP, were quantified by densitometry using ImageJ software (ImageJ is a public domain Java image processing program inspired by NIH Image; available at rsbweb.nih.govlij/index.html) and are shown in FIG. 7A and FIG. 7B, respectively. Similar experiments where SW480 cells were incubated with 10 μM C14Δ4:6Sd for up to 5 hours and analyzed by Western blotting showed that reduced phosphorylation of 4EBP over time also occurred in this cancer cell line when exposed to sphingadienes.

In an additional experiment, HT29 cells were treated for various time periods with 10 μM C14Δ4:6Sd or C18Δ4:8 Sd and the level of phosphorylation of Akt and 4EBP was evaluated by western blotting at 0.5, 1.0 and 3.0 hours. The results confirmed that sphingadienes inhibited phosphorylation of Akt and 4EBP, even at 0.5 hours of exposure, thus inhibiting signaling through Aid and 4EBP.

Example 8

C14Δ4:6Sd Inhibited Akt Signaling and Protein Synthesis

Figure 8A:
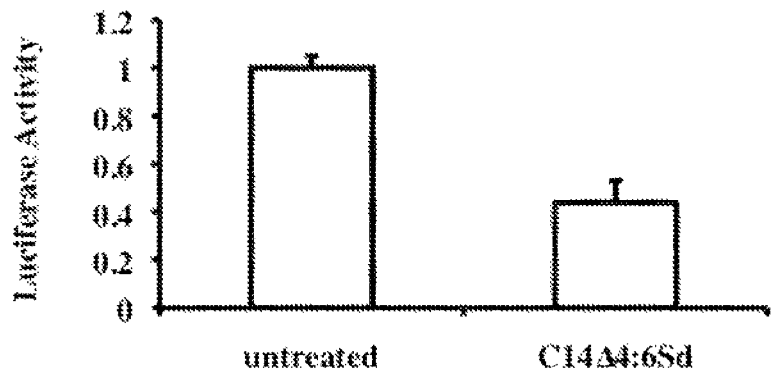
FIG. 8A is a bar graph showing luciferase activity in C14Δ4:6Sd treated and control cells.
Figure 8B:
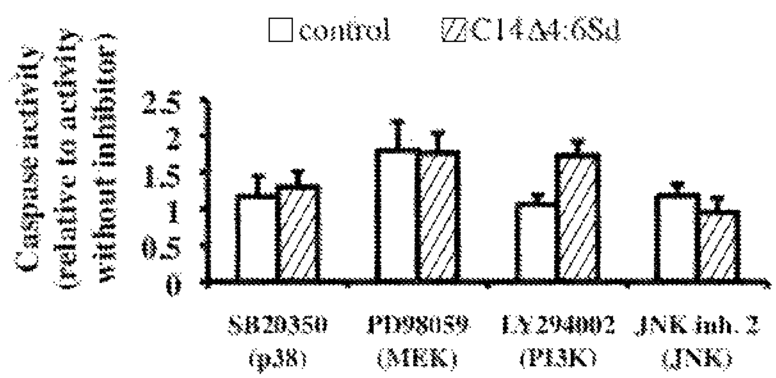
FIG. 8B is a bar graph showing Caspase activity relative to activity without the noted inhibitors, in controls and in cells treated with C14Δ4:6Sd.

HT29 cells were incubated for 6 hours with 10 μM C14Δ4:6Sd and the translational activity of the cell cytosol was measured with the DUAL-LUCIFERASE® Reporter Assay System (Promega, Madison, Wis.). As shown in FIG. 8A, Luciferase activity was reduced by more than half in the presence of 10 μM C14Δ4:6Sd demonstrating that C14Δ4:6Sd inhibited protein synthesis. In another experiment, HT29 cells were pretreated with inhibitors of p38 (SB20350), MEK (PD98059), $PI_3K$ (LY294002) and JNK (JNK inhibitor 2) and caspase 3 activity was determined following an 18 hour incubation with 10 μM C14Δ4:6Sd. The results shown in FIG. 8B show that sphingadienes were synergistic with $PI_3K$ inhibitor LY294002, confirming previous experiments shown in FIG. 2, but were not synergistic with p38, MEK or JNK inhibitors.

Figure 8C:
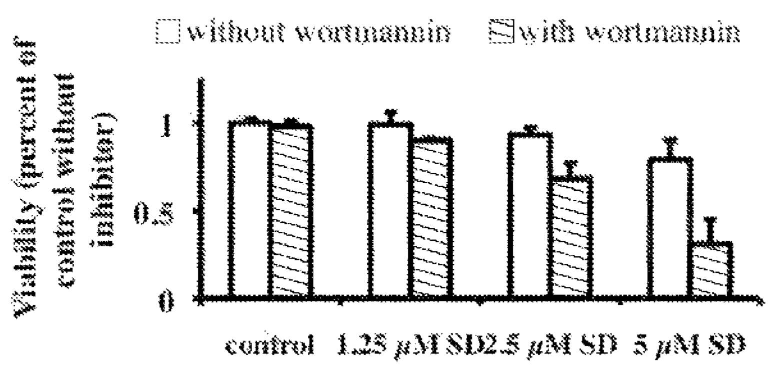
FIG. 8C is a bar graph showing viability of HT29 cells (as a percent of control cells without inhibitor) of cells exposed to varying concentrations of C14Δ4:6Sd.

In a further experiment, HT29 cells were treated with the $PI_3K$ inhibitor wortmannin and various concentrations of C14Δ4:6Sd and viability was determined at 24 hours by MTT assay. The results confirmed synergistic inhibition of $PI_3K$ by C14Δ4:6Sd and wortmannin (see FIG. 8C).

Example 9

Figure 9A:
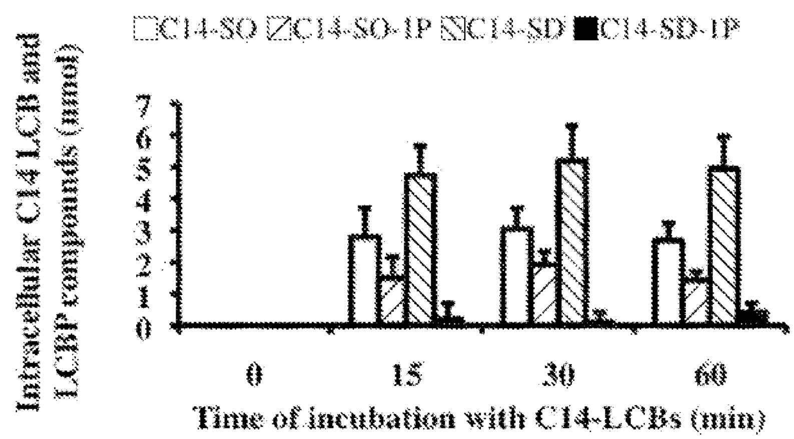
FIGS. 9A and 9B are bar graphs showing intracellular levels of C14LCB and LCBP compounds in cells exposed to sphingosine or C14Δ4:6Sd.
Figure 9B:
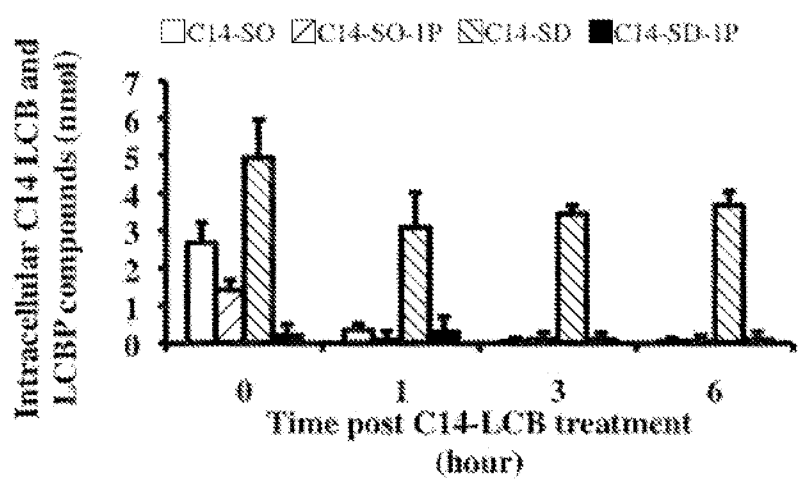

Metabolism of C14Δ4:6Sd Was Less Effective than the Corresponding C14A4So Compound in HT29 Colon Cancer Cells HT29 cells were incubated for 0.25 hours, 0.5 hours and 1 hour in media containing 10 μM C14-So (Δ4) (sphingosine) or C14Δ4:6Sd (see FIG. 9A). HT29 cells were incubated for 1 hour in media containing 10 μM C14-So or C14Δ4:6Sd. Media was then removed and cells were incubated without lipids for 1, 3 and 6 hours (FIG. 9B). At each time point, cells were harvested, lipids were extracted and the cellular contents of C14-So or C14Δ4:6Sd and the corresponding phosphorylated compounds were analyzed by LC-MS.

As shown in FIG. 9A, C14-So was efficiently phosphorylated while the C14Δ4:6Sd was not. Similarly, as shown in FIG. 9B, after 1 hour incubation without lipids, almost all C14-So and its metabolite were completely metabolized while much of the C14Δ4:6Sd remains unaltered after even 6 hours. Thus, metabolism of the sphingadiene compound was less effective than metabolism of the corresponding C14 sphingosine compound in these cells.

Example 10

C14Δ4:6Sd Phosphorylation By Sphingosine Kinase 1

Further experiments to investigate the metabolism of sphingadienes showed that, in fact these compounds were metabolized in an in vitro lysate system.

Figure 10A:
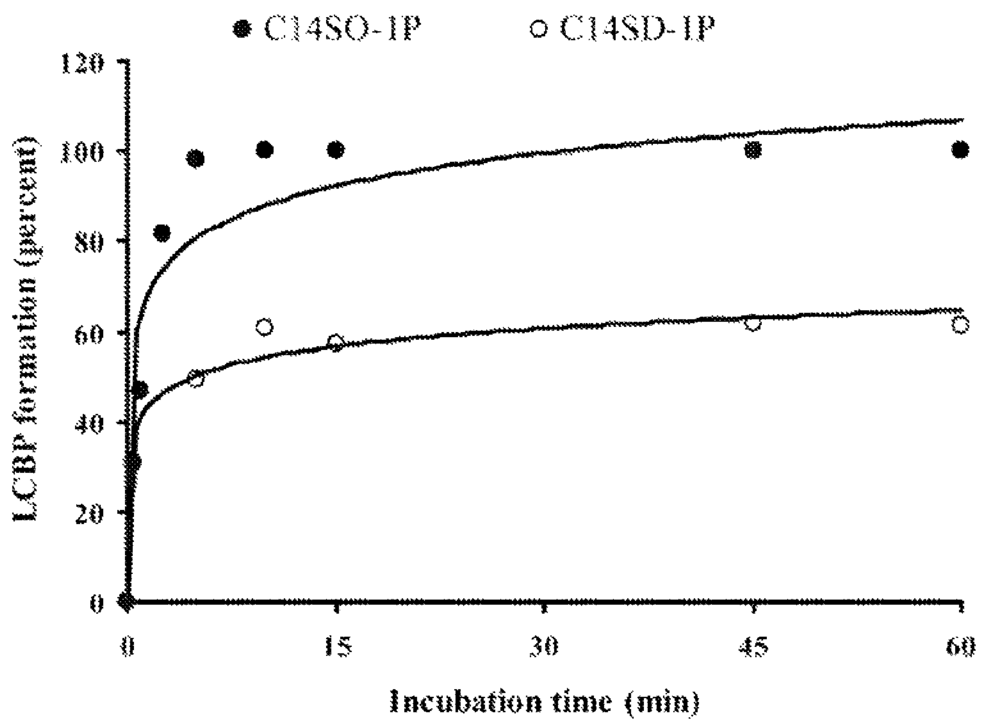
FIG. 10A shows levels of C14SO-1P or C14CD-1P formation in an in vitro cell lysate assay.

In order to test whether C14Δ4:6Sd was phosphorylated by SK1, cell extracts from HEK293 cells overexpressing murine Sphingosine Kinase 1 (SK1) were incubated with C14-So or C14Δ4:6Sd for different time periods (FIG. 10A). The formed phosphorylated sphingoid base products were measured by HPLC. As shown in FIG. 10A, C14Δ4:6Sd was phosphorylated by SK1 in this in vitro cell lysate system.

Figure 10B:
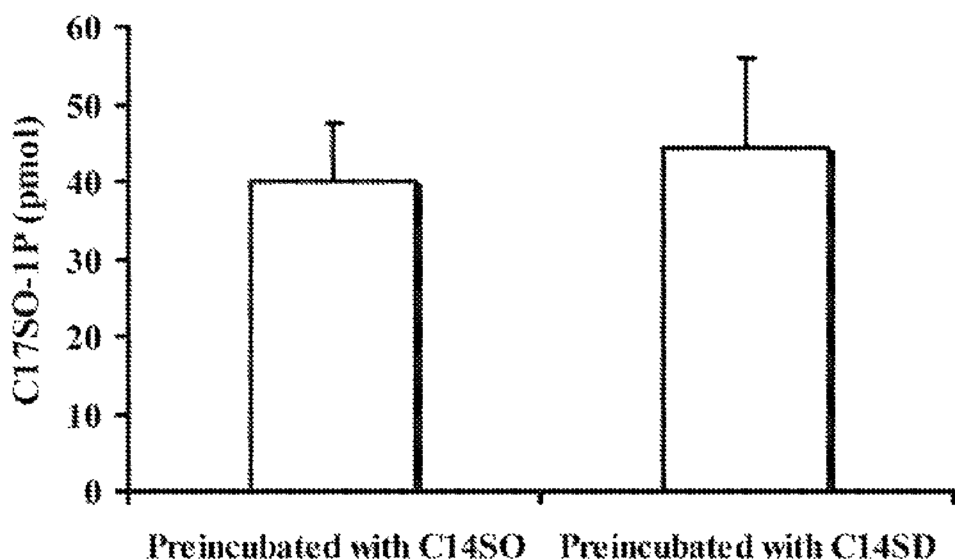
FIG. 10B is a bar graph showing C17SO-1P levels in lysates preincubated with C14SO or C14SD.

In order to test if preincubation with C14-So or C14Δ4:6Sd has an inhibitory effect on the ability of the SK enzyme to phosphorylate the C17-So compound, cell extracts were preincubated for 10 minutes with either C14-So or C14Δ4:6Sd followed by C17-So. As shown in FIG. 10B, no inhibitory effect was observed.

Further experiments in HEK 293 cells that overexpressed human Sphingosine-1-Phosphate Lyase (SPL) and that were incubated with C14So-1P and C14Δ4:6Sd-1P showed that C14Δ4:6Sd-1P was cleaved by SPL. No significant difference was observed in the processing of C17So-1P following preincubation with either C14So-1P or C14Δ4:6Sd-1P.

Thus, using cell lysates, the sphingadiene compounds were phosphorylated by SK and then cleaved by SPL, similar to endogenous sphingosine compounds. Without being bound by theory, it is believed that in intact cells, the introduced sphingadienes may localize to a part of the cell where SK and SPL are not able to reach it, thus explaining the discrepancy between the results of the cell-based and lysate-based experiments.

Example 11

Figure 11A:
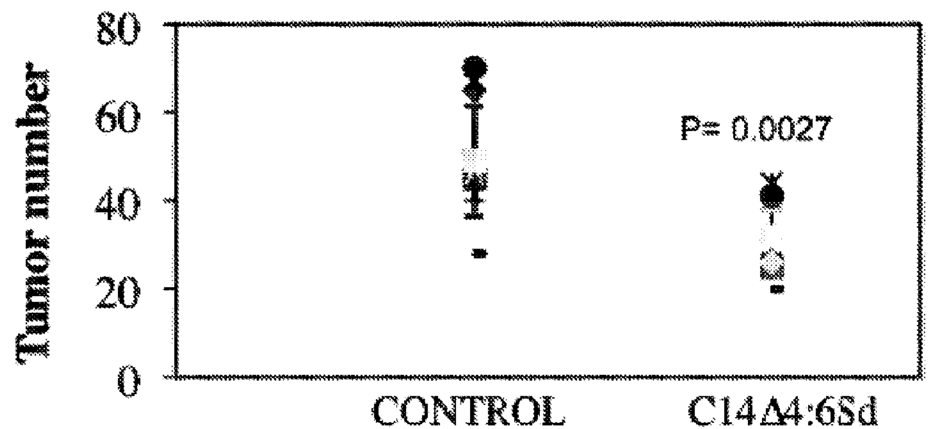
FIG. 11A is a graph showing tumor number in control mice and in mice exposed to C14Δ4:6Sd.
Figure 11B:
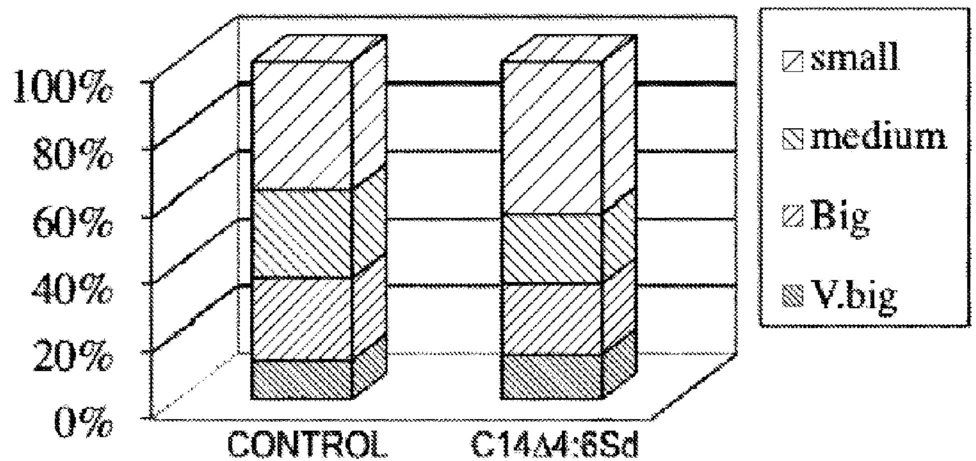
FIG. 11B is a bar graph showing mean tumor size in control and treated mice. Small=<1 mm; medium=1-2 mm; big=2-3 mm; very big=>3 mm.

Treatment of Apc (Min) mice with C14Δ4:6Sd Reduced the Number And Size Of Intestinal Polyps Murine experiments were performed to investigate the in vivo effect of C14Δ4:6Sd on the development of polyps in intestinal tissue using an established animal model system having an inherited genetic defect underlying spontaneous multiple Intestinal neoplasia (Min) (Polakis, 1997 *Blochim Blophys. Acta.* 1332:F127; Kucherlapati et al., 2001 *Semin. Canc. Blot.* 11:219; Sansom et al., 2004 *Genes Dev.* 18:1385). Ten 12 week-old male ApcMin/+ mice (available from Jackson Laboratory. Bar Harbor, Me.) were administered by gavage 2.5 mg/day C14Δ4:6Sd and ten mice received vehicle control. Mice were euthanized by $CO_2$ asphyxiation and intestinal tissues harvested at day 10. Gross polyps were counted and measured (diameter). Microscopy showed the presence of more and larger polyps in the intestinal mucosa of control versus treated mice (data not shown). As shown in FIG. 11A, there was a significant difference between the mean polyp number, p<0.0027, in control versus treated mice. FIG. 11B shows a graph of the mean polyp size (diameter) in control and treated mice: Small=<1 mm; medium=1-2 mm; big=2-3 mm: very big=>3 mm. Polyps were further analyzed for phosphorylated 4EBP by western blotting and it was confirmed that sphingadienes inhibited 4EBP phosphorylation in vivo. Thus, administration of C14Δ4:6Sd signficantly reduced the number of intestinal polyps in mice and also reduced the size of intestinal polyps.

In summary, the results from these experiments show that C14 sphingadienes promote colon cancer cell death by apoptosis, autophagy and by blocking AKT signaling. Inhibiting Wnt signaling and inhibiting the SK/S1P axis. In vivo murine experiments demonstrated that administration of sphingadienes can reduce the number and size of intestinal polyps. These results support the use of the sphingadiene compounds for the treatment of cancers or other diseases associated with aberrant AKT or Wnt signaling pathways or aberrant SK activity.

The following list of references is provided to assist one skilled in the art in the practice of invention.

1. Espey, D., X. Wu, J. Swan, C. Wiggins, M. Jim. E. Ward, P. Wingo, H. Howe, L. Ries. B. Miller. A. Jemal, F. Ahmed. N. Cobb, J. Kaur, and B. Edwards. 2007. Annual report to the nation on the status of cancer, 1975-2004, featuring cancer in American Indians and Alaska natives Cancer 110: 2119-2152.
2. Merrill, A. H., Jr., M. C. Sullards, E. Wang, K. A. Voss, and R. T. Riley. 2001. Sphingolipid metabolism: roles in signal transduction and disruption by fumonisins. *Environ Health Perspect* 109 Suppl 2: 283-289.
3. Saba, J., and T. HIa. 2004. Point-counterpoint of sphingosine 1-phosphate metabolism. *Circ Res* 94: 724-734.
4. Helms, J., and C. Zurzolo. 2004. Lipids as targeting signals: lipid rafts and intracellular trafficking. *Traffic* 5: 247-254.
5. Degroote, S., J. Woithoom, and G. van Meer. 2004. The cell biology of glycosphingolipids. *Semin. Cell Dev. Biol* 15: 375-387.
6. Ma, D. 2007. Lipid mediators in membrane rafts are important determinants of human health and disease. *Appl. Physiol. Nutr. Metab* 32: 341-350.
7. Sillence. D. 2007. New insights into glycosphingolipid functions—storage, lipid rafts, and translocators. *Int. Rev. Cytol* 262; 151-189.
8. Pyne, S., and N. J. Pyne. 2000. Sphingosine 1-phosphate signalling in mammalian cells. *Biochem J* 349: 385-402.
9. Ohanian, J., and V. Ohanian. 2001. Sphingolipids in mammalian cell signalling. *Cell Mol Life Sci* 58: 2053-2068.
10. Taha, T., Y. Hannun, and L. Obeid. 2006. Sphingosine kinase: biochemical and cellular regulation and role in disease. *J Biochem Mol Biol* 39: 113-131.
11. El Alwani, M., B. X. Wu. L. M. Obeid, and Y. A. Hannun. 2006. Bioactive sphingolipids in the modulation of the inflammatory response. *Pharmacol Ther* 112: 171-183.
12. Chiba, K. H. Matsuyukl, Y. Maeda, and K. Sugahara. 2006. Role of sphingosine 1-phosphate receptor type 1 In lymphocyte egress from secondary lymphoid tissues and thymus. *Cell Mol. Immunol.* 3: 11-19.
13. Liu. Y., R. Wada. T. Yamashita, Y. Mi, C. X. Deng, J. P. Hobson, H. M. Rosenfeldt. V. E. Nava. S. S. Chae, M. J. Lee. C. H. Liu, T. Hla, S. Spiegel, and R. L. Prola. 2000. Edg-1, the G protein-coupled receptor for sphingosine-1-phosphate, is essential for vascular maturation. *J Clin Invest* 106: 951-961.
14. Huwiler, A., and J. Pfeilschifter. 2006. Altering the sphingosine-1-phosphate/ceramide balance: a promising approach for tumor therapy. *Curr Pharm Des* 12: 4625-4635.
15. Liu, Y., T. Han, A. Giuliano, and M. Cabot. 2001. Ceramide glycosylation potentiates cellular multidrug resistance. *Faseb J* 15: 719-730.
16. Kohno, M., M. Momoi, M. Oo, J. Paik, Y. Lee. K. Venkataraman, Y. Ai, A. Ristimaki, H. Fyrst, H. Sano, D. Rosenberg, J. Saba, R. Proia, and T. Hla. 2006. Intracellular role for sphingosine kinase 1 in intestinal adenoma cell proliferation. *Mol Cell Biol* 26: 7211-7223.
17. Oskouian, B., P. Sooriyakumaran, A. Borowsky, A. Crans, L. DIllard-Telm, Y. Tam, P. Bandhuvula, and J. Saba. 2006. Sphingosine-1-phosphate lyase potentiates apoptosis via p53- and p38-dependent pathways and is downregulated in colon cancer. *Proc Natl Acad Sci USA* 103: 17384-17389.
18. Kolesnick, R. 2002. The therapeutic potential of modulating the ceramidelsphingomyelin pathway. *J Clin Invest* 110: 3-8.
19. Zheng, W., J. Kollmeyer, H. Symolon, A. Momin, E. Munter, E. Wang, S. Kelly, J. Allegood, Y. Liu, Q. Peng, H. Ramaraju, M. Sullards, M. Cabot, and A. J. Merrill. 2006. Ceramides and other bioactive sphingolipid backbones in health and disease: lipidomic analysis, metabolism and roles in membrane structure, dynamics, signaling and autophagy. *Biochim Blophys Acta* 1758: 1864-1884.
20. Radin, N. S. 2003. Designing anticancer drugs via the achilles heel: ceramide, allylic ketones, and mitochondria. *Biooig Med Chem* 11: 2123-2142.
21. Radin, N. S. 2003. Killing tumours by ceramide-induced apoptosis: a critique of available drugs. *Biochem J* 371: 243-256.
22. Sullards, M., D. Lynch, A. J. Merrill, and J. Adams. 2000. Structure determination of soybean and wheat glucosylceramides by tandem mass spectrometry. *J Mass Spectrom* 35: 347-353.
23. Oskouian. B., and J. D. Saba. 2004. Death and taxis: what non-mammalian models tell us about sphingosine-1-phosphate. *Semin Cell Dev Biol* 15: 529-540.
24. Abnet, C., C. Borkowf, Y. Qiao, P. Albert, E. Wang, A. Merrill, Jr., S. Mark, Z. Dong, P. Taylor, and S. Dawsey. 2001. A cross-sectional study of human serum sphingolipids, diet and physiological parameters. *J Nutr* 131: 2748-2752.
25. Nilsson, A., and R. D. Duan. 2006. Absorption and lipoprotein transport of sphingomyelin. *J Lipid Res* 47: 154-171.
26. Schmelz, E. M., D. L. Dillehay, S. K. Webb. A. Reiter, J. Adams, and A. H. Merrill, Jr. 1996. Sphingomyelin consumption suppresses aberrant colonic crypt foci and increases the proportion of adenomas versus adenocarcinomas in $CF_1$ mice treated with 1,2-dimethylhydrazine; implications for dietary sphingolipids and colon carcinogenesis. *Cancer Res* 56: 4936-4941.
27. Ahn, E. H., and J. J. Schroeder. 2002. Sphingoid bases and ceramide induce apoptosis in HT-29 and HCT-116 human colon cancer cells. *Exp Biol Med* (*Maywood*) 227: 345-353.
28. Sweeney, E. A., C. Sakakura, T. Shirahama, A. Masamune, H. Ohta, S. Hakomori, and Y. Igarashi. 1996. Sphingosine and its methylated derivative N,N-dimethylsphingosine (DMS) induce apoptosis in a variety of human cancer cell lines. *Int J Cancer* 66: 358-366.
29. Berra, B., I. Colombo, E. Sottocomola, and A. Giacosa. 2002. Dietary sphingolipids in colorectal cancer prevention. *Eur J Cancer Prev* 11: 193-197.

30. Lemonnier, L. A., D. L. Dillehay, M. J. Vespremi, J. Abrams, E. Brody, and E. M. Schmelz. 2003. Sphlingomyelin in the suppression of colon tumors: prevention versus intervention. *Arch Blochem Biophys* 419: 129-138.

31. Schmelz, E. M., P. C. Roberts, E. M. Kustin, L. A. Lemonnier, M. C. Sullards, D. L. Dillehay, and A. H. Merrill, Jr. 2001. Modulation of intracellular beta-catenin localization and Intestinal tumorigenesis in vivo and in vitro by sphingolipids. *Cancer Res* 61: 6723-6729.

32. Symolon, H., E. Schmez., D. Dillehay, and A. J. Merrill. 2004. Dietary soy sphingolipids suppress tumorigenesis and gene expression in 1,2-dimethylhydrazine-treated CF1 mice and ApcMin/+ mice. *J Nutr* 134:1157-1161.

33. Adachi-Yamada, T., T. Gotoh, I. Sugimura, M. Tateno, Y. Nishida, T. Onuki, and H. Date. 1999. De novo synthesis of sphingolipids is required for cell survival by down-regulating c-Jun N-terminal kinase in *Drosophila* imaginal discs. *Mol Cell Bid* 19: 7276-7286.

34. Herr, D. R., H. Fyrst, M. B. Creason, V. H. Phan, J. D. Saba, and G. L. Harris.

2004. Characterization of the *Drosophila* sphingosine kinases and requirement for Sk2 in normal reproductive function. *J Biol Chem* 279: 12685-12694.

35. Herr, D. R., H. Fyrst. V. Phan, K. Heinecke, R. Georges, G. L. Harris, and J. D. Saba. 2003. Sply regulation of sphingolipid signaling molecules is essential for *Drosophila* development. *Development* 130: 2443-2453.

36. Kohyama-Koganeya, A., T. Sasamura, E. Oshima. E. Suzuki, S. Nishihara, R. Ueda, and Y. Hirabayashi. 2004. *Drosophila* glucosylceramide synthase: a negative regulator of cell death mediated by proapoptotic factors. *J Biol Chem* 279: 35995-36002.

37. Phan, V., D. Herr, D. Panton, H. Fyrst. J. Saba, and G. Harris. 2007. Disruption of sphingolipid metabolism elicits apoptosis-associated reproductive defects in *Drosophila. Dev Bio* 309: 329-341.

38. Fyrst, H., D. R. Herr, G. L. Harris, and J. D. Saba. 2004. Characterization of free endogenous C14 and C16 sphingoid bases from *Drosophila melanogaster. Lipid Res* 45: 54-62.

39. Lynch, D., and T. Dunn. 2004. An introduction to plant sphingolipids and a review of recent advances in understanding their metabolism and function. *New Phytologist* 161: 677-702.

40. Panganamala, R., J. Geer, and D. Comwell. 1969. Long-chain bases in the sphingolipids of atherosclerotic human aorta. *J Lipid Res* 10: 445-455.

41. Renkonen, O. 1970. Presence of sphingadienine and trans-monoenoic fatty acids in ceramide monohexosides of human plasma. *Biochim Blophys Acta* 210: 190-192.

42. Renkonen, O. and E. Hirvisalo. 1969. Structure of plasma sphingadienine. *J Lipid Res* 10: 687-693.

43. Colsch, B. C. Alfonso, 1. Popa, J. Portoukalian, F. Foumier. J. Tabet, and N. Baumann. 2004. Characterization of the ceramide moieties of sphingoglycolipids from mouse brain by ESI-MS/MS:identification of ceramides containing sphingadienine. *J Lipid Res* 45: 281-286.

44. Abeytunga, D., J. Glick, N. Gibson, L. Oland, A. Somogyi, V. Wysocki, and R. Polt. 2004. Presence of unsaturated sphingomyelins and changes in their composition during the life cycle of the moth *Manduca sexta. J Lipid Res* 45: 1221-1231.

45. Kwon. H. C., K. C. Lee, O. R. Cho, I. Y. Jung, S. Y. Cho, S. Y. Kim, and K. R. Lee. 2003. Sphingolipids from Bombycis Corpus 101A and their neurotrophic effects. *J Nat Prod* 66: 466-469.

46. Struckhoff, A. P., R. Bittman, M. E. Burow, S. Clejan, S. EllIott, T. Hammond, Y. Tang, and B. S. Beckman. 2004. Novel ceramide analogs as potential chemotherapeutic agents in breast cancer. *J Pharmacol Exp Ther* 309: 523-532.

47. Woodgett, J. R. 2005. Recent advances in the protein kinase B signaling pathway. *Curr Opin Cell Biod* 17: 150-157.

48. Ruggero. D., and N. Sonenberg. 2005. The Akt of translational control. *Oncogene* 24: 7426-7434.

49. Vivanco, I. and C. L. Sawyers. 2002. The phosphatidylinositol 3-Kinase AKT pathway in human cancer. *Nat Rev Cancer* 2: 489-501.

50. Carpten, J. D., A. L. Faber, C. Horn, G. P. Donoho, S. L. Briggs. C. M. Robbins, G. Hostetter, S. Boguslawski, T. Y. Moses, S. Savage, M. Uhlik, A. Un, J. Du, Y. W. Qian, D. J. Zeckner, G. Tucker-Kellogg, J. Touchman, K. Patel, S. Mousses, M. Bittner, R. Schevitz, M. H. Lai, K. L. Blanchard, and J. E. Thomas.

2007. A transforming mutation in the pleckstrln homology domain of AKT1 In cancer. *Nature* 448: 439-444.

51. Sullards, M. C., and A. H. J. Merrill. 2001. Analysis of sphingosine-1-phosphate, ceramides, and other bioactive sphingolipids by high-performance liquid chromatography. *Science's STKE* 67: 1-11.

52. Chun, J., G. Li, H. Byun, and R. Bittman. 2002. Synthesis of New Trans Double Bond Sphingolipid Analogues: D4,6 and 06 Ceramides. *J Org Chem* 67: 2600-2605.

53. Murakami, T., R. Hirono, and K. Furusawa. 2005. Efficient stereocontrolled synthesis of sphingadiene derivatives. *Tetrahedron* 61: 9233-9241

54. Moran, A., D. Hunt, S. Javid, M. Redston, A. Carothers, and M. Bertagnolli. 2004. Apc deficiency is associated with increased Egfr activity in the intestinal enterocytes and adenomas of C57BU6J-Min/+ mice. *J Biol Chem* 279: 43261-43272.

All of the U.S. patents. U.S. patent application publications, U.S. patent applications, foreign patents, foreign patent applications and non-patent publications referred to in this specification and/or listed in the Application Data Sheet are incorporated herein by reference, in their entireties.

Although the foregoing invention has been described in some detail to facilitate understanding, it will be apparent that certain changes and modifications may be practiced within the scope of the appended claims. Accordingly, the described embodiments are to be considered as illustrative and not restrictive, and the invention is not to be limited to the details given herein, but may be modified within the scope and equivalents of the appended claims.

What is claimed is:

1. A method of treating a cancer in a mammal, wherein the method comprises administering to the mammal a therapeutically effective amount of a compound selected from the group consisting of:

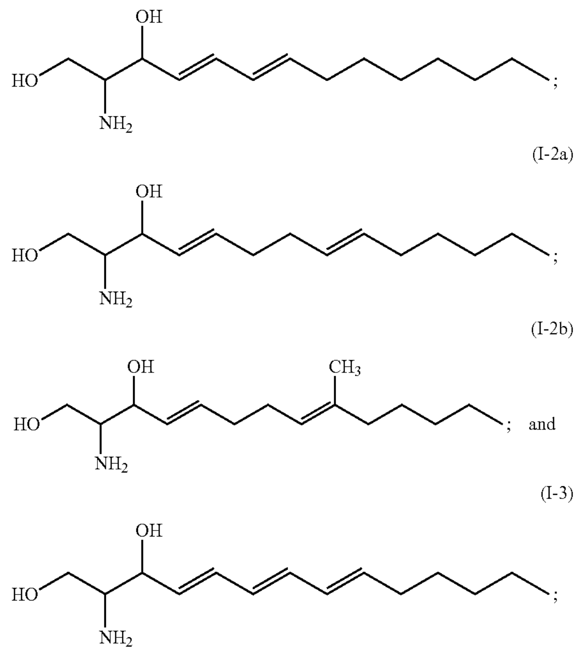

as an isolated stereoisomer or mixture thereof, or a pharmaceutically acceptable salt thereof, wherein at least one of:

a) the cancer is associated with activation of AKT, b) the cancer is associated with activation of PI3 kinase, c) the cancer is associated with a deficiency of PTEN activity, d) the cancer is associated with activation of the Wnt signaling pathway, e) the cancer comprises a gastrointestinal cancer, f) the cancer is colon cancer, g) the cancer is breast cancer, h) the cancer is neuroblastoma, i) the cancer is leukemia, or j) the cancer comprises a brain tumor.

2. The method of claim 1 wherein at least one of:

(a) the compound is administered orally, (b) the compound alters activity of a component of the AKT/$PI_3$ kinase signaling pathway, (c) the compound inhibits activity of AKT, (d) the compound inhibits cytosolic to membrane translocation of AKT, or (e) the compound activates PTEN phosphatase.

3. A method for altering the activity of an AKT/$PI_3$ kinase signaling pathway component in a mammal, or for inhibiting a Wnt signaling pathway in a mammal in need thereof, comprising administering to the mammal a therapeutically effective amount of a compound selected from the group consisting of:

(I-1)

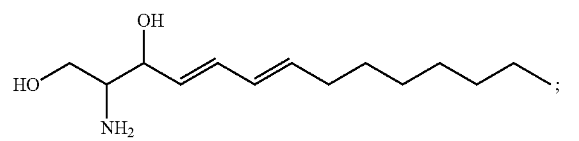

(I-2a)

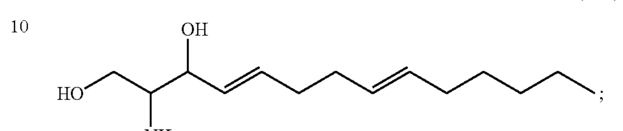

(I-2b)

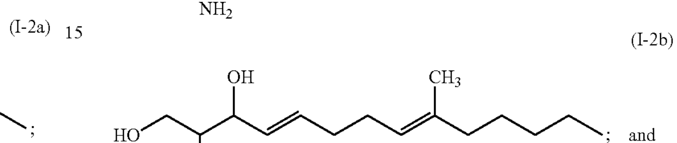

(I-3)

as an isolated stereoisomer or mixture thereof, or a pharmaceutically acceptable salt thereof.

4. The method of claim 3 wherein at least one of:

(a) the compound inhibits activity of AKT, (b) the compound inhibits cytosolic to membrane translocation of AKT, (c) the compound activates PTEN phosphatase, or (d) inhibiting the Wnt signaling pathway comprises inducing translocation of β-catenin from a nucleus of a cell to cytoplasm of the cell.

5. A method for inducing apoptosis in a cell or for inducing autophagy in a cell in a patient in need thereof, comprising contacting the cell within the patient with a therapeutically effective amount of a compound selected from the group consisting of:

(I-1)

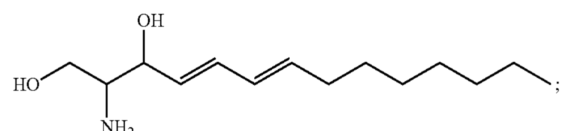

(I-2a)

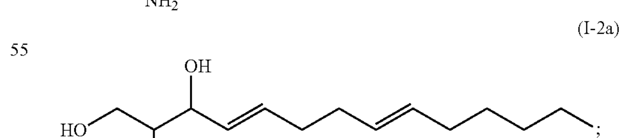

(I-2b)

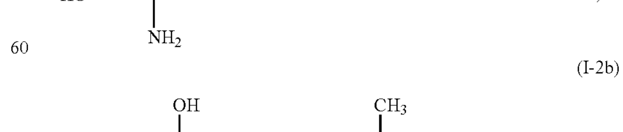

-continued (I-3)

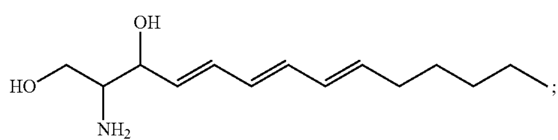

as an isolated stereoisomer or mixture thereof, or a pharmaceutically acceptable salt thereof.

6. A composition comprising a therapeutically effective amount of an mTOR inhibitor, rapamycin, or a $PI_3K$ inhibitor in combination with a compound selected from the group consisting of:

(I-1)

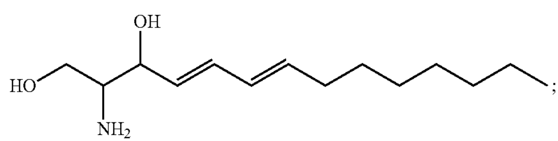

(I-2a)

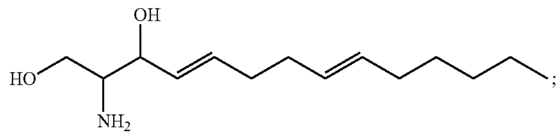

(I-2b)

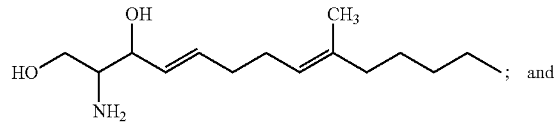

-continued (I-3)

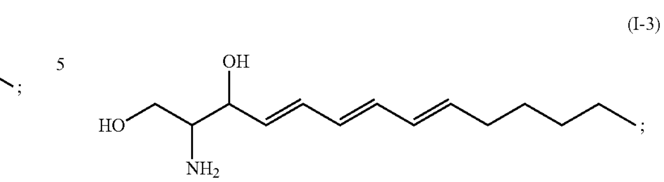

as an isolated stereoisomer or mixture thereof, or a pharmaceutically acceptable salt thereof.

7. A method of treating a cancer in a mammal, wherein the method comprises administering to the mammal a therapeutically effective amount of the composition of claim 6.

8. A method for inducing apoptosis in a cell wherein the method comprises contacting the cell with the composition of claim 6.

9. The method of claim 1 further comprising administering to the mammal a therapeutically effective amount of an mTOR inhibitor, rapamycin or a $PI_3K$ inhibitor.

10. The method of claim 9 wherein the $PI_3K$ inhibitor is selected from the group consisting of wortmannin and LY294002.

11. The method of claim 5 further comprising administering to the mammal a therapeutically effective amount of an mTOR inhibitor, rapamycin or a $PI_3K$ inhibitor.

12. The method of claim 11 wherein the $PI_3K$ inhibitor is selected from wortmannin and LY294002.

* * * * *